(12) United States Patent
Bohmert-Tatarev et al.

(10) Patent No.: US 9,096,861 B2
(45) Date of Patent: Aug. 4, 2015

(54) STABLE, FERTILE, HIGH POLYHYDROXYALKANOATE PRODUCING PLANTS AND METHODS OF PRODUCING THEM

(75) Inventors: Karen Bohmert-Tatarev, Brookline, MA (US); Susan McAvoy, Milford, MA (US); Oliver P. Peoples, Arlington, MA (US); Kristi D. Snell, Belmont, MA (US)

(73) Assignee: Metabolix, Inc., Cambridge, MA (US)

( * ) Notice: Subject to any disclaimer, the term of this patent is extended or adjusted under 35 U.S.C. 154(b) by 543 days.

(21) Appl. No.: 12/718,498

(22) Filed: Mar. 5, 2010

(65) Prior Publication Data

US 2010/0229258 A1 Sep. 9, 2010

Related U.S. Application Data

(60) Provisional application No. 61/157,809, filed on Mar. 5, 2009.

(51) Int. Cl.
*C12N 15/82* (2006.01)
*A01H 5/00* (2006.01)
*A01H 5/10* (2006.01)

(52) U.S. Cl.
CPC ........ *C12N 15/8214* (2013.01); *C12N 15/8257* (2013.01)

(58) Field of Classification Search
None
See application file for complete search history.

(56) References Cited

U.S. PATENT DOCUMENTS

| | | | |
|---|---|---|---|
| 5,380,831 A | | 1/1995 | Adang |
| 5,534,432 A | | 7/1996 | Peoples |
| 5,545,817 A | * | 8/1996 | McBride et al. ............ 800/287 |
| 5,576,198 A | * | 11/1996 | McBride et al. ............ 435/91.3 |
| 5,663,063 A | | 9/1997 | Peoples |
| 5,849,894 A | | 12/1998 | Clemente |
| 5,877,402 A | * | 3/1999 | Maliga et al. ................ 800/298 |
| 6,011,144 A | | 1/2000 | Steinbuchel |
| 6,620,601 B1 | | 9/2003 | Yamaguchi |
| 6,835,820 B2 | | 12/2004 | Cannon |
| 2002/0182690 A1 | | 12/2002 | Cannon |
| 2004/0137631 A1 | * | 7/2004 | Herz et al. ................... 435/468 |

FOREIGN PATENT DOCUMENTS

| WO | 9100917 | 1/1991 |
|---|---|---|
| WO | 9946394 | 9/1999 |
| WO | 2007121467 | 10/2007 |

OTHER PUBLICATIONS

Menzel et al, 2003, Appl. Microbiol. Biotech., 60:571-576.*
Scotti et al, 2012, Biotech. Adv., 30:387-397.*
2011, Maliga et al, Plant Phys., 155:1501-1510.*
Lössl et al, 2005, Plant Cell Physiol., 46:1462-1471.*
Kuroda et al, 2001, Nuc. Acids Res., 29: 970-975.*
Menzel et al (2003, Appl. Microbiol. Biotech., 60:571-576.*
Arai, et al, "Plastid targeting of polyhydroxybutyrate biosynthetic pathway in tobacco", Plant Biotech., 18(4):289-93 (2001).
Black, et al., "Cloning, sequencing and expression of the fadD gene of *Escherichia coli* encoding acyl coenzyme a synthetase", J Biol. Chem., 267 (35):25513-20 (1992).
Bohmert, et al., "Transgenic *Arabidopsis* plants can accumulate polyhydroxybutyrate to up to 4% of their fresh weight", Planta, 211:841-45 (2000).
Bohmert, et al., "Constitutive expression of the $^2$-ketothiolase gene in transgenic plants. A major obstacle for obtaining polyhydroxybutyrate-producing plants", Plant Phys., 128:1282-90 (2002).
Campbell, et al., "A new *Escherichia coli* metabolic competency: growth on fatty acids by a novel anaerobic $^2$-oxidation pathway", Mol. Microbio., 47(3):793-805 (2003).
Dunn and Studier, "Complete nucleotide sequence of bacteriophage T7 DNA and the location of T7 Genetic elements", J. Mol. Biol., 166:477-535 (1983).
Fukul and Doi, "Cloning and analysis of the poly(3-hydroxybutyrate-co-3-hydroxyhexanoate) biosynthesis genes of *Aeromonas caviae*", J Bacterlog., 179:4821-30 (1997).
Fukul, et al. "Expression and characterization of ®-specific enoyl coenzyme a hydratase involved in polyhydroxyalkanoate biosynthesis by *Aeromonas caviae*", J Bacterlog., 180:667-73 (1998).
Genbank accession No. AF109909, *Bacillus megaterium* polyhydroxyalkanoate gene cluster, complete sequence, 3 pages, accessed Oct. 5, 2011, updated Jun. 26, 2001, first appeared Apr. 27, 2001.
Hall, et al., "Cloning of thr *Nocardia coralline* polyhydroxyalkanoate synthase gene and production of poly-(3-hydroxybutyrate-co-3-hydroxyhexanoate) and poly-(3-hydroxyvalerate-co-3-hydroxyheptanoate)", Can, J Microbiol., 44:887-91 (1998).
Hoffmann, et al., "The *Pseudomonas aeruginosa* phaG gene product is involved in the synthesis of polyhydroxyalkanoic acid consisting of medium-chain-length constituents from non-related carbon sources", FEMS Microbial Ltts., 184:253-59 (2000).
Huisman, et al., "Metabolism of poly (3-hydroxyalkanoates) (PHAs) by *Pseudomonas oleovorans*", J Biolog. Chem., 266:2191-98 (1991).
John and Keller, "Metabolic pathway engineering in cotton: Biosynthesis of polyhydroxybutyrate in fiber cells", PNAS, 93:12768-73 (1996).
Kato, et al., "Production of a novel copolyester of 3-hydroxybutyric acid and medium-chain-length 3-hydroxalkanoic acids by *Pseudomonas* sp. 61-3 from sugars", App. MicroBio. BioTech., 45:363-70 (1996).
Kourtz, et al., "Chemically inducible expression of the PHB biosynthetic pathway in *Arabidopsis*", Transgenic. Res., 16:759-69 (2007).
Lee, et al., "Biosynthesis of copolyesters consisting of 3-hydroxybutyric acid and medium-chain-length 3-hydroxyalkanoic acids from 1,3-butanediol or from 3-hydroxybutyrate by *Pseudomonas* sp. A33", App. Micbiol. Biotech.,42:901-09 (1995).

(Continued)

*Primary Examiner* — Anne Kubelik
*Assistant Examiner* — Jason Deveau Rosen
(74) *Attorney, Agent, or Firm* — Pabst Patent Group LLP

(57) ABSTRACT

Transgenic plants that produce high levels of polyhydroxybutyrate and methods of producing them are provided. In a preferred embodiment the transgenic plants are produced using plastid transformation technologies and utilize genes which are codon optimized. Stably transformed plants able to produce greater than 10% dwt PHS in tissues are also provided.

16 Claims, 5 Drawing Sheets

(56) References Cited

OTHER PUBLICATIONS

Liebergesell and Steinbüchel, "Cloning and nucleotide sequences of genes relevant for biosynthesis of poly(3-hydroxybutyric acid) in *Chromatium vinosum* strain D", Eur J Biochem., 209:135-50 (1992).
Lössl, et al., "Polyester synthesis in transplastomic tobacco (*Nicotiana tabacum* L.): significant contents of polyhydroxybutyrate are associated with growth reduction", Plant Cell Rep., 21:891-899 (2003).
Lössl, et al., "Inducible trans-activation of plastid transgenes: expression of the *R. eutropha* phb operon in transplastomic tobacco", Plant Cell Physiol., 46:1462-1471 (2005).
Madison and Huisman, "Metabolic engineering of poly(3-hydroxyalkanoates):From DNA to plastic", Microbio Mol Biol Rev., 63:21-53 (1999).
McCool and Cannon, "Polyhydroxyalkanoate inclusion body-associated proteins and coding region in *Bacillus megaterium*", J Bacterlog., 181:585-92 (1999).
Mittendorf, et al., "Synthesis of medium-chain-length polyhydroxxyalkanoates in *Arabidopsis thaliana* using intermediates of peroxisomal fatty acid $^2$-oxidation", PNAS, 95:13397-402 (1998).
Mooney, "The second green revolution? Production of plant-based biodegradable plastics", Bioch. J, 418(2):219-32 (2009).
Nawrath, et al., "Targeting of the polyhydroxybutyrate biosynthetic pathway to the plastids of *Arabidopsis thaliana* results in high levels of polymer accumulation", PNAS, 91:12760-64 (1994).
Peoples and Sinskey, "Fine structural analysis of the *Zoogloea ramigera* phbA-phbB locus encoding $^2$-ketothiolase and acetoacetyl-CoA reductase: nucleotide sequence of phbB", Mol. Microbiol., 3:349-57 (1989).
Peoples and Sinskey, "Poly-$^2$-hydroxybutyrate biosynthesis in *Alcaligenes eutrophus* H16", J Biolog Chem., 264:15293-97 (1989).
Peoples and Sinskey, "Poly-$^2$-hydroxybutyrate (PHB) biosynthesis in *Alcaligenes eutrophus* H16", J Biolog Chem., 264:15298-303 (1989).
Petrasovits, et al., "Production of polyhydroxybutyrate in sugarcane", Plant Biotech J, 5:162-72 (2007).
Pieper and Steinbüchel, "Identification, cloning and sequence analysis of the poly(3-hydroxyalkanoic acid) synthase gene of the grampositive bacterium *Rhodococcus* rubber" FEMS Microbio. Ltts., 96:73-80 (1992).
Poirier, et al, "Increased flow of fatty acids toward $^2$-oxidation in developing seeds of *Aravidopsis*eficient in diacyiglycerol acyltransferase activity or synthesizing medium-chain-length fatty acids", Plant Phys., 121:1359-66 (1999).
Purnell, et al., "Spatio-temporal charascterizastion of polyhydroxybutyrate accumulation in sugarcane", Plant Biotech J, 5:173-84 (2007).
Rehm, et al., "A new metabolic link between fatty acid de novo synthesis and polyhydroxyalkanoic acid synthesis", J Biol Chem., 273:24044-51 (1998).
Saruul, et al., "Producion of a biodegradable plastic polymer, poly-$^2$-hydroxybutyrate, in transgenic alfalfa", Crop Sci., 42:919-27 (2002).
Schembri, et al., "Phosphate concentration regulates transcription of the acinetobacter polyhydroxyalkanoi acid biosynthetic genes", J Bacteriology, 177:4501-07 (1995).
Shinozaki, et al., "The complete nucleotide sequence of the tobacco chloroplast genome: its gene organization and expression", EMBRO, 5:2043-49 (1986).
Slater, et al., "Multiple $^2$-ketothiolases mediate poly($^2$-hydroxyaklkanoate) copolymer synthesis in *Ralstonia eutropha*", J Bacteriology, 180:1979-87 (1998).
Slater, et al., "Metabolic engineering of *Arabidopsis* and *Brassica* for poly(3-hydroxybutyrate-co-3-hydtoxyvalerate) copolymer production", Nature Am., 17:1011-16 (1999).
Snell and Peoples, "Polyhydroxyalkanoate polymers and their production in transgenic plants", Metabolic Eng., 4:29-40 (2002).
Sudesh, et al., "Synthesis, structure and properties of polyhydroxyalkanoates: biological polyesters", Prog. Polym. Sci., 25:1503-55 (2000).
Suriyamongkol, et al., "Biotechnological approaches for the production of polyhydroxyalkanoates in microorganisms and plants—A review", Biotech. Adv., 25 (2):148-75 (2007).
Timm and Steinbüchel, "Cloning and molecular analysis of the poly(3-hydroxyalkanoic acid) gene locus of *Pseudomonas aeruginosa* PAO1", Eur. J. Biochem., 209:15-30 (1992).
Valentin, et al., "PHA production, from bacteria to plants", J Biol. Macro., 25:303-306 (1999).
Van Beilen, et al., "DNA sequence determination and functional characterization of the OCT-plasmid-encoded alkJKL genes of *Pseudomonas oleovorans*", Mole Microbio., 6(21):3121-36 (1992).
Wang, et al., "Synthesis of medium-chain-length-polyhydroxyalkanoates in tobacco via chloroplast genetic engineering", Chinese Sci. Bull., 50 (11):1113-1120 (2005).
Wróbel, et al., "Polyhydroxybutyrate synthesis in transgenic flax", J Biotech., 107:41-54 (2004).
Wróbel, et al., "Engineering of PHB synthesis causes improved elastic properties of flax fibers", Biotechnol. Prog., 23:269-277 (2007).

* cited by examiner

STABLE, FERTILE, HIGH POLYHYDROXYALKANOATE PRODUCING PLANTS AND METHODS OF PRODUCING THEM

CROSS REFERENCE TO RELATED APPLICATION

This application claims the benefit of U.S. Provisional Application No. 61/157,809, filed on Mar. 5, 2009. The entire disclosure of the above application is incorporated herein by reference.

STATEMENT REGARDING FEDERAL FUNDING OR SUPPORT

This work was supported in part by a Department of Energy Industry of the Future Award (DE-FC07-011D14214) and a grant from the United States Department of Agriculture (USDA-68-3A75-3-142). Therefore the government has certain rights in the invention.

FIELD OF THE INVENTION

The invention is generally related to the field of polymer production in transgenic plants. Methods for producing stable, high polyhydroxyalkanoate producing transgenic plants via plastid transformation technologies are also provided.

BACKGROUND OF THE INVENTION

Fuels, plastics, and chemicals derived from agricultural feedstocks are receiving considerable attention as the world looks for alternatives to petroleum. Production of polyhydroxyalkanoates (PHAs), a family of naturally renewable and biodegradable plastics, in crops has the potential of providing a renewable source of polymers and bio-energy from one crop if plant residues remaining after polymer isolation are converted to liquid fuels and/or energy. PHAs can provide an additional revenue stream that would make crops including bioenergy crops more economically viable.

PHAs are a natural component of numerous organisms in multiple ecosystems and accumulate in a wide range of bacteria as a granular storage material when the microbes are faced with an unfavorable growth environment, such as a limitation in an essential nutrient (Madison et al., *Microbiol. Mol. Biol. Rev.* 63:21-53 (1999); Suriyamongkol et al. *Biotechnol Adv.* 25:148-75 (2007)). The monomer unit composition of these polymers is largely dictated by available carbon source as well as the native biochemical pathways present in the organism. PHAs can be produced industrially from renewable resources in bacterial fermentations providing an alternative to plastics derived from fossil fuels. PHAs possess properties enabling their use in a variety of applications currently served by petroleum-based plastics and are capable of matching or exceeding the performance characteristics of fossil fuel derived plastics with a broad spectrum of properties that can be obtained by varying the monomer composition of homo- and co-polymers, or by manipulating properties such as molecular weight (Sudesh et al., *Prog. Polym. Sci.* 25:1503-1555 (2000)).

SUMMARY OF THE INVENTION

Transgenic plants, plant material, and plant cells for synthesis of biopolymers, for example polyhydroxyalkanoates ("PHA") are provided. In one embodiment, the transgenic plants synthesize polyhydroxybutyrate ("PHB"). Host plants, plant tissue, and plant material have been engineered to express genes encoding enzymes in the biosynthetic pathway for PHB production from the plastid genome to produce PHB. These genes include phaA, phaB, and phaC, all of which are known in the art. Preferably, native genes are selected based on their similarity in codon usage to the host plastome. Alternatively, genes are codon optimized. The genes can be introduced in the plant, plant tissue, or plant cell using conventional plant molecular biology techniques. Plants with recombinant plastids are also referred to as transplastomic plants. In certain embodiments, the transplastomic plants are fertile.

Provided herein is a transplastomic plant having one or more plastids engineered to express enzymes for the production of PHA, wherein the transgenic plant produces greater than 10%, 12%, 15% or more polyhydroxyalkanoate per unit dry cell weight in the plant tissue. For instance, the transplastomic plant can produce greater than 10% PHA per unit dry cell weight (dwt) in leaves. The transplastomic plant can produce greater than about 10%, 11%, 12%, 13%, 14%, 15%, 16%, 17%, 18%, 19%, 20% (dwt) or more in the leaves of the plant The PHA can be poly(3-hydroxybutyrate) (PHB).

The genes encoding enzymes for the production of PHA can be selected to have codon usage similar to the host plastome of the transplastomic plant. The genes encoding enzymes for the production of PHA can be codon optimized for expression in the transplastomic plant.

The transplastomic plants can be dicots or monocots. The transplastomic plant can be a biomass crop plant. Preferred host plants include, but are not limited to members of the Brassica family including *B. napus, B. rappa, B. carinata* and *B. juncea*; industrial oilseeds such as *Camelina sativa, Crambe, jatropha*, castor; *Ambidopsis thaliana*; maize; soybean; cottonseed; sunflower; palm; algae; coconut; safflower; peanut; mustards including *Sinapis alba*; sugarcane; silage corn; alfalfa; switchgrass; miscanthus; sorghum; and tobacco.

In certain embodiments, the transplastomic plants have delayed flowering relative to wild-type plants. The typical flowering time of a transplastomic plant producing more than 14% dwt PHB in parts of its leaves is no more than 100%, 110%, 120%, 130% of flowering time of a wild type plant. The final height of a transplastomic plant producing more than 16% dwt PHB in parts of its leaves is no less than 100%, 90%, 80% of the final height of a wild type plant. Other embodiments provide plant material and plant parts of the transplastomic plants including seeds, flowers, stems, and leaves. The plant material and plant parts can be used to produce a feedstock for industrial use in for example a biorefinery.

Still another embodiment provides a method for producing a transgenic plant including selecting a host plant and transfecting one or more plastids of the host plant with a vector having genes whose codon usage avoids the use of codons with a low frequency of use (<10/1000) in the host plastome and whose GC content is <50%. In one embodiment, untranslated regions (UTRs) of the vector allow high level expression of the genes wherein the sequence length of the UTRs is minimal (≤55 nucleotides) and the total amount of plastidial derived DNA in the vector is <3% (excluding sequences of the left and right flanks) such that recombination with the host plastome is limited. Preferably, the genes encode enzymes for producing polyhydroxyalkanoate.

BRIEF DESCRIPTION OF THE DRAWINGS

FIG. 3(*b*) shows a diagram of the expected integration for plasmid pUCaadA. FIG. 3(*c*) shows a diagram of the expected integration for plasmid pCA(2). FIG. 3(*d*) shows a diagram of the expected integration site for plasmid pCAB (2). The expected size of southern fragments when genomic DNA is digested with Pst I and probed with Probe I are shown in FIGS. 3(*a*) to 3(*d*) with a dashed line.

DETAILED DESCRIPTION OF THE INVENTION

Figure 1A:
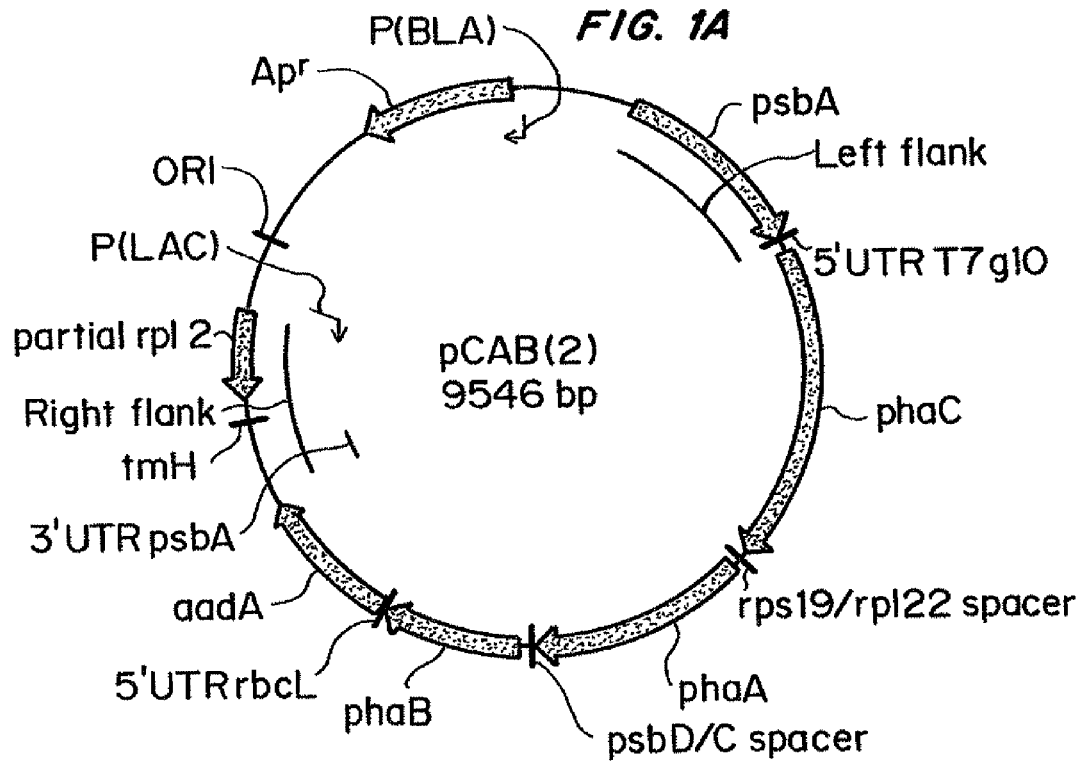
FIGS. 1(*a*)-(*c*) show diagrams of plastid transformation vectors (a) pCAB(2); (b) pCA(2); and (c) pUCaadA. The following abbreviations are used in the maps: psbA/left flank, DNA homologous to the reverse complement of nucleotides 536 to 1597 of the *N. tabacum* plastome [EMBL accession no. Z00044, (Shinozaki et al., *EMBO J.* 5: 2043-2049 (1986))], contains the complete coding sequence of psbA encoding the D1 protein of photosystem II; 5' UTR T7g10, 5' UTR of gene 10 of bacteriophage T7, DNA homologous to nucleotides 22904 to 22969 of the bacteriophage T7 genome [EMBL accession no. V01146 (Dunn et al., *J. Mol. Biol.* 166:477-535 (1983))]; phaC, gene encoding PHB synthase from *Acinetobacter* sp., homologous to nucleotides 2351 to 4123 of the *Acinetobacter* sp. PHA biosynthetic gene locus [EMBL accession no. L37761 (Schembri et al., *J. Bacteriol.* 177: 4501-7 (1995))]; rps19/rpl22 spacer, DNA homologous to nucleotides 86353 to 86399 of the *N. tabacum* plastome, contains intergenic region between ribosomal protein S19 (rps19) and ribosomal protein L22 (rpl22); phaA, gene encoding thiolase from *Acinetobacter* sp., homologous to nucleotide 4206 to 5384 of the *Acinetobacter* sp. PHA biosynthetic gene locus; psbD/C spacer, DNA homologous to nucleotides 35463 to 35517 of the *N. tabacum* plastome, contains intergenic region between photosystem II D2 protein (psbD) and photosystem II 44kd protein (psbC); phaB, gene encoding acetoacetyl-CoA reductase from *Bacillus megaterium*, homologous to nucleotide 4758 to 5501 of the *Bacillus megaterium* PHA gene cluster [EMBL accession no. AF109909 (McCool et al., *J. Bacteriol.* 181:585-592 (1999))]; 5' UTR rbcL, 15 nucleotides of the 5' untranslated leader sequence of the gene encoding the large subunit of rubisco, homologous to nucleotides 57580 to 57594 of the *N. tabacum* plastome; aadA, gene encoding aminoglycoside 3'-adenyltransferase from *E. coli*, spectinomycin/streptomycin resistance marker (Svab et at, *Proc. Natl. Acad. Sci. USA* 90:913-917 (1993)); right flank, contains 3' UTR of psbA, trnH (tRNA-Histidine), and part of ribosomal protein L2 (rpl2), right flank DNA is homologous to the reverse complement of nucleotides 155398 to 155943 and 1 to 530 of the *N. tabacum* plastome; P(LAC), lac promoter of parent vector pUC19; ORI, origin of replication of vector pUC19; Ap$^r$, gene within pUC19 vector sequence encoding β-lactamase conferring resistance to ampicillin; P(BLA), promoter driving expression of gene encoding β-lactamase.

Provided herein are transplastomic plants that produce greater than 10% polyhydroxyalkanoate per unit dry cell weight (dwt) in leaves. The plants include one or more plastids engineered to express genes encoding enzymes for the production of polyhydroxyalkanoate (PHA). Also provided are methods for making such plants.

Industrial production of PHAs in crop plants would provide a low cost, renewable source of plastics. Production of PHAs in plants has been previously demonstrated in a number of crops [for review, see (Suriyamongkol et al., *Biotechnol. Adv.* 25:148-75 (2007)) and references within], including maize (Poirier et al., 2002, Polyhydroxyalkanoate production in transgenic plants, in Biopolymers, Vol 3a, Steinbuchel, A. (ed), Wiley-VHC Verlag GmbH, pgs 401-435), sugarcane (Petrasovits et al., *Plant Biotechnol. J.* 5:162-172 (2007); Purnell et al., *Plant Biotechnol. J.* 5:173-184 (2007)), switchgrass (Somleva et al., *Plant Biotechnol. J.* 6:663-678 (2008)), flax (Wrobel et al., *J. Biotechnol.* 107:41-54 (2004); Wrobel-Kwiatkowski et al., *Biotechnol. Prog.* 23:269-277 (2007)), cotton (John et al., *Proc. Natl. Acad. Sci. USA* 93:12768-12773 (1996)), alfalfa (Saruul et al., *Crop Sci.* 42:919-927 (2002)), tobacco (Arai et al., *Plant Biotechnol.* 18:289-293 (2001); Bohmert et al., *Plant Physiol.* 128:1282-1290 (2002); Lössl et al., *Plant Cell Rep.* 21:891-899 (2003); Lössl et al., *Plant Cell Physiol.* 46:1462-1471 (2005)), potato (Bohmert et al., *Plant Physiol.* 128:1282-1290 (2002)), and oilseed rape (Valentin et al., *Int. J. Biol. Macromol.* 25:303-306 (1999); Slater et al., *Nat. Biotechnol.* 17:1011-1016 (1999)) (U.S. Pat. Nos. 5,663,063 and 5,534,432) resulting in the production of a range of polymer levels depending on the crop and mode of transformation as well as the polymer composition. Most of the efforts to produce PHAs in plants have focused on production of the homopolymer poly-3-hydroxybutyrate (P3HB) or the copolymer poly-3-hydroxybutyrate-co-3-hydroxyvalerate (P3HBV). Other researchers have studied the production of PHAs having higher carbon chain lengths in the monomers (Romano et al., *Planta* 220:455-464 (2005); Mittendorf et al., *Proc. Natl. Acad. Sci. USA* 95:13397-13402 (1998); Poirier et al., *Plant Physiol.* 121:1359-1366 (1999); Matsumoto, *J. Polym. Environ.* 14:369-374 (2006); Wang et al., *Chinese Sci. Bull.* 50:1113-1120 (2005)).

To date, the highest levels of polymer have been obtained when P3HB is produced in plastids by targeting the three enzymes encoded by transgenes in the plant nucleus into the plastid using plastid targeting sequences (Suriyamongkol et al., *Biotechnol. Adv.* 25:148-75 (2007); Bohmert et al., *Molecular Biology and Biotechnology of Plant Organelles*, pp. 559-585 (2004); van Beilen et al., *Plant J.* 54:684-701 (2008)). This is likely due to the high flux of carbon through substrate acetyl-CoA in these organdies during fatty acid biosynthesis (Bohmert et al., *Molecular Biology and Biotechnology of Plant Organelles*, pp. 559-585 (2004)). Expression of three genes encoding β-keto thiolase, aceto-acetyl CoA reductase, and PHA synthase, allows the conversion of acetyl-CoA within the plastid to PHB. Levels of PHA production greater than 10% have only been demonstrated in the model plant *Arabidopsis* (Bohmert et al., *Planta* 211:841-845 (2000); Kourtz et al., *Transgenic Res.* 16:759-769 (2007); Nawrath et al., *Proc. Natl. Acad. Sci. USA* 91:12760-12764 (1994)) and not in any crops of industrial relevance.

One way to potentially increase product yield is to increase expression of the PHB transgenes. Plastid-encoded expression can potentially yield high levels of expression due to the multiple copies of the plastome within a plastid and the presence of multiple plastids within the cell. Transgenic proteins have been observed to accumulate to 45% (De Cosa et al., *Nat. Biotechnol.* 19:71-74 (2001)) and >70% (Oey et al., *Plant J.* 57:436-445 (2009)) of the plant's total soluble protein. Since plastid DNA is maternally inherited in most plants, the presence of plastid-encoded transgenes in pollen is significantly reduced or eliminated, providing some level of gene containment in plants created by plastid transformation.

Previous researchers have attempted PUB production via plastid-encoded expression of transgenes in tobacco with only limited success (Lössl et al., *Plant Cell Rep.* 21:891-899 (2003); Lössl et al., *Plant Cell Physiol.* 46:1462-1471 (2005); Arai et al., *Plant Cell Physiol.* 45:1176-1184 (2004); Nakashita et al., *Biosci. Biotechnol. Biochem.* 65:1688-1691 (2001)). The highest levels, up to 1.7% dry weight (dwt) PHB, were observed in leaves of tobacco plantlets after regeneration from callus (Lössl et al., *Plant Cell Rep.* 21:891-899 (2003)) but product levels dropped significantly during a subsequent three week in vitro culture growth period yielding an average PHB content of only 20 ppm of polymer (Lössl et al., *Plant Cell Rep.* 21:891-899 (2003)). In addition, PHB producing plants were found to be sterile, eliminating or severely limiting their utility for PHB crop production.

Researchers have also engineered plants to produce medium chain length PHAs via plastid transformation technologies using potato (Romano et al., *Planta* 220:455-464 (2005)) and tobacco (Wang et al., *Chinese Sci. Bull.* 50:1113-1120 (2005)). Levels of 0.026 and 0.48% dwt medium chain length PHA, respectively, were observed in these studies.

Provided herein are stable, fertile, transgenic plants engineered by plastid transformation technologies for the production of unexpectedly high levels of polyhydroxyalkanoates.

Also provided are transgenic plants producing ultra high levels (>10% of dry cell weight) of polymer in tissues.

I. Definitions

Unless otherwise indicated, the disclosure encompasses conventional techniques of plant breeding, microbiology, cell biology and recombinant DNA, which are within the skill of the art. See, e.g., Sambrook and Russell, *Molecular Cloning: A Laboratory Manual*, 3rd edition (2001); *Current Protocols In Molecular Biology* ((F. M. Ausubel, et al. eds., (1987)); *Plant Breeding: Principles and Prospects* (Plant Breeding, Vol 1) (1993), M. D. Hayward, N. O. Bosemark, I. Romagosa; Chapman & Hall; Coligan, Dunn, Ploegh, Speicher and Wingfeld, eds. (1995) *Current Protocols in Protein Science* (John Wiley & Sons, Inc.); the series *Methods in Enzymology, PCR 2: A Practical Approach* (M. J. MacPherson, B. D. Hames and G. R. Taylor eds. (1995), Academic Press, Inc.).

Unless otherwise noted, technical terms are used according to conventional usage. Definitions of common terms in molecular biology may be found in Lewin, *Genes VII*, Oxford University Press, 2000; Kendrew et al. (eds.), *The Encyclopedia of Molecular Biology*, Wiley-Interscience, 1999; and Robert A. Meyers (ed.), *Molecular Biology and Biotechnology, a Comprehensive Desk Reference*, VCH Publishers, Inc., 1995; Ausubel et al., 1987, *Current Protocols in Molecular Biology*, Green Publishing; Sambrook and Russell, 2001, *Molecular Cloning: A Laboratory Manual* (3rd. edition).

A number of terms used herein are defined and clarified in the following section.

The term "PHA copolymer" refers to a polymer composed of at least two different hydroxyalkanoic acid monomers.

The term "PHA homopolymer" refers to a polymer that is composed of a single hydroxyalkanoic acid monomer.

As used herein, a "vector" is a replicon, such as a plasmid, phage, or cosmid, into which another DNA segment may be inserted so as to bring about the replication of the inserted segment. The vectors can be expression vectors.

As used herein, an "expression vector" is a vector that includes one or more expression control sequences.

As used herein, an "expression control sequence" is a DNA sequence that controls and regulates the transcription and/or translation of another DNA sequence. Control sequences that are suitable for prokaryotes, for example, include a promoter, optionally an operator sequence, a ribosome binding site, and the like. Eukaryotic cells are known to utilize promoters, polyadenylation signals, and enhancers.

As used herein, "operably linked" means incorporated into a genetic construct so that expression control sequences effectively control expression of a coding sequence of interest in the host plant.

As used herein, "transformed" and "transfected" encompass the introduction of a nucleic acid into a cell by a number of techniques known in the art.

"Plasmids" are designated by a lower case "p" preceded and/or followed by capital letters and/or numbers.

As used herein the term "heterologous" means from another host. The other host can be the same or different species.

As used herein the term "improving codon utilization" means changing one or more codons in the transgene such that the codons in the transgene more closely resemble those used by the plastome encoded genes of the host plant.

The term "cell" refers to a membrane-bound biological unit capable of replication or division.

The term "construct" refers to a recombinant genetic molecule including one or more isolated polynucleotide sequences.

Genetic constructs used for plastid-encoded transgene expression in a host organism typically comprise in the 5'-3' direction, a left flank which mediates—together with the right flank—integration of the genetic construct into the target plastome; a promoter sequence; a sequence encoding a 5' untranslated region (5' UTR containing a ribosome binding site; a sequence encoding a gene of interest, such as the genes disclosed herein; a 3' untranslated region (3' UTR); and a right flank. Plastid gene expression is regulated to a large extent at the post-transcriptional level and 5' and 3' UTRs have been shown to impact RNA stability and translation efficiency (Eibl et al., *Plant J* 19, 333-345 (1999)). Due to the prokaryotic nature of plastid expression systems, one or more transgenes may be arranged in an operon such that multiple genes are expressed from the same promoter. The promoter driving transcription of the operon may be located within the genetic construct, or alternatively, an endogenous promoter in the host plastome upstream of the transgene insertion site may drive transcription. In addition, the 3'UTR may be part of the right flank. The open reading frame may be orientated in either a sense or anti-sense direction. The construct may also comprise selectable marker gene(s) and other regulatory elements for expression.

The term "plant" is used in it broadest sense. It includes, but is not limited to, any species of woody, ornamental or decorative, crop or cereal, fruit or vegetable plant, and photosynthetic green algae (e.g., *Chlamydomonas reinhardtii*). It also refers to a plurality of plant cells that are largely differentiated into a structure that is present at any stage of a plant's development. Such structures include, but are not limited to, a fruit, shoot, stem, leaf, flower petal, etc. The term "plant tissue" includes differentiated and undifferentiated tissues of plants including those present in roots, shoots, leaves, pollen, seeds and tumors, as well as cells in culture (e.g., single cells, protoplasts, embryos, callus, etc.). Plant tissue may be in planta, in organ culture, tissue culture, or cell culture. The term "plant part" as used herein refers to a plant structure, a plant organ, or a plant tissue.

A non-naturally occurring plant refers to a plant that does not occur in nature without human intervention. Non-naturally occurring plants include transgenic plants and plants produced by non-transgenic means such as plant breeding.

With regard to plants, the term "fertile" refers to a plant producing seeds that are able to germinate and to produce viable plants.

The term "days to flowering" refers to the day of seed imbibition until opening of the first flower of the first inflorescence.

The term "plant cell" refers to a structural and physiological unit of a plant, comprising a protoplast and a cell wall. The plant cell may be in form of an isolated single cell or a cultured cell, or as a part of higher organized unit such as, for example, a plant tissue, a plant organ, or a whole plant.

The term "plant cell culture" refers to cultures of plant units such as, for example, protoplasts, cells in cell culture, cells in plant tissues, pollen, pollen tubes, ovules, embryo sacs, zygotes and embryos at various stages of development.

The term "plant material" refers to leaves, stems, roots, flowers or flower parts, fruits, pollen, egg cells, zygotes, seeds, cuttings, cell or tissue cultures, or any other part or product of a plant.

A "plant organ" refers to a distinct and visibly structured and differentiated part of a plant such as a root, stem, leaf, flower bud, or embryo.

"Plant tissue" refers to a group of plant cells organized into a structural and functional unit. Any tissue of a plant whether in a plant or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

II. Transgenic Plants

Transgenic plants, in particular, transplastomic plants, have been developed that produce increased levels of biopolymers such as polyhydroxyalkanoates (PHAs). Methods and constructs for engineering plant plastids with genes for high level, stable PHA, in particular PHB, production are described. One embodiment provides transgenic plants for the direct, large scale production of PHAs in crop plants or in energy crops where a plant by-product, such as biomass can be used for production of energy. Proof of concept studies for polyhydroxybutyrate (PHB) synthesis in switchgrass (Somleva et al., *Plant Biotechnol. J.* 6:663-678 (2008)), sugarcane (Petrasovits et al., *Plant Biotechnol. J.* 5:162-172 (2007); Purnell et al., *Plant Biotechnol. J.* 5:173-184 (2007)), canola (Valentin et al., *Int. J. Biol. Macromol.* 25:303-306 (1999); Slater et al., *Nat. Biotechnol.* 17:1011-1016 (1999); Houmiel et al., *Planta* 209:547-550 (1999)), and corn stover (Poirier et al., 2002, Polyhydroxyalkanoate production in transgenic plants, in Biopolymers, Vol 3a, Steinbuchel, A. (ed), Wiley-VHC Verlag GmbH, pgs 401-435), have been reported. While these studies have yielded significant scientific results (Slater et al., *Nat. Biotechnol.* 17:1011-1016 (1999)), higher yields will enhance overall economics of polymer produced in a crop platform.

As shown herein, fertile transgenic plants that produced elevated levels of PHAs, i.e., at least 10% dwt in plant tissues, were produced using plastid-encoded gene expression. Genes were selected whose codon usage and GC content were similar to the host plant's native plastome, avoiding the use of genes with codons with a low frequency of use (<10/1000) in the host plastome and whose GC content is <50%. In one embodiment, untranslated regions (UTRs) of the vector allow high level expression of the genes wherein the sequence length of the UTRs is minimal (≤55 nucleotides) and the total amount of plastidial derived DNA in the vector is <3% (excluding sequences of the left and right flanks) such that recombination with the host plastome is limited. This strategy allowed significantly increased PHB production in both hetero- and autotrophically grown plants compared to previously published results (>11 fold higher) (Lössl et al., *Plant Cell Rep.* 21:891-899 (2003); Lössl et al., *Plant Cell Physiol.* 46:1462-1471 (2005); Arai et al., *Plant Cell Physiol.* 45:1176-1184 (2004); Nakashita et al., *Biosci. Biotechnol. Biochem.* 65:1688-1691 (2001)).

In another embodiment, plastid encoded constructs are disclosed for optimized expression in monocots or dicots.

In yet another embodiment, constructs are disclosed for enhanced expression of PHA, preferably PHB, in algae. Preferred species of algae include, but are not limited to *Emiliana huxleyi, Arthrospira platensis* (Spirulina), *Haematococcus pluvialis, Dunaliella salina*, and *Chlamydomanas reinhardtii*.

A. Genetic Constructs for Transformation

Suitable genetic constructs include expression cassettes for plastid-encoded expression of enzymes for the production of polyhydroxyalkanoates, in particular from the polyhydroxybutyrate biosynthetic pathway. In one embodiment, the construct contains operatively linked in the 5' to 3' direction, a promoter that directs transcription of a nucleic acid sequence in the plastid; a 5' UTR that increases levels of expression of transgenes; a nucleic acid sequence encoding one of the PHB biosynthetic enzymes; and a 3' UTR that increases levels of expression of transgenes relative to expression if the UTR were not there.

In an alternative embodiment, expression of the PHB biosynthetic pathway is initiated by a promoter that is native to the host plastome and is outside of the DNA insertion.

In another embodiment, multiple genes are expressed from one promoter by creating a synthetic operon.

DNA constructs useful in the methods described herein include transformation vectors capable of introducing transgenes into plants. As used herein, "transgenic" refers to an organism in which a nucleic acid fragment containing a heterologous nucleotide sequence has been introduced. The transgenes in the transgenic organism are preferably stable and inheritable. The heterologous nucleic acid fragment may or may not be integrated into the host genome.

Traditional methods and vector options for transformation of the nuclear genome are available, including those described in "Gene Transfer to Plants" (Potrykus, et al., eds.) Springer-Verlag Berlin Heidelberg New York (1995); "Transgenic Plants: A Production System for Industrial and Pharmaceutical Proteins" (Owen, et al., eds.) John Wiley & Sons Ltd. England (1996); and "Methods in Plant Molecular Biology: A Laboratory Course Manual" (Maliga, et al. eds.) Cold Spring Laboratory Press, New York (1995). A preferred transformation approach is to use a vector to specifically transform the plant plastid chromosome by homologous recombination (as described in U.S. Pat. No. 5,545,818). Plastid transformation vectors typically include one or more coding sequences of interest whose expression is controlled by a promoter and 5' and 3' regulatory sequences, and a selectable or screenable marker gene. With plastid transformation procedures, it is possible to take advantage of the prokaryotic nature of the plastid genome and insert a number of transgenes as an operon.

A transgene may be constructed to encode a multifunctional enzyme through gene fusion techniques in which the coding sequences of different genes are fused with or without linker sequences to obtain a single gene encoding a single protein with the activities of the individual genes. Such synthetic fusion gene/enzyme combinations can be further optimized using molecular evolution technologies.

1. Genes Involved in Polyhydroxyalkanoate Synthesis

In a preferred embodiment, the products of the transgenes are enzymes and other factors required for production of a biopolymer, such as a polyhydroxyalkanoate (PHA).

For PHA production, transgenes must encode enzymes such as beta-ketothiolase, acetoacetyl-CoA reductase, PHB ("short chain") synthase, PHA ("long chain") synthase, threonine dehydratase, dehydratases such as 3-OH acyl ACP, isomerases such as Δ3-cis, Δ2-trans isomerase, propionyl-CoA synthetase, hydroxyacyl-CoA synthetase, hydroxyacyl-CoA transferase, thioesterase, fatty acid synthesis enzymes and fatty acid beta-oxidation enzymes. Useful genes are well known in the art, and are disclosed for example by Snell and Peoples *Metab. Eng.* 4:29-40 (2002) and Bohmert et al. in: *Molecular Biology and Biotechnology of Plant Organelles*, H. Daniell, C. D. Chase Eds. (Kluwer Academic Publishers, Netherlands, 2004, pp. 559-585).

PHA Synthases

Examples of PHA synthases include a synthase with medium chain length substrate specificity, such as phaC1 from *Pseudomonas oleovorans* (WO 91/00917; Huisman, et al., *J. Biol. Chem.* 266:2191-2198 (1991)) or *Pseudomonas aeruginosa* (Timm, A. & Steinbuchel, A., *Eur. J. Biochem.* 209:15-30 (1992)), the synthase from *Alcaligenes eutrophus* with short chain length specificity (Peoples, O. P. & Sinskey, A. J., *J. Biol. Chem.* 264:15298-15303 (1989)), or a two subunit synthase such as the synthase from *Thiocapsa pfennigii* encoded by phaE and phaC (U.S. Pat. No. 6,011,144). Other useful PHA synthase genes have been isolated from, for example, *Aeromonas caviae* (Fukui & Doi, *J. Bacterial.* 179: 4821-30 (1997)), *Rhodospirillum rubrum* (U.S. Pat. No. 5,849,894), *Rhodococcus ruber* (Pieper & Steinbuechel, *FEMS Microbiol. Lett.* 96(1):73-80 (1992)), and *Nocardia corallina* (Hall et al., *Can. J. Microbial.* 44:687-91 (1998)). PHA synthases with broad substrate specificity useful for producing copolymers of 3-hydroxybutyrate and longer chain length (from 6 to 14 carbon atoms) hydroxyacids have also been isolated from *Pseudomonas* sp. A33 (*Appl. Microbial. Biotechnol.* 42:901-909 (1995)) and *Pseudomonas* sp. 61-3 (Kato, et al., *Appl. Microbiol. Biotechnol.* 45:363-370 (1996)).

A range of PHA synthase genes and genes encoding additional metabolic steps useful in PHA biosynthesis are described by Madison and Huisman (*Microbiology and Molecular biology Reviews* 63:21-53 (1999)).

Hydratases

The transgene can encode a hydratase, such as the (R)-specific enoyl-CoA hydratase (PhaJ) from *Aeromonas caviae* (Fukui, T. et al., *J. Bacteriol.* 180, 667-673 (1998)) or the PhaJ1 and PhaJ2 (R)-specific enoyl-CoA hydratases from *Pseudomonas aeruginosa* (Tsuge, T. et al., *FEMS Microbiol. Lett,* 184, 193-198 (1999)). These hydratases catalyze the formation of R-3-hydroxyacyl-CoA from an enoyl-CoA.).

Reductases

The transgene can encode a reductase. A reductase refers to an enzyme that can reduce β-ketoacyl CoAs to R-3-OH-acyl CoAs, such as the NADH dependent reductase from *Chromatium vinosum* (Liebergesell, M., & Steinbuchel, A., *Eur. J. Biochem.* 209:135-150 (1992)), the NADPH dependent reductase from *Alcaligenes eutrophus* (Peoples, O. P. & Sinskey, A. J., *J. Biol. Chem.* 264:15293-15297 (1989)), the NADPH reductase from *Zoogloea ramigera* (Peoples, O. P. & Sinskey, A. J., *Molecular Microbiology* 3:349-357 (1989)) or the NADPH reductase from *Bacillus megaterium* (U.S. Pat. No. 6,835,820).

Thiolases

The transgene can encode a thiolase. A beta-ketothiolase refers to an enzyme that can catalyze the conversion of acetyl CoA and an acyl CoA to a β-ketoacyl CoA, a reaction that is reversible. An example of such thiolases are PhaA from *Alcaligenes eutropus* (Peoples, O. P. & Sinskey, A. J., *J. Biol. Chem.* 264:15293-15297 (1989)), and BktB from *Alcaligenes eutrophus* (Slater et al., *J Bacteriol.* 180(8):1979-87 (1998)).

R-3-Hydroxyacyl-ACP:CoA Transferases

The transgene can encode an R-3-hydroxyacyl-ACP:CoA transferase (PhaG), an enzyme that can convert R-3-hydroxyacyl-ACP, an intermediate in fatty acid biosynthesis, to R-3-hydroxyacyl-CoA, the monomer unit for PHA synthase and thus PHA synthesis. Genes encoding PhaG enzymes have been isolated from a range of Pseudomads, including *Pseudomonas putida* (Rehm et al., *J. Biol. Chem.*, 273, 24044-24051 (1998)), *Pseudomonas aeruginosa* (Hoffmann et al., *FEMS Microbiology Letters,* 184, 253-259 (2000)), and *Pseudomonas* sp. 61-3 (Matsumoto et al., *Biomacromolecules,* 2, 142-147 (2001)). While it has been reported that PhaG can catalyze the complete conversion of R-3-hydroxyacyl-ACP to R-3-hydroxyacyl-CoA in *Pseudomonads*, in *E. coli* it has been shown that an additional acyl CoA synthetase activity is needed to accumulate medium chain length PHAs from simple carbon sources in strains engineered to express a medium chain length synthase (US Patent Application 2003/0017576).

Acyl-CoA Synthetase

An acyl-CoA synthetase refers to an enzyme that can convert free fatty acids, including R-3-hydroxyalkanoic acids, to the corresponding acyl-CoA. Genes encoding acyl CoA synthetases have been isolated from a range of organisms, including the alkK gene from *Pseudomonas oleovorans* (van Beilen, J. et al. *Mol Microbiol,* 6, 3121-36 (1992)), the fadD gene from *E. coli* (Black, P. et al., *Biol. Chem.* 267, 25513-

25520 (1992)), and the ydiD gene from *E. coli* (Campbell et al., *Mol Microbiol.* 47, 793-805 (2003)).

2. Promoters

Plant promoters can be selected to control the expression of the transgene in different plant tissues or organdies, for all of which methods are known to those skilled in the art (Gasser & Fraley, *Science* 244:1293-99 (1989)). In a preferred embodiment, promoters are selected from those of plant or prokaryotic origin that are known to yield high expression in plastids. In certain embodiments the promoters are inducible. Inducible plant promoters are known in the art.

As shown below, the transgenes can be inserted into an existing transcription unit (such as, but not limited to, psbA) to generate an operon. However, other insertion sites can be used to add additional expression units as well, such as existing transcription units and existing operons (e.g., atpE, accD). Such methods are described in, for example, U.S. Pat. App. Pub. 2004/0137631, which is incorporated herein by reference in its entirety. For an overview of other insertion sites used for integration of transgenes into the tobacco plastome, see Staub (Staub, J. M., "Expression of Recombinant Proteins via the Plastid Genome," in: Vinci V A, Parekh S R (eds.) *Handbook of Industrial Cell Culture: Mammalian, and Plant Cells*, pp. 259-278, Humana Press Inc., Totowa, N.J. (2002)).

In general, the promoter from any class I, II or III gene can be utilized in the invention. For example, any of the following plastidial promoters and/or transcription regulation elements can be used for expression in plastids. Sequences can be derived from the same species as that used for transformation. Alternatively, sequences can be derived from other species to decrease homology and to prevent homologous recombination with endogenous sequences.

For instance, the following plastidial promoters can be used for expression in plastids.

PrbcL promoter (Allison L A, Simon L D, Maliga P, *EMBO J,* 15:2802-2809 (1996); Shiina T, Allison L, Maliga P, *Plant Cell* 10:1713-1722 (1998));
PpsbA promoter (Agrawal G K, Kato H, Asayama M, Shirai M, *Nucleic Acids Research* 29:1835-1843 (2001));
Prrn 16 promoter (Svab Z, Maliga P, *Proc. Natl. Acad. Sci. USA* 90:913-917 (1993); Allison L A, Simon L D, Maliga P, *EMBO J.* 15:2802-2809 (1996));
PaccD promoter (Hajdukiewicz P T J, Allison L A, Maliga P, *EMBO J.* 16:4041-4048 (1997); WO 97/06250);
PclpP promoter (Hajdukiewicz P T J, Allison L A, Maliga P, *EMBO J.* 16:4041-4048 (1997); WO 99/46394);
PatpB, PatpI, PpsbB promoters (Hajdukiewicz P T J, Allison L A, Maliga P, *EMBO J.* 16:4041-4048 (1997));
PrpoB promoter (Liere K, Maliga P, *EMBO J.* 18:249-257 (1999));
PatpB/E promoter (Kapoor S, Suzuki J Y, Sugiura M, *Plant J* 11:327-337 (1997)).

In addition, prokaryotic promoters (such as those from, e.g., *E. coli* or *Synechocystis*) or synthetic promoters can also be used.

3. Intergenic and Untranslated Sequences

Intergenic sequences can be used in the invention to control expression of genes.

For instance, the intergenic sequences rps19/rpl22, psbD/C, and psaA/B can be used (Herz S, Füßl M, Steiger S, Koop H-U, *Transgenic Research* 14:969-982 (2005)).

Intact or truncated 5' UTRs of highly expressed plastid genes such as psbA, atpB or rbcL have been used to regulate transgene expression in plastids at the post-transcriptional level (Staub J M, Maliga P, *EMBO J.* 12:601-606 (1993); Kuroda H, Maliga P, *Plant Physiology* 125:430-436 (2001)). The following 5'UTRs can be used in the invention.

5' UTR rbcL (Shiina T, Allison L, Maliga P, *Plant Cell* 10:1713-1722 (1998);
5' UTR psbA (Agrawal G K, Kato H, Asayama M, Shirai M, *Nucleic Acids Research* 29:1835-1843 (2001));
5' UTR of gene 10 from bacteriophage T7 has also been shown to mediate very high expression in plastids (Kuroda H, Maliga P, *Nucleic Acid Research* 29:970-975 (2001)).

The following 3' UTRs can be used to stabilize transcripts.
3' UTR rbcL (Shinozaki K, Sugiura M, *Gene* 20:91-102 (1982));
3' UTR psbA from tobacco, *Chlamydomonas*, or *Synechocystis*.

Modifications or extensions of the N-terminus of a desired protein have also been shown to increase transgene expression level (Kuroda H, Maliga P, *Nucleic Acid Research* 29:970-975 (2001); Kuroda H, Maliga P, *Plant Physiology* 125:430-436 (2001)). These sequences immediately downstream of the start codon have been called downstream boxes (DB). Examples of downstream boxes that can be used in the invention include, but are not limited to, the sequence ATG GCT AGC ATT TCC (SEQ ID NO: 1) (Herz S, Füßl M, Steiger S, Koop H-U, *Transgenic Research* 14:969-982 (2005), those listed in international application publication no. WO 00/07431, and the wild type downstream box of the T7 bacteriophage gene 10 (see, international application publication no. WO 01/21782).

4. Selectable Markers

Genetic constructs may encode a selectable marker to enable selection of plastid transformation events. There are many methods that have been described for the selection of transformed plants in traditional nuclear plant transformation methods [for review see (Mild et al., *Journal of Biotechnology* 107:193-232 (2004)) and references incorporated within].

A preferred selectable marker for plastid transformation is the bacterial aadA gene that encodes aminoglycoside 3'-adenyltransferase (AadA) conferring spectinomycin and streptomycin resistance (Svab et al., *Proc. Natl. Acad. Sci. USA* 90:913-917 (1993)). Other selectable markers that have been successfully used in plastid transformation include the spectinomycin-resistant allele of the plastid 16S ribosomal RNA gene (Staub J M, Maliga P, *Plant Cell* 4:39-45 (1992); Svab Z, Hajdukiewicz P, Maliga P, *Proc. Natl. Acad. Sci. USA* 87:8526-8530 (1990)), nptII that encodes aminoglycoside phosphotransferase for selection on kanamycin (Carrer H, Hockenberry T N, Svab Z, Maliga P., *Mol. Gen. Genet.* 241: 49-56 (1993); Lutz K A, et al., *Plant J.* 37:906-913 (2004); Lutz K A, et al., *Plant Physiol.* 145:1201-1210 (2007)), and aphA6, another aminoglycoside phosphotransferase (Huang F-C, et al., *Mol. Genet. Genomics* 268:19-27 (2002)). Another selection scheme has been reported that uses a chimeric betaine aldehyde dehydrogenase gene (BADH) capable of converting toxic betaine aldehyde to nontoxic glycine betaine (Daniell H, et al., *Curr. Genet.* 39:109-116 (2001)).

In addition methods described for selection of nuclear transformants can be used after initial selection of transplastomic lines with plastidial selection markers. Methods have been described using e.g. herbicide markers as the bar gene encoding phosphinothricin acetyltransferase or glyphosate resistant forms of the 5-enolpyruvylshikimate-3-phosphate synthase genes (US Patent Application 2002/0042934 A1; Ye et al., *Plant Physiology* 133(1): 402-410 (2003)).

Screenable marker genes include the beta-glucuronidase gene (Jefferson et al., *EMBO J.* 6:3901-3907 (1987); U.S. Pat. No. 5,268,463) and native or modified green fluorescent protein gene (Cubitt et al., *Trends Biochem. Sci.* 20:448-455 (1995); Pan et al., *Plant Physiol.* 112:893-900 (1996)). Both genes have been used in combination with the aadA gene or the spectinomycin-resistant allele of the plastid 16S ribosomal RNA gene for plastid transformation ((Hibberd et al., *Plant Journal* 16(5): 627-632 (1998); Sidorov, et al., *Plant Journal* 19(2): 209-216 (1999); Khan and Maliga, *Nature Biotechnology* 17(9): 910-915 (1999); Staub and Maliga; *EMBO J.* 12(2): 601-606 (1993)).

B. Exemplary Host Plants

Plants transformed in accordance with the present disclosure may be monocots or dicots. The transformation of suitable agronomic plant hosts using vectors for direct plastid transformation can be accomplished with a variety of methods and plant tissues. Representative plants useful in the methods disclosed herein include the Brassica family including *B. napus, B. rappa, B. carinata* and *B. juncea*; industrial oilseeds such as *Camelina saliva, Crambe, jatropha*, castor; *Arabidopsis thaliana*; maize; soybean; cottonseed; sunflower; palm; coconut; safflower; peanut; mustards including *Sinapis alba*; sugarcane and flax. Crops harvested as biomass, such as silage corn, alfalfa, switchgrass, miscanthus, sorghum or tobacco, also are useful with the methods disclosed herein. Representative tissues for transformation using these vectors include protoplasts, cells, callus tissue, leaf discs, pollen, and meristems. Representative transformation procedures include biolistics, microinjection, electroporation, polyethylene glycol-mediated protoplast transformation, liposome-mediated transformation, and silicon fiber-mediated transformation (U.S. Pat. No. 5,464,765; "Gene Transfer to Plants" (Potrykus, et al., eds.) Springer-Verlag Berlin Heidelberg New York (1995); "Transgenic Plants: A Production System for Industrial and Pharmaceutical Proteins" (Owen, et al., eds.) John Wiley & Sons Ltd. England (1996); and "Methods in Plant Molecular Biology: A Laboratory Course Manual" (Maliga, et al. eds.) Cold Spring Laboratory Press, New York (1995)). There has been one report using *Agrobacterium*-mediated transformation for plastid transformation (De Block et al., *The EMBO Journal* 4, 1367-1372 (1985)).

C. Methods of Plant Transformation

Methods for transformation of plastids such as chloroplasts are known in the art. See, for example, Svab et al., *Proc. Natl. Acad. Sci. USA* 87:8526-8530 (1990); Svab and Maliga, *Proc. Natl. Acad. Sci. USA* 90:913-917 (1993); Svab and Maliga, *EMBO J.* 12:601-606 (1993). The method relies on particle gun delivery of DNA containing a selectable marker and targeting of the DNA to the plastid genome through homologous recombination. Additionally, plastid transformation may be accomplished by transactivation of a silent plastid-borne transgene by tissue-preferred expression of a nuclear-encoded and plastid-directed RNA polymerase. Such a system has been reported in McBride et al., *Proc. Natl. Acad. Sci. USA* 91:7301-7305 (1994).

The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin were utilized as selectable markers for transformation (Svab, Z., Hajdukiewicz, P., and Maliga, P., *Proc. Natl. Acad. Sci. USA* 87:8526-8530 (1990); Staub, J. M., and Maliga, P., *Plant Cell* 4:39-45 (1992)). The presence of cloning sites between these markers allowed creation of a plastid targeting vector for introduction of foreign DNA molecules (Staub, J. M., and Maliga, P., *EMBO J.* 12:601-606 (1993)). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab, Z., and Maliga, P., *Proc. Natl. Acad. Sci. USA* 90:913-917 (1993)). Previously, this marker had been used successfully for high-frequency transformation of the plastid genome of the green alga *Chlamydomonas reinhardtii* (Goldschmidt-Clermont, M., *Nucl. Acids Res.* 19:4083-4089 (1991)).

The nucleic acids of interest to be targeted to the plastid may be optimized for expression in the plastid to account for differences in codon usage between the plant nucleus and this organelle. In this manner, the nucleic acids of interest may be synthesized using plastid-preferred codons. See, for example, U.S. Pat. No. 5,380,831, herein incorporated by reference.

Recombinase technologies which are useful for producing the disclosed transgenic plants include the cre-lox, FLP/FRT and Gin systems. Methods by which these technologies can be used for the purpose described herein are described for example in U.S. Pat. No. 5,527,695, Dale And Ow, *Proc. Natl. Acad. Sci. USA* 88:10558-10562 (1991), and Medberry et al., *Nucleic Acids Res.* 23:485-490 (1995). Another useful approach is the utilization of phiC31 phage integrase (Lutz K A, Corneille S, Azhagiri A K, Svab Z, Maliga P, *Plant J.* 37:906-913 (2004)).

D. Methods for Reproducing Transgenic Plants

Following transformation by any one of the methods described above, the following procedures can be used to obtain a transformed plant expressing the transgenes: select the plant cells that have been transformed on a selective medium; regenerate the plant cells that have been transformed to produce differentiated plants; select transformed plants expressing the transgene producing the desired level of desired polypeptide(s) in the desired tissue and cellular location.

Further rounds of regeneration of plants from explants of a transformed plant or tissue can be performed to increase the number of transgenic plastids such that the transformed plant reaches a state of homoplasmy where all plastids contain uniform plastomes containing the transgene insert.

II. Methods for Use

The disclosed vectors can be used to produce transplastomic plants that produce at least 10%, 12%, 15% PHA in regions of leaves. For the whole plant, at least about 8% or more per unit dry weight of polyhydroxyalkanoate, preferably polyhydroxybutyrate, or a co-polymer thereof can be produced.

The transplastomic plants can also produce greater than 10%, 12%, 15%, or 20% in leaves or more dwt in regions of leaves of the plant. In certain embodiments, the transplastomic plants have delayed flowering relative to wild-type plants. The transplastomic plants typically are delayed by flowering compared to the wild-type by 10%, 20%, 30% or more of the total flowering time.

The transplastomic plants can be grown and harvested. The polyhydroxyalkanoate can be isolated from the plants and the remaining plant material can be used as a feedstock for industrial use, preferably for the production of energy. The polyhydroxyalkanoate harvested from the plants can then be used to produce plastics for use in a wide range of applications such as injection molded goods, films, fibers and non-woven articles, foams, bottles and other containers and coating materials such as paper coatings and paints. PHA also can be converted to a range of chemical intermediates and has several medical applications.

The present invention will be further understood by reference to the following non-limiting examples.

EXAMPLES

Example 1

Design and Construction of Plastid Transformation Vectors

Figure 1B:
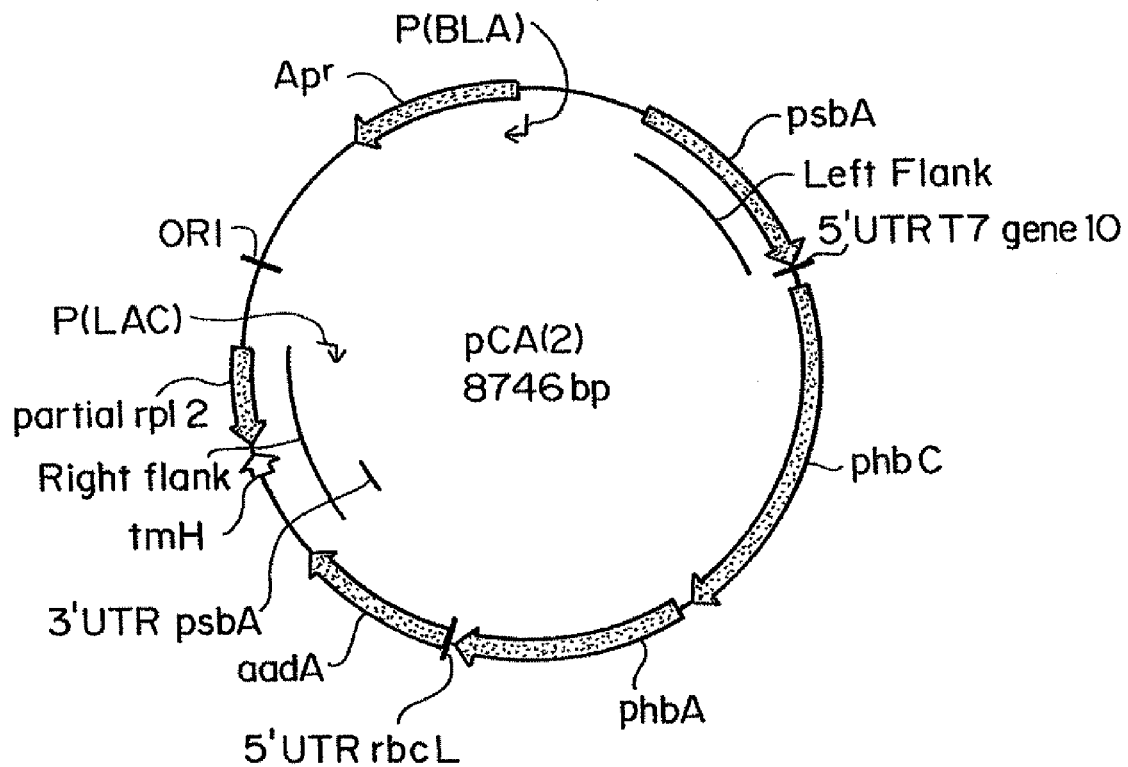
Figure 1C:
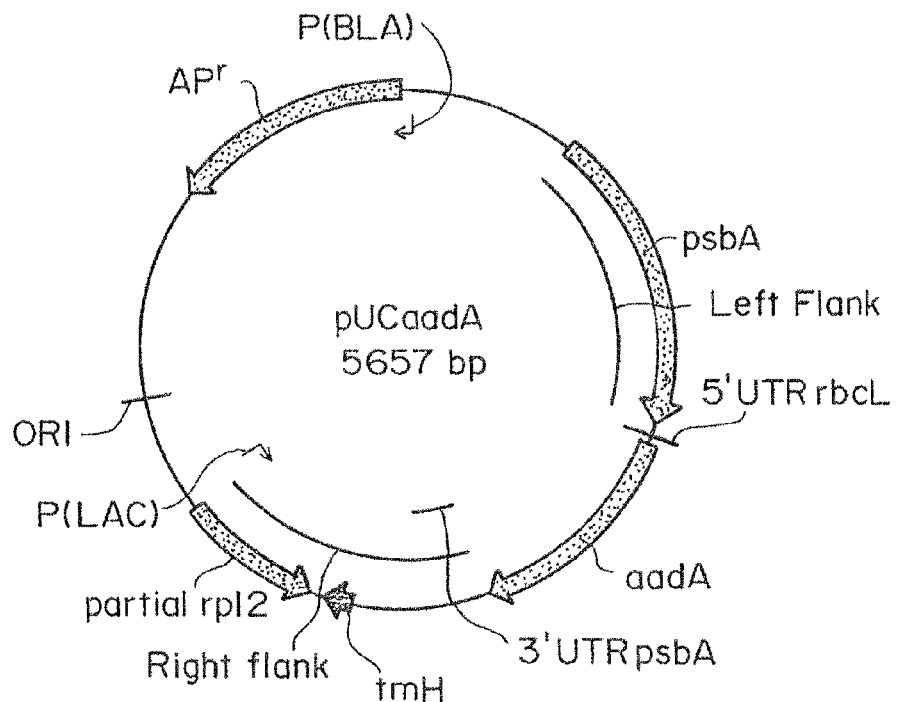

The plastome of *Nicotiana tabacum* contains 23 codons with a low frequency of use (<10/1000) (http://www.kazusa.or.jp/codon/). The presence of these codons in PHB pathway genes from various natural PHA producers as well as the overall GC content of the genes was compared to data available for the *N. tabacum* plastome. Genes from *Acinetobacter* sp. (Schembri et al., *J. Bacteria* 177:4501-7 (1995)) and *Bacillus megaterium* (McCool et al., *J. Bacteriol.* 181: 585-592 (1999)) were chosen for use in plastid transformation vectors based on the similarity of GC content and codon usage to the *N. tabacum* plastome. These genes contain few codons with a low frequency of use (<10/1000) and posses GC content<50%. Detailed descriptions of the plastid transformation vectors used in this study as well as references to pertinent DNA sequences are available in FIGS. 1(*a*)-(*c*). Plasmid pJKD1425 (Schembri et al., *J. Bacterial.* 177:4501-7 (1995)) was used as the source of the *Acinetobacter* sp. PHA operon. Plasmid pGM10 (McCool et al., *J. Bacteria* 181:585-592 (1999)) was used as the source of PHB genes from *B. megaterium*.

Plastid transformation vectors were designed to yield both high level expression and limited homology to the host plastome to prevent recombination. For example the sequence length of the UTRs is minimal (≤55 nucleotides) and the total amount of plastidial derived DNA in the vector is <3% (excluding sequences of the left and right flanks) such that recombination with the host plastome is limited.

Example 2

Plastid Transformation with Constructs for High Level PHB Production

Seeds of tobacco (*Nicotiana tabacum* L. cv Petite Havana SR1) were obtained from Lehle Seeds (Round Rock, Tex.). Plants in tissue culture were grown (16 h light period, 20 to 30 μmol photons $m^{-2}$ $s^{-1}$, 23° C.; 8 h dark period, 20° C.) on Murashige and Skoog medium (Murashige et al., *Physiol. Plant.* 15:473-497 (1962)) containing 2% (w/v) sucrose. Plastid transformation was performed using a PDS 1000 System (BIO RAD, Hercules, Calif., USA) and 0.6 μm gold particles as previously described (Svab et al., *Proc. Natl. Acad. Sci. USA* 87:8526-8530 (1990); Daniell, *Methods in Molecular Biology* 62:463-489 (1997)). Selection of transplastomic lines was performed on Murashige and Skoog/sucrose medium supplemented with 500 mg/L spectinomycin. Once transferred to soil, plants were grown in growth chambers (16 h light period, 40 to 80 μmol photons $m^{-2}$ $s^{-1}$, 23° C.; 8 h dark period, 20° C.) or in a greenhouse with supplemental lighting (16 h light period, minimum 150 μmol photons $m^{-2}$ $s^{-1}$, 23-25° C.; 8 h dark period, 20-22° C.).

Figure 2:
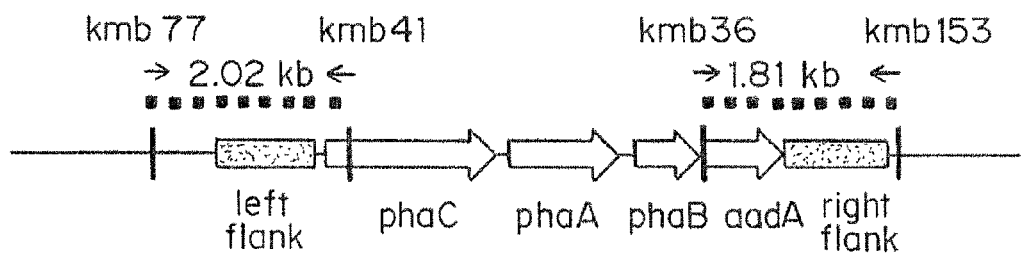
FIG. 2 shows a diagram of the insertion site of plastid transformation vector pCAB(2). The binding sites of primers KMB 77 (upstream of the transgenic DNA insert) and KMB 41 (within the transgenic DNA insert) are used to verify the correct insertion of the transgenic DNA at the left flank. The binding sites of primers KMB 153 (downstream of the transgenic DNA insert) and KMB 36 (within the transgenic DNA insert) are used to verify the correct insertion of the transgenic DNA at the right flank. Size of predicted PCR products are shown.
Figure 3A:
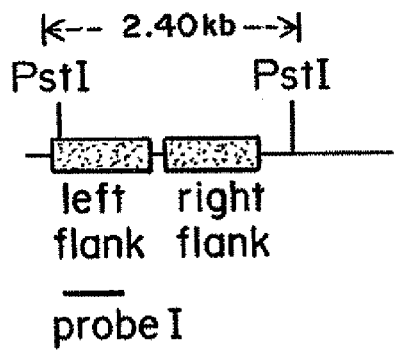
FIG. 3(*a*) shows a diagram of the wild-type locus showing the regions around sequences of the left and right flanks used in plastid transformation vectors. The left flank consists of the psbA coding region (see FIG. 1), the right flank consists of the 3' UTR of psbA, trnH, and a partial fragment of rpl2 (see FIG. 1).
Figure 3B:
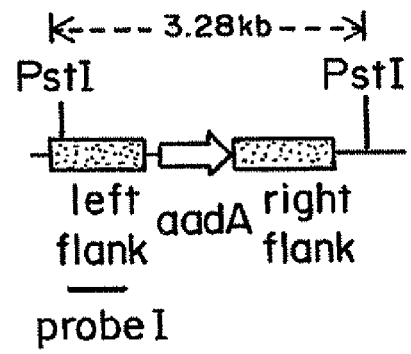
Figure 3C:
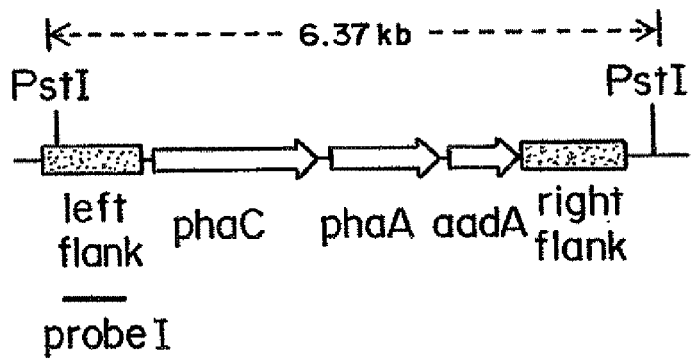
Figure 3D:
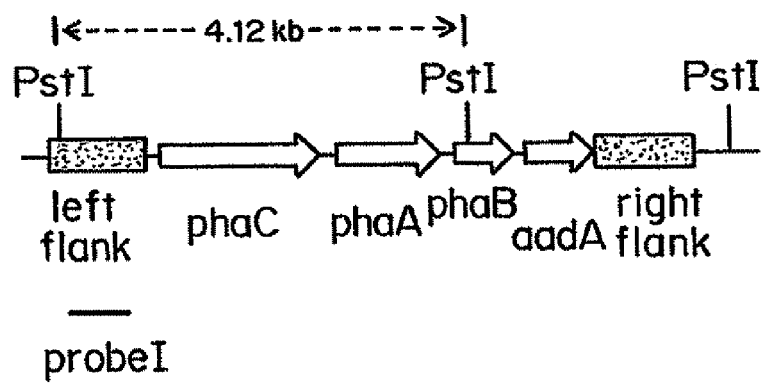
Figure 4:
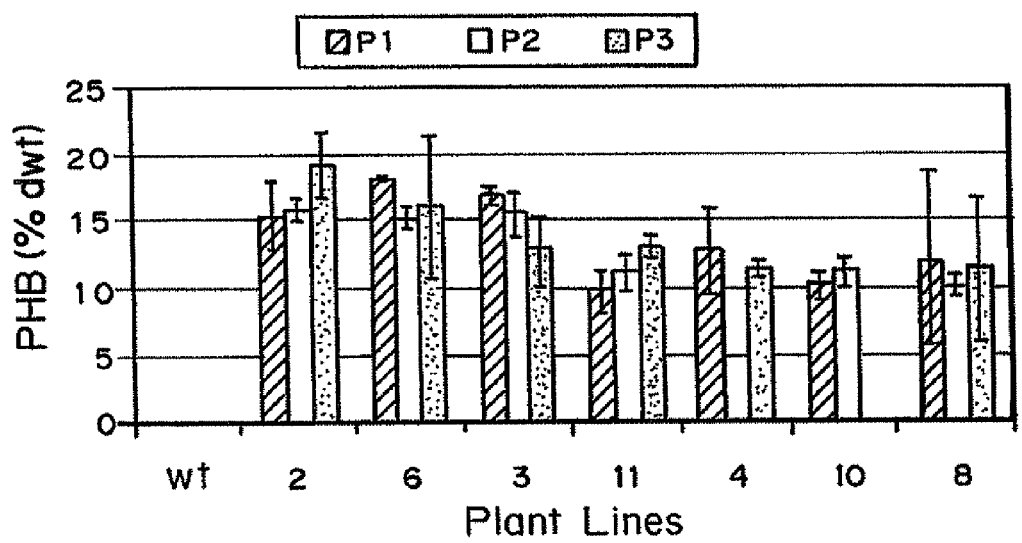
FIG. 4 shows a bar graph of PHB production in leaves of transplastomic PHB producing plants over three regeneration cycles. P1 lines were obtained after plastid transformation of pCAB(2) and isolation of regenerant. P2 lines were subjected to one additional cycle of shoot regeneration from an excised leaf. P3 lines were subjected to another additional cycle of shoot regeneration from an excised leaf.
Figure 5:
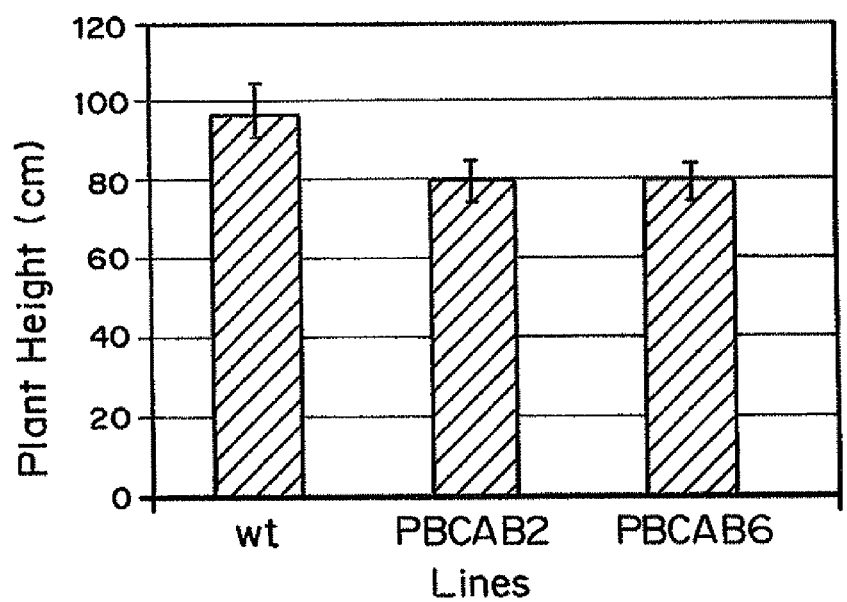
FIG. 5 shows a bar graph comparing height of wild-type and transgenic plants. Plants were grown in the green house until seed set and the height of each plant was measured. Data was obtained from 8 plants of each line. Lines are as follows: wt, wild-type; PBCAB2 and PBCAB6, these lines were obtained from seed of lines that were obtained after plastid transformation of pCAB(2), isolation of regenerant, and performance of one additional cycle of shoot regeneration from excised leaf.

Successful integration into the host plastome was verified by PCR using primers KMB41, KMB77, KMB153, and KMB36. Binding sites of these primers are shown in FIG. 2.

```
Primer KMB 41
                                               (SEQ ID NO: 2)
Sequence: 5'-ttgagctgcgccaaagcctc-3'

Primer KMB 77
                                               (SEQ ID NO: 3)
Sequence: 5'-cttgtgctagaactttagctcg-3'

Primer KMB 153
                                               (SEQ ID NO: 4)
Sequence: 5'-cca ccc atg tgg tac ttc att cta cg-3'

Primer KMB 36
                                               (SEQ ID NO: 5)
Sequence: 5'-gag ttg tag gga ggc aac cat ggc ag-3'
```

PCR analysis of plants was performed using 10-12 ng of total DNA with PCR Supermix Kit (Invitrogen). Total DNA was isolated from in vitro or green house derived tobacco leaves using the DNeasy kit (Qiagen, Santa Clarita, Calif.).

Confirmation of correct integration at the left flank was performed with primer pair KMB77 and KMB41 using conventional PCR procedures and an annealing temperature of 57° C. The expected 2.02 kb PCR product was observed in reactions with DNA from candidate plants 2, 3, 6, and 8 but not in reactions containing wild-type DNA (FIG. 2).

Confirmation of correct integration at the right flank was used with primer pair KMB153 and KMB36 using an annealing temperature of 52° C. The expected 1.81 kb PCR product was observed in reactions with DNA from candidate plants 2, 3, 6, and 8 but not in reactions containing wild-type DNA (FIG. 2).

Example 3

PHB Analysis of Transplastomic Plants

The amount of PHB present in plant tissue was measured by gas chromatography/mass spectroscopy (GC/MS) as previously described (Kourtz et al., *Transgenic Research* 16:759-769 (2007)) using 30-150 mg of lyophilized leaf material. The highest levels of PHB observed were 20.6% dwt PHB in leaf tissues of line pCAB2P3T0 and 19.6% dwt PHB in leaf tissues of line pCAB6P3T0. These lines were obtained after plastid transformation of pCAB(2), isolation of regenerant, and performance of two additional cycles of shoot regeneration from excised leaf.

Accumulation of PHB in leaves and stems were measured in plant line pCAB2.2m P2T1 and the percent dry weight accumulation throughout the plant was calculated (Table 1). Line pCAB2.2m P2T1 was obtained from seed of a plant that was obtained after plastid transformation of pCAB(2), isolation of regenerant, and performance of one additional cycle of shoot regeneration from excised leaf. In general, leaf tissue of this line contained more PHB than stem tissue. The total PHB production was 8.78% dwt of the total plant. The leaf tissue from plant pCAB2.2m P2T1 was a greater percent of the total plant biomass (71%) than leaf tissue from wild-type plants (54%) (Table 1).

TABLE 1

| | Mass of wild-type tissue* [g dwt] | Mass of CAB(2) tissue** [g dwt] | Mass Ratio CAB(2)/Wild-type | PHB [% dwt] |
|---|---|---|---|---|
| Total biomass | 33.5 ± 3.5 | 21.06 | 0.64 | 8.78 |
| Leaf biomass | 18.4 ± 2.3 | 14.98 | 0.81 | 11.18 |
| Stem biomass | 15.1 ± 1.8 | 6.08 | 0.40 | 2.87 |

*Data for wild-type tissue is an average of 5 plants.
**Data for CAB(2) tissue was obtained from a single plant that was grown from T1 seed. T1 seed was produced by a plastid transformed regenerant that was subjected to one additional cycle of shoot regeneration from an excised leaf.
dwt, dry weight. Inflorescences and seeds were not included in the measurements.

Example 4

Determination of Extent of Homoplasmy in Transformed Lines

Correct integration of the transgenes and the extent of homoplasmy of transgenic lines was analyzed by Southern analysis. Total DNA was isolated from in vitro or green house derived tobacco leaves using the DNeasy kit (Qiagen, Santa Clarita, Calif.). Aliquots of total DNA containing 2.5 to 7.5 µg were digested with the restriction enzyme Pst I and blotted onto positively charged nylon membranes (Roche Molecular Biochemicals, Indianapolis). A 0.61 kb digoxigenin-labeled hybridization probe (Probe I) for detection of genetic elements were prepared using conventional PCR procedures with the DIG probe synthesis kit (Roche Molecular Biochemicals) and oligonucleotides KMB96 and KMB97 using a primer annealing temperature of 64° C.

```
Primer KMB 96
5'-cttctgtaactggataactagcactg-3'    (SEQ ID NO: 6)

Primer KMB 97
5'-gttaccaaggaaccatgcatagcactg-3'   (SEQ ID NO: 7)
```

Hybridization signals were detected with alkaline-phosphatase conjugated anti-digoxigenin antibody and chemoluminescent detection (CDP-Star, Roche Molecular Biochemicals). DNA from a wild-type plant yielded a 2.4 kb fragment as expected for the wild-type plastome. DNA from a plant transformed with plasmid pUCaadA (FIG. 1(c)) yielded a 3.28 kb fragment as expected for insertion of a transgenic fragment containing the aadA gene. Plants from transformations of pCAB(2) yielded a prominent 4.12 kb fragment as expected for correct integration of the transgenic DNA into the plastome. Little, if any, 2.40 kb fragment was observed in pCAB(2) samples suggesting that little, if any, wild-type plastome was still present in these plants.

A method more sensitive than Southern analysis to determine the presence of wild type copies in transplastomic plants is to screen large numbers of seeds/descendants of transplastomic lines on media containing the selection agent. Segregation of copies of the plastome will lead to plants sensitive to the selection agent if wild type copies are still present. Seeds of three pCAB(2) lines (pCABP2T1 #2, #6 and #3) were therefore germinated on media containing 500 mg/ml spectinomycin and on control plates without selection agent. The germination rate and phenotype of seedlings were evaluated three weeks after plating (Table 2). Germination rates of 19, 13, and 55% were observed for pCABP2T1 transgenic lines 2, 3, and 6, respectively. Some of the germinating seeds showed mosaic white patches on their cotyledons suggesting possible sensitivity to spectinomycin. The percent of seedlings with mosaic cotyledons was 2.3, 11.6, and 0.6 for lines 2, 3, and 6, respectively. None of the seedlings derived from seeds plated on media without spectinomycin showed any mosaic patterns (Table 2) suggesting that the mosaic patterns were indeed due to a lack of spectinomycin resistance rather than other recombination events that might lead to variegated patterns. In conclusion the most stable and highest PHB producing lines #2 and #6 were shown to have small amounts of wild type copies left (2.3% and 0.6% of the seeds capable of germinating) while a less stable line (#3) showed up to 11.6% of at least partial resistance to spectinomycin. Interestingly the real leaves of the seedlings did not show any mosaic patterns on medium containing selection agent.

TABLE 2

| | Seeds Plated on Media With Spectinomycin | | | | | Seeds Plated on Media Without Spectinomycin | | | |
|---|---|---|---|---|---|---|---|---|---|
| pCAB P2T1 Line # | Seeds Plated | Seeds Germinated Total | % | Mosaic Cotelydons Total | % | Seeds Plated | Seeds Germinated Total | % | Seedlings With Mosaic Cotelydons |
| 2 | 11095 | 2140 | 19.3 | 49 | 2.3 | 1783 | 1219 | 68.4 | 0 |
| 3 | 10445 | 1357 | 13 | 158 | 11.6 | 1790 | 655 | 36.6 | 0 |
| 6 | 7656 | 4241 | 55.4 | 28 | 0.6 | 1823 | 1366 | 74.9 | 0 |
| wt | 1648 | 1237 | 75.1 | 0* | 0* | 1369 | 1025 | 74.9 | 0 |

*cotelydons were completely white/bleached indicating they are dying.

Example 5

Average Days to Flowering

In order to determine the average days to flowering, wild type seeds of Nicotiana tabacum L. cv Petite Havana SR1 were germinated on Murashige and Skoog medium (Murashige et al., Physiol. Plant. 15:473-497 (1962)) containing 2% (w/v) sucrose and T1 seeds of lines pCAB P2T1 #2 and #6, were germinated on the same media supplemented with 500 mg/ml spectinomycin. pCAB P2T1 seeds are seeds obtained from lines that were obtained after plastid transformation of pCAB(2), isolation of regenerant, and performance of one additional cycle of shoot regeneration from excised leaf. Plants in tissue culture were grown with a 16 h light period (20 to 30 µmol photons $m^{-2} s^{-1}$, 23° C.) and an 8 h dark period at 20° C. Three weeks after seed imbibition germinated seedlings were transferred to tissue culture vessels and maintained on the media described above. Six weeks after seed imbibitions, six wild type plants and eight plants of lines pCAB P2T1 #2 and #6, respectively, were transferred to a greenhouse with supplemental lighting (16 h light period, minimum 150 µmol photons $m^{-2} s^{-1}$, 23-25° C.; 8 h dark period, 20-22° C.). The onset of formation of inflorescences was monitored (see FIG. 6). Days until flowering was calculated from the day of seed imbibition until opening of the first flower of the first inflorescence.

Additional wild type plants were grown to compare the phenotypes of wild type plants and pCAB P2T1 plants in comparable developmental stages. These additional wild type plants were plated 12 and 22 days after imbibition of pCAB P2T1 seeds. Further transfers of plants to tissue culture vessels and to the green house were performed as described above. Pictures were taken from a plant of pCAB P2T1 line #2 together with a wild type plant that was 12 days younger. The photo was taken 44 days after seed imbibition of pCAB P2T1 seeds and 32 days after seed imbibition of the wild type. To document the phenotype of a plant of pCAB P2T1 line #2 together with a wild type plant at a later developmental stage (when plants had already reached their final height), a picture was taken from a plant of pCAB P2T1 line #2 together with a wild type plant that was 22 days younger. The photo was taken 85 days after seed imbibition of pCAB P2T1 seeds and 63 days after seed imbibition of the wild type.

Figure 6:
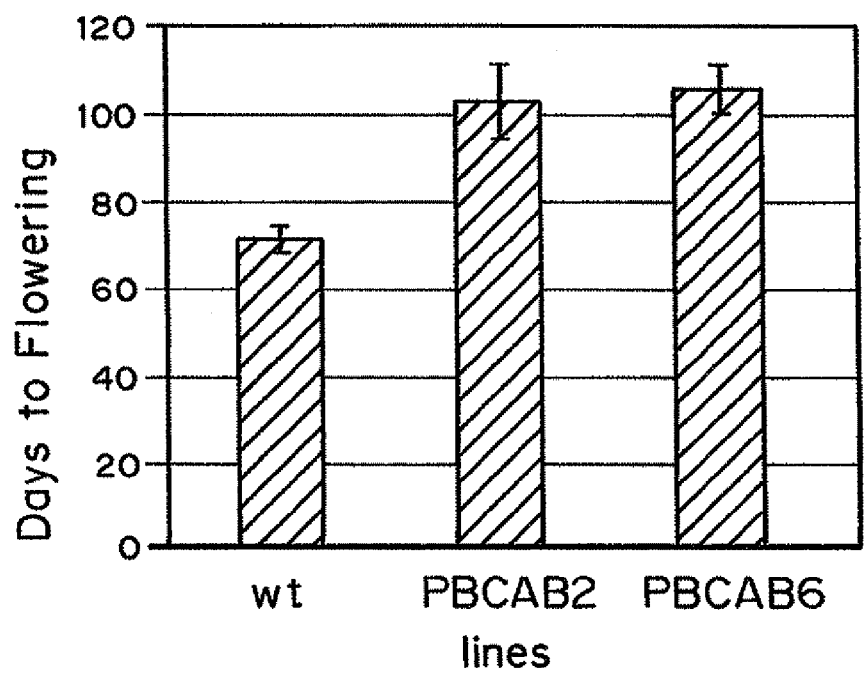
FIG. 6 shows a bar graph of the comparison of days to flowering of wild-type and transgenic plants. Plants were grown in the green house until flowers started to appear. Data was obtained from 8 plants of each line. Lines are as follows: wt, wild-type; PBCAB2, line pCAB P2 T1 #2; PBCAB6, line pCAB P2 T1 #6. Lines pCAB P2 T1 #2 and pCAB P2 T1 #6 were obtained from seed of lines that were obtained after plastid transformation of pCAB(2), isolation of regenerant, and performance of one additional cycle of shoot regeneration from excised leaf.

FIG. 6 shows a bar graph of the comparison of days to flowering of wild-type and transgenic plants. Plants were grown in the green house until flowers started to appear. Data was obtained from 8 plants of each line. Lines are as follows: wt, wild-type; PBCAB2, line pCABP2 T1 #2; and PBCAB6, line pCAB P2T1 #6. These lines were obtained from seed of lines that were obtained after plastid transformation of pCAB (2), isolation of regenerant, and performance of one additional cycle of shoot regeneration from excised leaf.

Example 6

Analysis of Chloroplasts

Leaf samples were prepared for analysis by transmission electron microscopy (TEM) by fixing in 2% paraformaldehyde, 2% glutaraldehyde, 4% sucrose, 1 mM $CaCl_2$, 2 mM $MgCl_2$ in 50 mM sodium cacodylate buffer, pH 7.2. One cm square leaf pieces were cut from the mid-blade blade area and cut into strips 0.5-1.0 mm wide while submerged in the fixative. The fixative was vacuum infiltrated into the leaf tissue at ~70 kPa for several cycles until most pieces sank. The fixation was conducted for 2 hr at room temperature. Tissue was rinsed in 3 changes of 50 mM sodium cacodylate buffer containing 4% sucrose, and post-fixed in the same buffer with 1% osmium tetroxide for 8 hr at 4° C. Tissue was rinsed in several changes of distilled water and dehydrated in acetone by 10% increments to 100% acetone, and gradually infiltrated (1:3, 1:2, 1:1, 2:1, 3:1, 100%) with Ellis low-viscosity epoxy resin formulation (Ellis, E., *Ann. Microscopy Today* 14:32-33 (2006)), an update of the Spurr's resin mixture (Spurr, A. R., J., *Ultrastructure Res.* 26:31 (1969)). The samples received 3 changes of 100% resin at 2 hr intervals, were embedded in the same and polymerized 16 hr at 70° C. Sections were cut at 60 nm thickness, mounted on copper grids, and stained 20 minutes at room temperature with uranyl acetate (uranyl acetate solution was saturated at 4° C. in 50% ethanol), and 3 minutes in lead citrate (2.5 mg/ml in 0.1 N NaOH). Sections were observed at 80 kV in a JEOL JEM-100S transmission electron microscope and photographed with a CCD camera (SIA, Model 7C).

The absence of starch granules, the smaller size of plastoglobuli, and the presence of PHB granules in transplastomic chloroplasts was noted in line pCAB2.7 P2 T1 producing 5.4% dwt PHB and line pCAB2.1 P2 T1 producing 6.3% dwt PHB. PHB analysis was performed using the tip of each leaf sampled for TEM analysis.

Unless defined otherwise, all technical and scientific terms used herein have the same meanings as commonly understood by one of skill in the art to which the disclosed invention belongs. Publications cited herein and the materials for which they are cited are specifically incorporated by reference.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10. The terms "one," "a," or "an" as used herein are intended to include "at least one" or "one or more," unless otherwise indicated.

Those skilled in the art will recognize, or be able to ascertain using no more than routine experimentation, many equivalents to the specific embodiments of the invention described herein. Such equivalents are intended to be encompassed by the following claims.

```
Sequence of pUCaadA
  1 TTGAAGCATT TATCAGGGTT ATTGTCTCAT GAGCGGATAC ATATTTGAAT (SEQ ID NO: 8)
    AACTTCGTAA ATAGTCCCAA TAACAGAGTA CTCGCCTATG TATAAACTTA (SEQ ID NO: 9)

51 GTATTTAGAA AAATAAACAA ATAGGGGTTC CGCGCACATT TCCCCGAAAA
    CATAAATCTT TTTATTTGTT TATCCCCAAG GCGCGTGTAA AGGGGCTTTT

101 GTGCCACCTG ACGTCTAAGA AACCATTATT ATCATGACAT TAACCTATAA
    CACGGTGGAC TGCAGATTCT TTGGTAATAA TAGTACTGTA ATTGGATATT

151 AAATAGGCGT ATCACGAGGC CCTTTCGTCT CGCGCGTTTC GGTGATGACG
    TTTATCCGCA TAGTGCTCCG GGAAAGGAGA GCGCGCAAAG CCACTACTGC

201 GTGAAAACCT CTGACACATG CAGCTCCCGG AGACGGTCAC AGCTTGTCTG
    CACTTTTGGA GACTGTGTAC GTCGAGGGCC TCTGCCAGTG TCGAACAGAC

251 TAAGCGGATG CCGGGAGCAG ACAAGCCCGT CAGGGCGCGT CAGCGGGTGT
    ATTCGCCTAC GGCCCTCGTC TGTTCGGGCA GTCCCGCGCA GTCGCCCACA

301 TGGCGGGTGT CGGGGCTGGC TTAACTATGC GGCATCAGAG CAGATTGTAC
    ACCGCCCACA GCCCCGACCG AATTGATAGG CCGTAGTCTC GTCTAACATG
```

-continued

```
 351 TGAGAGTGCA CCATATGCGG TGTGAAATAC CGCACAGATG CGTAAGGAGA
     ACTCTCACGT GGTATACGCC ACACTTTATG GCGTGTCTAC GCATTCCTCT

401 AAATACCGCA TCAGGCGCCA TTCGCCATTC AGGCTGCGCA ACTGTTGGGA
     TTTATGGCGT AGTCCGCGGT AAGCGGTAAG TCCGACGCGT TGACAACCCT

451 AGGGCGATCG GTGCGGGCCT CTTCGCTATT ACGCCAGCTG GCGAAAGGGG
     TCCCGCTAGC CACGCCCGGA GAAGCGATAA TGCGGTCGAC CGCTTTCCCC

501 GATGTGCTGC AAGGCGATTA AGTTGGGTAA CGCCAGGGTT TTCCCAGTCA
     CTACACGACG TTCCGCTAAT TCAACCCATT GCGGTCCCAA AAGGGTCAGT

551 CGACGTTGTA AAACGACGGC CAGTGAATTC ATGACTGCAA TTTTAGAGAG
     GCTGCAACAT TTTGCTGCCG GTCACTTAAG TACTGACGTT AAAATCTCTC

601 ACGCGAAAGC GAAAGCCTAT GGGGTCGCTT CTGTAACTGG ATAACTAGCA
     TGCGCTTTCG CTTTCGGATA CCCCAGCGAA GACATTGACC TATTGATCGT

651 CTGAAAACCG TCTTTACATT GGATGGTTTG GTGTTTTGAT GATCCCTACC
     GACTTTTGGC AGAAATGTAA CCTACCARAC CACAAAACTA CTAGGGATGG

701 TTATTGACGG CAACTTCTGT ATTTATTATT GCCTTCATTG CTGCTCCTCC
     AATAACTGCC GTTGAAGACA TAAATAATAA CGGAAGTAAC GACGAGGAGG

751 AGTAGACATT GATGGTATTC GTGAACCTGT TTCAGGGTCT CTACTTTACG
     TCATCTGTAA CTACCATAAG CACTTGGACA AAGTCCCAGA GATGAAATGC

801 GAAACAATAT TATTTCCGGT GCCATTATTC CTACTTCTGC AGCTATAGGT
     CTTTGTTATA ATAAAGGCCA CGGTAATAAG GATGAAGACG TCGATATCCA

851 TTACATTTTT ACCCAATCTG GGAAGCGGCA TCCGTTGATG AATGGTTATA
     AATGTAAAAA TGGGTTAGAC CCTTCGCCGT AGGCAACTAC TTACCAATAT

901 CAACGGTGGT CCTTATGAAC TAATTGTTCT ACACTTCTTA CTTGGCGTAG
     GTTGCCACCA GGAATACTTG ATTAACAAGA TGTGAAGAAT GAACCGCATC

951 CTTGTTACAT GGGTCGTGAG TGGGAGCTTA GTTTCCGTCT GGGTATGCGA
     GAACAATGTA CCCAGCACTC ACCCTCGAAT CAAAGGCAGA CCCATACGCT

1001 CCTTGGATTG CTGTTGCATA TTCAGCTCCT GTTGCAGCTG CTACCGCAGT
     GGAACCTAAC GACAACGTAT AAGTCGAGGA CAACGTCGAC GATGGCGTCA

1051 TTTCTTGATC TACCCAATTG GTCAAGGAAG TTTTTCTGAT GGTATGCCTC
     AAAGAACTAG ATGGGTTAAC CAGTTCCTTC AAAAAGACTA CCATACGGAG

1101 TAGGAATCTC TGGTACTTTC AATTTCATGA TTGTATTCCA GGCTGAGCAC
     ATCCTTAGAG ACCATGAAAG TTAAAGTACT AACATAAGGT CCGACTCGTG

1151 AACATCCTTA TGCACCCATT TCACATGTTA GGCGTAGCTG GTGTATTCGG
     TTGTAGGAAT ACGTGGGTAA AGTGTACAAT CCGCATCGAC CACATAAGCC

1201 CGGCTCCCTA TTCAGTGCTA TGCATGGTTC CTTGGTAACT TCTAGTTTGA
     GCCGAGGGAT AAGTCACGAT ACGTACCAAG GAACCATTGA AGATCAAACT

1251 TCAGGGAAAC CACAGAAAAT GAATCTGCTA ATGAAGGTTA CAGATTCGGT
     AGTCCCTTTG GTGTCTTTTA CTTAGACGAT TACTTCCAAT GTCTAAGCCA

1301 CAAGAGGAAG AAACTTATAA CATCGTAGCC GCTCATGGTT ATTTTGGCCG
     GTTCTCCTTC TTTGAATATT GTAGCATCGG CGAGTRCCAA TAAAACCGGC

1351 ATTGATCTTC CAATATGCTA GTTTCAACAA CTCTCGTTCG TTACACTTCT
     TAACTAGAAG GTTATACGAT CAAAGTTGTT GAGAGCAAGC AATGTGAAGA

1401 TCCTAGCTGC TTGGCCTGTA GTAGGTATCT GGTTTACCGC TTTAGGTATC
     AGGATCGACG AACCGGACAT CATCCATAGA CCAAATGGCG AAATCCATAG

1451 AGCACTATGG CTTTCAACCT AAATGGTTTC AATTTCAACC AATCTGTAGT
     TCGTGATACC GAAAGTTGGA TTTACCAAAG TTAAAGTTGG TTAGACATCA

1501 TGACAGTCAA GGCCGTGTAA TTAATACTTG GGCTGATATC ATTAACCGTG
     ACTGTCAGTT CCGGCACATT AATTATGAAC CCGACTATAG TAATTGGCAC

1551 CTAACCTTGG TATGGAAGTT ATGCATGAAC GTAATGCTCA CAACTTCCCT
     GATTGGAACC ATACCTTCAA TACGTACTTG CATTACGAGT GTTGAAGGGA

1601 CTAGACCTAG CTGCTATCGA AGCTCCATCT ACAAATGGAT AAGTCGACAA
     GATCTGGATC GACGATAGCT TCGAGGTAGA TGTTTACCTA TTCAGCTGTT

1651 GTGTTTGCGG CCGCGAGCTC GGACTCGAGT TTGGATCCAA TCGATACAAG
     CACAAACGCC GGCGCTCGAG CCTGAGCTCA AACCTAGGTT AGCTATGTTC
```

```
1701 TGAGTTGTAG GGAGGCAACC ATGGCAGAAG CGGTGATCGC CGAAGTATCG
     ACTCAACATC CCTCCGTTGG TACCGTCTTC GCCACTAGCG GCTTCATAGC

1751 ACTCAACTAT CAGAGGTAGT TGGCGTCATC GAGCGCCATC TCGAACCGAC
     TGAGTTGATA GTCTCCATCA ACCGCAGTAG CTCGCGGTAG AGCTTGGCTG

1801 GTTGCTGGCC GTACATTTGT ACGGCTCCGC AGTGGATGGC GGCCTGAAGC
     CAACGACCGG CATGTAAACA TGCCGAGGCG TCACCTACCG CCGGACTTCG

1851 CACACAGTGA TATTGATTTG CTGGTTACGG TGACCGTAAG GCTTGATGAA
     GTGTGTCACT ATAACTAAAC GACCAATGCC ACTGGCATTC CGAACTACTT

1901 ACAACGCGGC GAGCTTTGAT CAACGACCTT TTGGAAACTT CGGCTTCCCC
     TGTTGCGCCG CTCGAAACTA GTTGCTGGAA AACCTTTGAA GCCGAAGGGG

1951 TGGAGAGAGC GAGATTCTCC GCGCTGTAGA AGTCACCATT GTTGTGCACG
     ACCTCTCTCG CTCTAAGAGG CGCGACATCT TCAGTGGTAA CAACACGTGC

2001 ACGACATCAT TCCGTGGCGT TATCCAGCTA AGCGCGAACT GCAATTTGGA
     TGCTGTAGTA AGGCACCGCA ATAGGTCGAT TCGCGCTTGA CGTTAARCCT

2051 GAATGGCAGC GCAATGACAT TCTTGCAGGT ATCTTCGAGC CAGCCACGAT
     CTTACCGTCG CGTTACTGTA AGAACGTCCA TAGAAGCTCG GTCGGTGCTA

2101 CGACATTGAT CTGGCTATCT TGCTGACAAA AGCAAGACAA CATAGCGTTG
     GCTGTAACTA GACCGATAGA ACGACTGTTT TCGTTCTCTT GTATCGCAAC

2151 CCTTGGTAGG TCCAGCGGCG GAGGAACTCT TTGATCCGGT TCCTGAACAG
     GGAACCATCC AGGTCGCCGC CTCCTTGAGA AACTAGGCCA AGGACTTGTC

2201 GATCTATTTG AGGCGCTAAA TGAAACCTTA ACGTATGGA ACTCGCCGCC
     CTAGATAAAC TCCGCGATTT ACTTTGGAAT TGCGATACCT TGAGCGGCGG

2251 CGACTGGGCT GGCGATGAGC GAAATGTAGT GCTTACGTTG TCCCGCATTT
     GCTGACCCGA CCGCTACTCG CTTTACATCA CGAATGCAAC AGGGCGTAAA

2301 GGTACAGCGC AGTAACCGGC AAAATCGCGC CGAAGGATGT CGCTGCCGAC
     CCATGTCGCG TCATTGGCCG TTTTAGCGCG GCTTCCTACA GCGACGGCTG

2351 TGGGCAATGG AGCGCCTGCC GGCCCAGTAT CAGCCCGTCA TACTTGAAGC
     ACCCGTTACC TCGCGGACGG CCGGGTCATA GTCGGGCAGT ATGAACTTCG

2401 TAGACAGGCT TATCTTGGAC AAGAAGAAGA TCGCTTGGCC TCGCGCGCAG
     ATCTGTCCGA ATAGAACCTG TTCTTCTTCT AGCGAACCGG AGCGCGCGTC

2451 ATCAGTTGGA AGAATTTGTC CACTACGTGA AAGGCGAGAT CACCAAGGTA
     TAGTCAACCT TCTTAAACAG GTGATGCACT TTCCGCTCTA GTGGTTCCAT

2501 GTCGGCAAAT AAATCTAAGC CGAATTGGGC CTAGTCTATA GGAGGTTTTG
     CAGCCGTTTA TTTAGATTCG GCTTAACCCG GATCAGATAT CCTCCAAAAC

2551 AAAAGAAAGG AGCAATAATC ATTTTCTTGT TCTATCAAGA GGGTGCTATT
     TTTTCTTTCC TCGTTATTAG TAAAAGAACA AGATAGTTCT CCCACGATAA

2601 GCTCCTTTCT TTTTTTCTTT TTATTTATTT ACTAGTATTT TACTTACATA
     CGAGGAAAGA AAAAAAGAAA AATAAATAAA TGATCATAAA ATGAATGTAT

2651 GACTTTTTTG TTTACATTAT AGAAAAAGAA GGAGAGGTTA TTTTCTTGCA
     CTGAAAAAAC AAATGTAATA TCTTTTTCTT CCTCTCCAAT AAAAGAACGT

2701 TTTATTCATG ATTGAGTATT CTATTTTGAT TTTGTATTTG TTTAAAATTG
     AAATAAGTAC TAACTCATAA GATAAACTA AAACATAAAC AAATTTTAAC

2751 TAGAAATAGA ACTTGTTTCT CTTCTTGCTA ATGTTACTAT ATCTTTTTGA
     ATCTTTATCT TGAACAAAGA GAAGAACGAT TACAATGATA TAGAAAAACT

2801 TTTTTTTTTT CCAAAAAAAA AATCAAATTT TGACTTCTTC TTATCTCTTA
     AAAAAAAAAA GGTTTTTTTT TTAGTTTAAA ACTGAAGAAG AATAGAGAAT

2851 TCTTTGAATA TCTCTTATCT TTGAAATAAT AATATCATTG AAATAAGAAA
     AGAAACTTAT AGAGAATAGA AACTTTATTA TTATAGTAAC TTTATTCTTT

2901 GAAGAGCTAT ATTCGAACTT GAATCTTTTG TTTTCTAATT TAAATAATGT
     CTTCTCGATA TAAGCTTGAA CTTAGAAAAC AAAAGATTAA ATTTATTACA

2951 AAAAACGGAA TGTAAGTAGG CGAGGGGGCG GATGTAGCCA AGTGGATCAA
     TTTTTGCCTT ACATTCATCC GCTCCCCCGC CTACATCGGT TCACCTAGTT

3001 GGCAGTGGAT TGTGAATCCA CCATGCGCGG GTTCAATTCC CGTCGTTCGC
     CCGTCACCTA ACACTTAGGT GGTACGCGCC CAAGTTAAGG GCAGCAAGCG
```

-continued

```
3051 CCATAATTAC TCCTATTTTT TTTTTTTTTG TAAAAACGAA GAATTTAATT
     GGTATTAATG AGGATAAAAA AAAAAAAAAC ATTTTTGCTT CTTAAATTAA

3101 CGATTTTCTC TCCTATTTAC TACGGCGACG AAGAATCAAA TTATCACTAT
     GCTAAAAGAG AGGATAAATG ATGCCGCTGC TTCTTAGTTT AATAGTGATA

3151 ATTTATTCCT TTTTCTACTT CTTCTTCCAA GTGCAGGATA ACCCCAAGGG
     TAAATAAGGA AAAAGATGAA GAAGAAGGTT CACGTCCTAT TGGGGTTCCC

3201 GTTGTGGGTT TTTTTCTACC AATTGGGGCT CTCCCTTCAC CACCCCCATG
     CAACACCCAA AAAAGATGG TTAACCCCGA GAGGGAAGTG GTGGGGGTAC

3251 GGGATGGTCT ACAGGGTTCA TAACTACTCC TCTTACTACA GGACGCTTAC
     CCCTACCAGA TGTCCCAAGT ATTGATGAGG AGAATGATGT CCTGCGAATG

3301 CTAGCCAACG CTTAGATCCG GCTCTACCCA AACTTTTCTG GTTCACCCCA
     GATCGGTTGC GAATCTAGGC CGAGATGGGT TTGAAAAGAC CAAGTGGGGT

3351 ACATTCCCCA CTTGTCCGAC TGTTGCTGAG CAGTTTTTGG ATATCAAACG
     TGTAAGGGGT GAACAGGCTG ACAACGACTC GTCAAAAACC TATAGTTTGC

3401 GACCTCCCCA GAAGGTAATT TTAATGTGGC CGATTTCCCC TCTTTTGCAA
     CTGGAGGGGT CTTCCATTAA AATTACACCG GCTAAAGGGG AGAAAACGTT

3451 TCAGTTTCGC TACAGCACCC GCTGCTCTAG CTAATTGTCC ACCCTTTCCA
     AGTCAAAGCG ATGTCGTGGG CGACGAGATC GATTAACAGG TGGGAAAGGT

3501 AGTGTGATTT CTATGTTATG TATGGCCGTG CCTAAGGGCA TATCGGTTGA
     TCACACTAAA GATACAATAC ATACCGGCAC GGATTCCCGT ATAGCCAACT

3551 AGTAGATTCT TCTTTTGATC AATCAAAACC CCTTCCCAAA CTGTACAAGC
     TCATCTAAGA AGAAAACTAG TTAGTTTTGG GGAAGGGTTT GACATGTTCG

3601 TTGGCGTAAT CATGGTCATA GCTGTTTCCT GTGTGAAATT GTTATCCGCT
     AACCGCATTA GTACCAGTAT CGACAAAGGA CACACTTTAA CAATAGGCGA

3651 CACAATTCCA CACAACATAC GAGCCGGAAG CATAAAGTGT AAAGCCTGGG
     GTGTTAAGGT GTGTTGTATG CTCGGCCTTC GTATTTCACA TTTCGGACCC

3701 GTGCCTAATG AGTGAGCTAA CTCACATTAA TTGCGTTGCG CTCACTGCCC
     CACGGATTAC TCACTCGATT GAGTGTAATT AACGCAACGC GAGTGACGGG

3751 GCTTTCCAGT CGGGAAACCT GTCGTGCCAG CTGCATTAAT GAATCGGCCA
     CGAAAGGTCA GCCCTTTGGA CAGCACGGTC GACGTAATTA CTTAGCCGGT

3801 ACGCGCGGGG AGAGGCGGTT TGCGTATTGG GCGCTCTTCC GCTTCCTCGC
     TGCGCGCCCC TCTCCGCCAA ACGCATAACC CGCGAGAAGG CGAAGGAGCG

3851 TCACTGACTC GCTGCGCTCG GTCGTTCGGC TGCGGCGAGC GGTATCAGCT
     AGTGACTGAG CGACGCGAGC CAGCAAGCCG ACGCCGCTCG CCATAGTCGA

3901 CACTCAAAGG CGGTAATACG GTTATCCACA GAATCAGGGG ATAACGCAGG
     GTGAGTTTCC GCCATTATGC CAATAGGTGT CTTAGTCCCC TATTGCGTCC

3951 AAAGAACATG TGAGCAAAAG GCCAGCAAAA GGCCAGGAAC CGTAAAAAGG
     TTTCTTGTAC ACTCGTTTTC CGGTCGTTTT CCGGTCCTTG GCATTTTTCC

4001 CCGCGTTGCT GGCGTTTTTC CATAGGCTCC GCCCCCCTGA CGAGCATCAC
     GGCGCAACGA CCGCAAAAAG GTATCCGAGG CGGGGGGACT GCTCGTAGTG

4051 AAAAATCGAC GCTCAAGTCA GAGGTGGCGA AACCCGACAG GACTATAAAG
     TTTTTAGCTG CGAGTTCAGT CTCCACCGCT TTGGGCTGTC CTGATATTTC

4101 ATACCAGGCG TTTCCCCCTG GAAGCTCCCT CGTGCGCTCT CCTGTTCCGA
     TATGGTCCGC AAAGGGGGAC CTTCGAGGGA GCACGCGAGA GGACAAGGCT

4151 CCCTGCCGCT TACCGGATAC CTGTCCGCCT TTCTCCCTTC GGGAAGCGTG
     GGGACGGCGA ATGGCCTATG GACAGGCGGA AAGAGGGAAG CCCTTCGCAC

4201 GCGCTTTCTC ATAGCTCACG CTGTAGGTAT CTCAGTTCGG TGTAGGTCGT
     CGCGAAAGAG TATCGAGTGC GACATCCATA GAGTCAAGCC ACATCCAGCA

4251 TCGCTCCARG CTGGGCTGTG TGCACGAACC CCCCGTTCAG CCCGACCGCT
     AGCGAGGTTC GACCCGACAC ACGTGCTTGG GGGGCAAGTC GGGCTGGCGA

4301 GCGCCTTATC CGGTAACTAT CGTCTTGAGT CCAACCCGGT AAGACACGAC
     CGCGGAATAG GCCATTGATA GCAGAACTCA GGTTGGGCCA TTCTGTGCTG

4351 TTATCGCCAC TGGCAGCAGC CACTGGTAAC AGGATTAGCA GAGCGAGGTA
     AATAGCGGTG ACCGTCGTCG GTGACCATTG TCCTAATCGT CTCGCTCCAT
```

-continued

```
4401 TGTAGGCGGT GCTACAGAGT TCTTGAAGTG GTGGCCTAAC TACGGCTACA
     ACATCCGCCA CGATGTCTCA AGAACTTCAC CACCGGATTG ATGCCGATGT

4451 CTAGAAGGAC AGTATTTGGT ATCTGCGCTC TGCTGAAGCC AGTTACCTTC
     GATCTTCCTG TCATAAACCA TAGACGCGAG ACGACTTCGG TCAATGGAAG

4501 GGAAARAGAG TTGGTAGCTC TTGATCCGGC AAACAAACCA CCGCTGGTAG
     CCTTTTTCTC AACCATCGAG AACTAGGCCG TTTGTTTGGT GGCGACCATC

4551 CGGTGGTTTT TTTGTTTGCA AGCAGCAGAT TACGCGCAGA AAAAAAGGAT
     GCCACCAAAA AAACAAACGT TCGTCGTCTA ATGCGCGTCT TTTTTTCCTA

4601 CTCAAGAAGA TCCTTTGATC TTTTCTACGG GGTCTGACGC TCAGTGGAAC
     GAGTTCTTCT AGGAAACTAG AAAAGATGCC CCAGACTGCG AGTCACCTTG

4651 GAAAACTCAC GTTAAGGGAT TTTGGTCATG AGATTATCAA AAAGGATCTT
     CTTTTGAGTG CAATTCCCTA AAACCAGTAC TCTAATAGTT TTTCCTAGAA

4701 CACCTAGATC CTTTTAAATT AAAAATGAAG TTTTAAATCA ATCTAAAGTA
     GTGGATCTAG GAAAATTTAR TTTTTACTTC AAAATTTAGT TAGATTTCAT

4751 TATATGAGTA AACTTGGTCT GACAGTTACC AATGCTTAAT CAGTGAGGCA
     ATATACTCAT TTGAACCAGA CTGTCAATGG TTACGAATTA GTCACTCCGT

4801 CCTATCTCAG CGATCTGTCT ATTTCGTTCA TCCATAGTTG CCTGACTCCC
     GGATAGAGTC GCTAGACAGA TAAAGCAAGT AGGTATCAAC GGACTGAGGG

4851 CGTCGTGTAG ATAACTACGA TACGGGAGGG CTTACCATCT GGCCCCAGTG
     GCAGCACATC TATTGATGCT ATGCCCTCCC GAATGGTAGA CCGGGGTCAC

4901 CTGCAATGAT ACCGCGAGAC CCACGCTCAC CGGCTCCAGA TTTATCAGCA
     GACGTTACTA TGGCGCTCTG GGTGCGAGTG GCCGAGGTCT AAATAGTCGT

4951 ATAAACCAGC CAGCCGGAAG GGCCGAGCGC AGAAGTGGTC CTGCAACTTT
     TATTTGGTCG GTCGGCCTTC CCGGCTCGCG TCTTCACCAG GACGTTGAAA

5001 ATCCGCCTCC ATCCAGTCTA TTAATTGTTG CCGGGAAGCT AGAGTAAGTA
     TAGGCGGAGG TAGGTCAGAT AATTAACAAC GGCCCTTCGA TCTCATTCAT

5051 GTTCGCCAGT TAATAGTTTG CGCAACGTTG TTGCCATTGC TACAGGCATC
     CAAGCGGTCA ATTATCAAAC GCGTTGCAAC AACGGTAACG ATGTCCGTAG

5101 GTGGTGTCAC GCTCGTCGTT TGGTATGGCT TCATTCAGCT CCGGTTCCCA
     CACCACAGTG CGAGCAGCAA ACCATACCGA AGTAAGTCGA GGCCAAGGGT

5151 ACGATCAAGG CGAGTTACAT GATCCCCCAT GTTGTGCAAA RAAGCGGTTA
     TGCTAGTTCC GCTCAATGTA CTAGGGGGTA CAACACGTTT TTTCGCCAAT

5201 GCTCCTTCGG TCCTCCGATC GTTGTCAGAA GTAAGTTGGC CGCAGTGTTA
     CGAGGAAGCC AGGAGGCTAG CAACAGTCTT CATTCAACCG GCGTCACAAT

5251 TCACTCATGG TTATGGCAGC ACTGCATAAT TCTCTTACTG TCATGCCATC
     AGTGAGTACC AATACCGTCG TGACGTATTA AGAGAATGAC AGTACGGTAG

5301 CGTAAGATGC TTTTCTGTGA CTGGTGAGTA CTCAACCAAG TCATTCTGAG
     GCATTCTACG AAAAGACACT GACCACTCAT GAGTTGGTTC AGTAAGACTC

5351 AATAGTGTAT GCGGCGACCG AGTTGCTCTT GCCCGGCGTC AATACGGGAT
     TTATCACATA CGCCGCTGGC TCAACGAGAA CGGGCCGCAG TTATGCCCTA

5401 AATACCGCGC CACATAGCAG AACTTTAAAA GTGCTCATCA TTGGAAAACG
     TTATGGCGCG GTGTATCGTC TTGAAATTTT CACGAGTAGT AACCTTTTGC

5451 TTCTTCGGGG CGAAAACTCT CAAGGATCTT ACCGCTGTTG AGATCCAGTT
     AAGAAGCCCC GCTTTTGAGA GTTCCTAGAA TGGCGACAAC TCTAGGTCAA

5501 CGATGTAACC CACTCGTGCA CCCAACTGAT CTTCAGCATC TTTTACTTTC
     GCTACATTGG GTGAGCACGT GGGTTGACTA GAAGTCGTAG AAAATGAAAG

5551 ACCAGCGTTT CTGGGTGAGC AAAAACAGGA AGGCAAAATG CCGCAAAAAA
     TGGTCGCAAA GACCCACTCG TTTTTGTCCT TCCGTTTTAC GGCGTTTTTT

5601 GGGAATAAGG GCGACACGGA AATGTTGAAT ACTCATACTC TTCCTTTTTC
     CCCTTATTCC CGCTGTGCCT TTACAACTTA TGAGTATGAG AAGGAAAAAG

5651 AATATTA
     TTATAAT
```

```
Sequence of p(CA)2
   1 AAGCATTTAT CAGGGTTATT GTCTCATGAG CGGATACATA TTTGAATGTA   (SEQ ID NO: 10)
     TTCGTAAATA GTCCCAATAA CAGAGTACTC GCCTATGTAT AAACTTACAT   (SEQ ID NO: 11)

51 TTTAGAAAAA TAAACAAATA GGGGTTCCGC GCACATTTCC CCGAAAAGTG
     AAATCTTTTT ATTTGTTTAT CCCCAAGGCG CGTGTAAAGG GGCTTTTCAC

101 CCACCTGACG TCTAAGAAAC CATTATTATC ATGACATTAA CCTATAAAAA
     GGTGGACTGC AGATTCTTTG GTRATAATAG TACTGTAATT GGATATTTTT

151 TAGGCGTATC ACGAGGCCCT TTCGTCTCGC GCGTTTCGGT GATGACGGTG
     ATCCGCATAG TGCTCCGGGA AAGCAGAGCG CGCAAAGCCA CTACTGCCAC

201 RAAACCTCTG ACACATGCAG CTCCCGGAGA CGGTCACAGC TTGTCTGTAA
     TTTTGGAGAC TGTGTACGTC GAGGGCCTCT GCCAGTGTCG AACAGACATT

251 GCGGATGCCG GGAGCAGACA AGCCCGTCAG GGCGCGTCAG CGGGTGTTGG
     CGCCTACGGC CCTCGTCTGT TCGGGCAGTC CCGCGCAGTC GCCCACAACC

301 CGGGTGTCGG GGCTGGCTTA ACTATGCGGC ATCAGAGCAG ATTGTACTGA
     GCCCACAGCC CCGACCGAAT TGATACGCCG TAGTCTCGTC TAACATGACT

351 GAGTGCACCA TATGCGGTGT GAAATACCGC ACAGATGCGT AAGGAGAAAA
     CTCACGTGGT ATACGCCACA CTTTATGGCG TGTCTACGCA TTCCTCTTTT

401 TACCGCATCA GGCGCCATTC GCCATTCAGG CTGCGCAACT GTTGGGAAGG
     ATGGCGTAGT CCGCGGTAAG CGGTAAGTCC GACGCGTTGA CAACCCTTCC

451 GCGATCGGTG CGGGCCTCTT CGCTATTACG CCAGCTGGCG AAAGGGGGAT
     CGCTAGCCAC GCCCGGAGAA GCGATAATGC GGTCGACCGC TTTCCCCCTA

501 GTGCTGCAAG GCGATTAAGT TGGGTAACGC CAGGGTTTTC CCAGTCACGA
     CACGACGTTC CGCTAATTCA ACCCATTGCG GTCCCAAAAG GGTCAGTGCT

551 CGTTGTAAAA CGACGGCCAG TGAATTCATG ACTGCAATTT TAGAGAGACG
     GCAACATTTT GCTGCCGGTC ACTTAAGTAC TGACGTTAAA ATCTCTCTGC

601 CGAAAGCGAA AGCCTATGGG GTCGCTTCTG TAACTGGATA ACTAGCACTG
     GCTTTCGCTT TCGGATACCC CAGCGAAGAC ATTGACCTAT TGATCGTGAC

651 AAAACCGTCT TTACATTGGA TGGTTTGGTG TTTTGATGAT CCCTACCTTA
     TTTTGGCAGA AATGTAACCT ACCAAACCAC AAAACTACTA GGGATGGAAT

701 TTGACGGCAA CTTCTGTATT TATTATTGCC TTCATTGCTG CTCCTCCAGT
     AACTGCCGTT GAAGACATAA ATAATAACGG AAGTAACGAC GAGGAGGTCA

751 AGACATTGAT GGTATTCGTG AACCTGTTTC AGGGTCTCTA CTTTACGGAA
     TCTGTAACTA CCATAAGCAC TTGGACAAAG TCCCAGAGAT GAAATGCCTT

801 ACAATATTAT TTCCGGTGCC ATTATTCCTA CTTCTGCAGC TATAGGTTTA
     TGTTATAATA AAGGCCACGG TAATAAGGAT GAAGACGTCG ATATCCAAAT

851 CATTATTATC CAATCTGGGA AGCGGCATCC GTTGATGAAT GGTTATACAA
     GTAAAAATGG GTTAGACCCT TCGCCGTAGG CAACTACTTA CCAATATGTT

901 CGGTGGTCCT TATGAACTAA TTGTTCTACA CTTCTTACTT GGCGTAGCTT
     GCCACCAGGA ATACTTGATT AACAAGATGT GAAGAATGAA CCGCATCGAA

951 GTTACATGGG TCGTGAGTGG GAGCTTAGTT TCCGTCTGGG TATGCGACCT
     CAATGTACCC AGCACTCACC CTCGAATCAA AGGCAGACCC ATACGCTGGA

1001 TGGATTGCTG TTGCATATTC AGCTCCTGTT GCAGCTGCTA CCGCAGTTTT
     ACCTAACGAC AACGTATAAG TCGAGGACAA CGTCGACGAT GGCGTCAAAA

1051 CTTGATCTAC CCAATTGGTC AAGGAAGTTT TTCTGATGGT ATGCCTCTAG
     GAACTAGATG GGTTAACCAG TTCCTTCAAA AGACTACCA TACGGAGATC

1101 GAATCTCTGG TACTTTCART TTCATGATTG TATTCCAGGC TGAGCACAAC
     CTTAGAGACC ATGAAAGTTA AAGTACTAAC ATAAGGTCCG ACTCGTGTTG

1151 ATCCTTATGC ACCCATTTCA CATGTTAGGC GTAGCTGGTG TATTCGGCGG
     TAGGAATACG TGGGTAAAGT GTACAATCCG CATCGACCAC ATAAGCCGCC

1201 CTCCCTATTC AGTGCTATGC ATGGTTCCTT GGTAACTTCT AGTTTGATCA
     GAGGGATAAG TCACGATACG TACCAAGGAA CCATTGAAGA TCAAACTAGT

1251 GGGAAACCAC AGAAAATGAA TCTGCTAATG AAGGTTACAG ATTCGGTCAA
     CCCTTTGGTG TCTTTTACTT AGACGATTAC TTCCAATGTC TAAGCCAGTT
```

```
1301 GAGGAAGAAA CTTATAACAT CGTAGCCGCT CATGGTTATT TTGGCCGATT
     CTCCTTCTTT GAATATTGTA GCATCGGCGA GTACCAATAA AACCGGCTAA

1351 GATCTTCCAA TATGCTAGTT TCAACAACTC TCGTTCGTTA CACTTCTTCC
     CTAGAAGGTT ATACGATCAA AGTTGTTGAG AGCAAGCAAT GTGAAGAAGG

1401 TAGCTGCTTG GCCTGTAGTA GGTATCTGGT TTACCGCTTT AGGTATCAGC
     ATCGACGAAC CGGACATCAT CCATAGACCA AATGGCGAAR TCCATAGTCG

1451 ACTATGGCTT TCAACCTAAA TGGTTTCAAT TCAACCAAT CTGTAGTTGA
     TGATACCGAA AGTTGGATTT ACCAAAGTTA AAGTTGGTTA GACATCAACT

1501 CAGTCAAGGC CGTGTAATTA ATACTTGGGC TGATATCATT AACCGTGCTA
     GTCAGTTCCG GCACATTAAT TATGAACCCG ACTATAGTAA TTGGCACGAT

1551 ACCTTGGTAT GGAAGTTATG CATGAACGTA ATGCTCACAA CTTCCCTCTA
     TGGAACCATA CCTTCAATAC GTACTTGCAT TACGAGTGTT GAAGGGAGAT

1601 GACCTAGCTG CTATCGAAGC TCCATCTACA AATGGATAAG TCGACGGTAT
     CTGGATCGAC GATAGCTTCG AGGTAGATGT TTACCTATTC AGCTGCCATA

1651 CGATAAGCTT CCCCGGGAGA CCACAACGGT TCCCTCTAG AAATAATTTT
     GCTATTCGAA GGGGCCCTCT GGTGTTGCCA AGGGAGATC TTTATTAAAA

1701 GTTTAACTTT AAGAAGGAGA TGTACTACTG AACCCGAACT CATTTCAATT
     CAAATTGAAA TTCTTCCTCT ATATGATGAC TTGGGCTTGA GTAAAGTTAA

1751 CAAAGAAAAC ATACTACAAT TTTTTTCTGT ACATGATGAC ATCTGGAAAA
     GTTTCTTTTG TATGATGTTA AAAAAGACA TGTACTACTG TAGACCTTTT

1801 AATTACAAGA ATTTTATTAT GGGCAAAGCC CAATTAATGA GGCTTTGGCG
     TTAATGTTCT TAAAATAATA CCCGTTTCGG GTTAATTACT CCGAAACCGC

1851 CAGCTCAACA AGAAGATAT GTCTTTGTTC TTTGAAGCAC TATCTAAAAA
     GTCGAGTTGT TCTTCTATA CAGAAACAAG AAACTTCGTG ATAGATTTTT

1901 CCCAGCTCGC ATGATGGAAA TGCAATGGAG CTGGTGGCAA GGTCAAATAC
     GGGTCGAGCG TACTACCTTT ACGTTACCTC GACCACCGTT CCAGTTTATG

1951 AAATCTACCA AAATGTGTTG ATGCGCAGCG TGGCCAAAGA TGTAGCACCA
     TTTAGATGGT TTTACACAAC TACGCGTCGC ACCGGTTTCT ACATCGTGGT

2001 TTTATTCAGC CTGAAAGTGG TGATCGTCGT TTTAACAGCC CATTATGGCA
     AAATAAGTCG GACTTTCACC ACTAGCAGCA AAATTGTCGG GTAATACCGT

2051 AGAACACCCA AATTTTGACT TGTTGTCACA GTCTTATTTA CTGTTTAGCC
     TCTTQTGGGT TTAAAACTGA ACAACAGTGT CAGAATAAAT GACAAATCGG

2101 AGTTAGTGCA AAACATGGTA GATGTGGTCG AAGGTGTTCC AGACAAAGTT
     TCAATCACGT TTTGTACCAT CTACACCAGC TTCCACAAGG TCTGTTTCAA

2151 CGCTATCGTA TTCACTTCTT TACCCGCCAA ATGATCAATG CGTTATCTCC
     GCGATAGCAT AAGTGAAGAA ATGGGCGGTT TACTAGTTAC GCAATAGAGG

2201 AAGTAACTTT CTGTGGACTA ACCCAGAAGT GATTCAGCAA ACTGTAGCTG
     TTCATTGAAA GACACCTGAT TGGGTCTTCA CTAAGTCGTT TGACATCGAC

2251 AACAAGGTGA AAACTTAGTC CGTGGCATGC AAGTTTTCCA TGATGATGTC
     TTCTTCCTCT TTTGAATCAG GCACCGTACG TACACAAGGT ACTACTACAG

2301 ATGAATAGCG GCAAGTATTT ATCTATTCGC ATGGTGAATA GCGACTCTTT
     TACTTATCGC CGTTCATAAA TAGATAAGCG TACCACTTAT CGCTGAGAAA

2351 CAGCTTGGGC AAAGATTTAG CTTACACCCC TGGTGCAGTC GTCTTTGAAA
     GTCGAACCCG TTTCTAAATC GAATGTGGGG ACCACGTCAG CAGAAACTTT

2401 ATGACATTTT CCAATTATTG CAATATGAAG CAACTACTGA AAATGTGTAT
     TACTGTAAAA GGTTAATAAC GTTATACTTC GTTGATGACT TTTACACATA

2451 CAAACCCCTA TTCTAGTCGT ACCACCGTTT ATCRATAAAT ATTATGTGCT
     GTTTGGGGAT AAGATCAGCA TGGTGGCAAA TAGTTATTTA TAATACACGA

2501 GGATTTACGC GAACAAAACT CTTTAGTGAA CTGGTTGCGC CAGCAAGGTC
     CCTAAATGCG CTTGTTTTGA GAAATCACTT GACCAACGCG GTCGTTCCAG

2551 ATACAGTCTT TTTAATGTCA TGGCGTAACC CAAATGCCGA ACAGAAAGAA
     TATGTCAGAA AAATTACAGT ACCGCATTGG GTTTACGGCT TGTCTTTCTT

2601 TTGACTTTTG CCGATCTCAT TACACAAGGT TCAGTGGAAG CTTTGCGTGT
     AACTGAAAAC GGCTAGAGTA ATGTGTTCCA AGTCACCTTC GAAACGCACA
```

-continued

```
2651 AATTGAAGAA ATTACCGGTG AAAAAGAGGC CAACTGCATT GGCTACTGTA
     TTAACTTCTT TAATGGCCAC TTTTTCTCCG GTTGACGTAA CCGATGACAT

2701 TTGGTGGTAC GTTACTTGCT GCGACTCAAG CCTATTACGT GGCAAAACGC
     AACCACCATG CAATGAACGA CGCTGAGTTC GGATAATGCA CCGTTTTGCG

2751 CTGAAAAATC ACGTAAAGTC TGCGACCTAT ATGGCCACCA TTATCGACTT
     GACTTTTTAG TGCATTTCAG ACGCTGGATA TACCGGTGGT AATAGCTGAA

2801 TGAAAACCCA GGCAGCTTAG GTGTATTTAT TAATGAACCT GTAGTGAGCG
     ACTTTTGGGT CCGTCGAATC CACATAAATA ATTACTTGGA CATCACTCGC

2851 GTTTAGAAAA CCTGAACAAT CAATTGGGTT ATTTCGATGG TCGTCAGTTG
     CAAATCTTTT GGACTTGTTA GTTAACCCAA TAAAGCTACC AGCAGTCAAC

2901 GCAGTTACCT TCAGTTTACT GCGTGAAAAT ACGCTGTACT GGAATTACTA
     CGTCAATGGA AGTCAAATGA CGCACTTTTA TGCGACATGA CCTTAATGAT

2951 CATCGACAAC TACTTAAAAG GTAAAGAACC TTCTGATTTT GATATTTTAT
     GTAGCTGTTG ATGAATTTTC CATTTCTTGG AAGACTAAAA CTATAAAATA

3001 ATTGGAACAG CGATGGTACG AATATCCCTG CCAAAATTCA TAATTTCTTA
     TAACCTTGTC GCTACCATGC TTATAGGGAC GGTTTTAAGT ATTAAAGAAT

3051 TTGCGCAATT TGTATTTGAA CAATGAATTG ATTTCACCAA ATGCCGTTAA
     AACGCGTTAA ACATAAACTT GTTACTTAAC TAAAGTGGTT TACGGCAATT

3101 GGTTAACGGT GTGGGCTTGA ATCTATCTCG TGCTAAAGAA CCAAGCTTCT
     CCAATTGCCA CACCCGAACT TAGATAGAGC ACATTTTGT GGTTCGAAGA

3151 TTATTGCGAC GCAGGAAGAC CATATCGCAC TTTGGGATAC TTGTTTCCGT
     AATAACGCTG CGTCCTTCTG GTATAGCGTG AAACCCTATG AACAAAGGCA

3201 GGCGCAGATT ACTTGGGTGG TGAATCAACC TTGGTTTTAG GTGAATCTGG
     CCGCGTCTAA TGAACCCACC ACTTAGTTGG AACCAAAATC CACTTAGACC

3251 ACACGTAGCA GGTATTGTCA ATCCTCCAAG CCGTAATAAA TACGGTTGCT
     TGTGCATCGT CCATAACAGT TAGGAGGTTC GGCATTATTT ATGCCAACGA

3301 ACACCAATGC TGCCAAGTTT GAAAATACCA ACAATGGCT AGATGGCGCA
     TGTGGTTACG ACGGTTCAAA CTTTTATGGT TTGTTACCGA TCTACCGCGT

3351 GAATATCACC CTGAATCTTG GTGGTTGCGC TGGCAGGCAT GGGTCACACC
     CTTATAGTGG GACTTAGAAC CACCAACGCG ACCGTCCGTA CCCAGTGTGG

3401 GTACACTGGT GAACAAGTCC CTGCCCGCAA CTTGGGTAAT GCGCAGTATC
     CATGTGACCA CTTGTTCAGG GACGGGCGTT GAACCCATTA CGCGTCATAG

3451 CAAGCATTGA AGCGGCACCG GGTCGCTATG TTTTGGTAAA TTTATTCTAA
     GTTCGTAACT TCGCCGTGGC CCAGCGATAC AAAACCATTT AAATAAGATT

3501 GCGGCCGCCA CCGCGGTGGA GCTCAATAAA AAAATCTAG ATGCTTATGA
     CGCCGGCGGT GGCGCCACCT CGAGTTATTT TTTTTAGATC TACGAATACT

3551 TTCAGTAGTA GGAGGCAAAC CATATGAAAG ATGTTGTGAT TGTTGCAGCA
     AAGTCATCAT CCTCCGTTTG GTATACTTTC TACAACACTA ACAACGTCGT

3601 AAACGTACTG CGATTGGTAG CTTTTTAGGT AGTCTTGCAT CTTTATCTGC
     TTTGCATGAC GCTAACCATC GAAAAATCCA TCAGAACGTA GAAATAGACG

3651 ACCACAGTTG GGGCAAACAG CAATTCGTGC AGTTTTAGAC AGCGCTAATG
     TGGTGTCAAC CCCGTTTGTC GTTAAGCACG TCAAAATCTG TCGCGATTAC

3701 TAAAACCTGA ACAAGTTGAT CAGGTGATTA TGGGCAACGT ACTCACGACA
     ATTTTGGACT TGTTCAACTA GTCCACTAAT ACCCGTTGCA TGAGTGCTGT

3751 GGCGTGGGAC AAAACCCTGC ACGTCAGGCA GCAATTGCTG CTGGTATTCC
     CCGCACCCTG TTTTGGGACG TGCAGTCCGT CGTTAACGAC GACCATAAGG

3801 AGTACAAGTG CCTGCATCTA CGCTGAATGT CGTCTGTGGT TCAGGTTTGC
     TCATGTTCAC GGACGTAGAT GCGACTTACA GCAGACACCA AGTCCAAACG

3851 GTGCGGTACA TTTGGCAGCA CAAGCCATTC AATGCGATGA AGCCGACATT
     CACGCCATGT AAACCGTCGT GTTCGGTAAG TTACGCTACT TCGGCTGTAA

3901 GTGGTCGCAG GTGGTCAAGA ATCTATGTCA CAAAGTGCGC ACTATATGCA
     CACCAGCGTC CACCAGTTCT TAGATACAGT GTTTCACGCG TGATATACGT

3951 GCTGCGTAAT GGGCAAAAAA TGGGTAATGC ACAATTGGTG GATAGCATGG
     CGACGCATTA CCCGTTTTTT ACCCATTACG TGTTAACCAC CTATCGTACC
```

-continued

```
4001 TGGCTGATGG TTTAACCGAT GCCTATAACC AGTATCAAAT GGGTATTACC
     ACCGACTACC AAATTGGCTA CGGATATTGG TCATAGTTTA CCCATAATGG

4051 GCAGAAAATA TTGTAGAAAA ACTGGGTTTA AACCGTGAAG AACAAGATCA
     CGTCTTTTAT AACATCTTTT TGACCCAAAT TTGGCACTTC TTGTTCTAGT

4101 ACTTGCATTG ACTTCACAAC AACGTGCTGC GGCAGCTCAG GCAGCTGGCA
     TGAACGTAAC TGAAGTGTTG TTGCACGACG CCGTCGAGTC CGTCGACCGT

4151 AGTTTAAAGA TGAAATTGCC GTAGTCAGCA TTCCACAACG TAAAGGTGAG
     TCAAATTTCT ACTTTAACGG CATCAGTCGT AAGGTGTTGC ATTTCCACTC

4201 CCTGTTGTAT TTGCTGAAGA TGAATACATT AAAGCCAATA CCAGCCTTGA
     GGACAACATA AACGACTTCT ACTTATGTAA TTTCGGTTAT GGTCGGAACT

4251 AAGCCTCACA AAACTACGCC CAGCCTTTAA AAAAGATGGT AGCGTAACCG
     TTCGGAGTGT TTTGATGCGG GTCGGAAATT TTTTCTACCA TCGCATTGGC

4301 CAGGTAATGC TTCAGGCATT AATGATGGTG CAGCAGCAGT ACTGATGATG
     GTCCATTACG AAGTCCGTAA TTACTACCAC GTCGTCGTCA TGACTACTAC

4351 AGTGCGGACA AAGCAGCAGA ATTAGGTCTT AAGCCATTGG CACGTATTAA
     TCACGCCTGT TTCGTCGTCT TAATCCAGAA TTCGGTAACC GTGCATAATT

4401 AGGCTATGCC ATGTCTGGTA TTGAGCCTGA AATTATGGGG CTTGGTCCTG
     TCCGATACGG TACAGACCAT AACTCGGACT TTAATACCCC GAACCAGGAC

4451 TCGATGCAGT AAAGAAAACC CTCAACAAAG CAGGCTGGAG CTTAGATCAG
     AGCTACGTCA TTTCTTTTGG GAGTTGTTTC GTCCGACCTC GAATCTAGTC

4501 GTTGATTTGA TTGAAGCCAA TGAAGCATTT GCTGCACAGG CTTTGGGTGT
     CAACTAAACT AACTTCGGTT ACTTCGTAAA CGACGTGTCC GAAACCCACA

4551 TGCTAAAGAA TTAGGCTTAG ACCTGGATAA AGTCAACGTC AATGGCGGTG
     ACGATTTCTT AATCCGAATC TGGACCTATT TCAGTTGCAG TTACCGCCAC

4601 CAATTGCATT GGGTCACCCA ATTGGGGCTT CAGGTTGCCG TATTTTGGTG
     GTTAACGTAA CCCAGTGGGT TAACCCCGAA GTCCAACGGC ATAAAACCAC

4651 ACTTTATTAC ATGAAATGCA GCGCCGTGAT GCCAAGAAAG GCATTGCAAC
     TGAAATAATG TACTTTACGT CGCGGCACTA CGGTTCTTTC CGTAACGTTG

4701 CCTCTGTGTT GGCGGTGGTA TGGGTGTTGC ACTTGCAGTT GAACGTGACT
     GGAGACACAA CCGCCACCAT ACCCACAACG TGAACGTCAA CTTGCACTGA

4751 AAGCGGCCGC TCGAGTTTGG ATCCAATCGA TACAAGTGAG TTGTAGGGAG
     TTCGCCGGCG AGCTCAAACC TAGGTTAGCT ATGTTCACTC AACATCCCTC

4801 GCAACCATGG CAGAAGCGGT GATCGCCGAA GTATCGACTC AACTATCAGA
     CGTTGGTACC GTCTTCGCCA CTAGCGGCTT CATAGCTGAG TTGATAGTCT

4851 GGTAGTTGGC GTCATCGAGC GCCATCTCGA ACCGACGTTG CTGGCCGTAC
     CCATCAACCG CAGTAGCTCG CGGTAGAGCT TGGCTGCAAC GACCGGCATG

4901 ATTTGTACGG CTCCGCAGTG GATGGCGGCC TGAAGCCACA CAGTGATATT
     TAAACATGCC GAGGCGTCAC CTACCGCCGG ACTTCGGTGT GTCACTATAA

4951 GATTTGCTGG TTACGGTGAC CGTAAGGCTT GATGAAACAA CGCGGCGAGC
     CTAAACGACC AATGCCACTG GCATTCCGAA CTACTTTGTT GCGCCGCTCG

5001 TTTGATCAAC GACCTTTTGG AAACTTCGGC TTCCCCTGGA GAGAGCGAGA
     AAACTAGTTG CTGGAAAACC TTTGAAGCCG AAGGGGACCT CTCTCGCTCT

5051 TTCTCCGCGC TGTAGAAGTC ACCATTGTTG TGCACGACGA CATCATTCCG
     AAGAGGCGCG ACATCTTCAG TGGTAACAAC ACGTGCTGCT GTAGTAAGGC

5101 TGGCGTTATC CAGCTAAGCG CGAACTGCAA TTTGGAGAAT GGCAGCGCAA
     ACCGCAATAG GTCGATTCGC GCTTGACGTT AAACCTCTTA CCGTCGCGTT

5151 TGACATTCTT GCAGGTATCT TCGAGCCAGC CACGATCGAC ATTGATCTGG
     ACTGTAAGAA CGTCCATAGA AGCTCGGTCG GTGCTAGCTG TAACTAGACC

5201 CTATCTTGCT GACAAAAGCA AGAGAACATA GCGTTGCCTT GGTAGGTCCA
     GATAGAACGA CTGTTTTCGT TCTCTTGTAT CGCAACGGAA CCATCCAGGT

5251 GCGGCGGAGG AACTCTTTGA TCCGGTTCCT GAACAGGATC TATTTGAGGC
     CGCCGCCTCC TTGAGAAACT AGGCCAAGGA CTTGTCCTAG ATAAACTCCG

5301 GCTAAATGAA ACCTTAACGC TATGGAACTC GCCGCCCGAC TGGGCTGGCG
     CGATTTACTT TGGAATTGCG ATACCTTGAG CGGCGGGCTG ACCCGACCGC
```

```
-continued

5351 ATGAGCGAAA TGTAGTGCTT ACGTTGTCCC GCATTTGGTA CAGCGCAGTA
     TACTCGCTTT ACATCACGAA TGCAACAGGG CGTAAACCAT GTCGCGTCAT

5401 ACCGGCAAAA TCGCGCCGAA GGATGTCGCT GCCGACTGGG CAATGGAGCG
     TGGCCGTTTT AGCGCGGCTT CCTACAGCGA CGGCTGACCC GTTACCTCGC

5451 CCTGCCGGCC CAGTATCAGC CCGTCATACT TGAAGCCACA CAGGCTTATC
     GGACGGCCGG GTCATAGTCG GGCAGTATGA ACTTCGATCT GTCCGAATAG

5501 TTGGACAAGA AGAAGATCGC TTGGCCTCGC GCGCAGATCA GTTGGAAGAA
     AACCTGTTCT TCTTCTAGCG AACCGGAGCG CGCGTCTAGT CAACCTTCTT

5551 TTTGTCCACT ACGTGAAAGG CGAGATCACC AAGGTAGTCG GCAAATAAAT
     AAACAGGTGA TGCACTTTCC GCTCTAGTGG TTCCATCAGC CGTTTATTTA

5601 CTAAGCCGAA TTGGGCCTAG TCTATAGGAG GTTTTGAAAA GAAAGGAGCA
     GATTCGGCTT AACCCGGATC AGATATCCTC CAAAACTTTT CTTTCCTCGT

5651 ATAATCATTT TCTTGTTCTA TCAAGAGGGT GCTATTGCTC CTTTCTTTTT
     TATTAGTAAA AGAACAAGAT AGTTCTCCCA CGATAACGAG GAAAGAAAAA

5701 TTCTTTTTAT TTATTTACTA GTATTTTACT TACATAGACT TTTTTGTTTA
     AAGAAAAATA AATAAATGAT CATAAAATGA ATGTATCTGA AAAAACAAAT

5751 CATTATAGAA AAAGAAGGAG AGGTTATTTT CTTGCATTTA TTCATGATTG
     GTAATATCTT TTTCTTCCTC TCCAATAAAA GAACGTAAAT AAGTACTAAC

5801 AGTATTCTAT TTTGATTTTG TATTTGTTTA AAATTGTAGA AATAGAACTT
     TCATAAGATA AAACTAAAAC ATAAACAAAT TTTAACATCT TTATCTTTGA

5851 GTTTCTCTTC TTGCTAATGT TACTATATCT TTTTGATTTT TTTTTTCCAA
     CAAAGAGAAG AACGATTACA ATGATATAGA AAAACTAAAA AAAAAAGGTT

5901 AAAAAAAATC AAATTTTGAC TTCTTCTTAT CTCTTATCTT TGAATATCTC
     TTTTTTTTAG TTTAAAACTG AAGAAGAATA GAGAATAGAA ACTTATAGAG

5951 TTATCTTTGA AATAATAATA TCATTGAAAT AAGAAAGAAG AGCTATATTC
     AATAGAAACT TTATTATTAT AGTAACTTTA TTCTTTCTTC TCGATATAAG

6001 GAACTTGAAT CTTTTGTTTT CTAATTTAAA TAATGTAAAA ACGGAATGTA
     CTTGAACTTA GAAAACAAAA GATTAAATTT ATTACATTTT TGCCTTACAT

6051 AGTAGGCGAG GGGGCGGATG TAGCCAAGTG GATCAAGGCA GTGGATTGTG
     TCATCCGCTC CCCCGCCTAC ATCGGTTCAC CTAGTTCCGT CACCTAACAC

6101 AATCCACCAT GCGCGGGTTC AATTCCCGTC GTTCGCCCAT AATTACTCCT
     TTAGGTGGTA CGCGCCCAAG TTAAGGGCAG CAAGCGGGTA TTAATGAGGA

6151 ATTTTTTTTT TTTTTGTAAA AACGAAGAAT TTAATTCGAT TTTCTCTCCT
     TAAAAAAAAA AAAAACATTT TTGCTTCTTA AATTAAGCTA AAAGAGAGGA

6201 ATTTACTACG GCGACGAAGA ATCAAATTAT CACTATATTT ATTCCTTTTT
     TAAATGATGC CGCTGCTTCT TAGTTTAATA GTGATATAAA TAAGGAAAAA

6251 CTACTTCTTC TTCCAAGTGC AGGATAACCC CAAGGGGTTG TGGGTTTTTT
     GATGAAGAAG AAGGTTCACG TCCTATTGGG GTTCCCCAAC ACCCAAAAAA

6301 TCTACCAATT GGGGCTCTCC CTTCACCACC CCCATGGGGA TGGTCTACAG
     AGATGGTTAA CCCCGAGAGG GAAGTGGTGG GGGTACCCCT ACCAGATGTC

6351 GGTTCATAAC TACTCCTCTT ACTACAGGAC GCTTACCTAG CCAACGCTTA
     CCAAGTATTG ATGAGGAGAA TGATGTCCTG CGAATGGATC GGTTGCGAAT

6401 GATCCGGCTC TACCCAAACT TTTCTGGTTC ACCCCAACAT TCCCCACTTG
     CTAGGCCGAG ATGGGTTTGA AAAGACCAAG TGGGGTTGTA AGGGGTGAAC

6451 TCCGACTGTT GCTGAGCAGT TTTTGGATAT CAAACGGACC TCCCCAGAAG
     AGGCTGACAA CGACTCGTCA AAAACCTATA GTTTGCCTGG AGGGGTCTTC

6501 GTAATTTTAA TGTGGCCGAT TTCCCCTCTT TTGCAATCAG TTTCGCTACA
     CATTAAAATT ACACCGGCTA AAGGGGAGAA AACGTTAGTC AAAGCGATGT

6551 GCACCCGCTG CTCTAGCTAA TTGTCCACCC TTTCCAAGTG TGATTTCTAT
     CGTGGGCGAC GAGATCGATT AACAGGTGGG AAAGGTTCAC ACTAAAGATA

6601 GTTATGTATG GCCGTGCCTA AGGGCATATC GGTTGAAGTA GATTCTTCTT
     CAATACATAC CGGCACGGAT TCCCGTATAG CCAACTTCAT CTAAGAAGAA

6651 TTGATCAATC AAAACCCCTT CCCAAACTGT ACAAGCTTGG CGTAATCATG
     AACTAGTTAG TTTTGGGGAA GGGTTTGACA TGTTCGAACC GCATTAGTAC
```

-continued

```
6701 GTCATAGCTG TTTCCTGTGT GAAATTGTTA TCCGCTCACA ATTCCACACA
     CAGTATCGAC AAAGGACACA CTTTAACAAT AGGCGAGTGT TAAGGTGTGT

6751 ACATACGAGC CGGAAGCATA AAGTGTAAAG CCTGGGGTGC CTAATGAGTG
     TGTATGCTCG GCCTTCGTAT TTCACATTTC GGACCCCACG GATTACTCAC

6801 AGCTAACTCA CATTAATTGC GTTGCGCTCA CTGCCCGCTT TCCAGTCGGG
     TCGATTGAGT GTAATTAACG CAACGCGAGT GACGGGCGAA AGGTCAGCCC

6851 AAACCTGTCG TGCCAGCTGC ATTAATGAAT CGGCCAACGC GCGGGGAGAG
     TTTGGACAGC ACGGTCGACG TAATTACTTA GCCGGTTGCG CGCCCCTCTC

6901 GCGGTTTGCG TATTGGGCGC TCTTCCGCTT CCTCGCTCAC TGACTCGCTG
     CGCCAAACGC ATAACCCGCG AGAAGGCGAA GGAGCGAGTG ACTGAGCGAC

6951 CGCTCGGTCG TTCGGCTGCG GCGAGCGGTA TCAGCTCACT CAAAGGCGGT
     GCGAGCCAGC AAGCCGACGC CGCTCGCCAT AGTCGAGTGA GTTTCCGCCA

7001 AATACGGTTA TCCACAGAAT CAGGGGATAA CGCAGGAAAG AACATGTGAG
     TTATGCCAAT AGGTGTCTTA GTCCCCTATT GCGTCCTTTC TTGTACACTC

7051 CAAAAGGCCA GCAAAAGGCC AGGAACCGTA AAAAGGCCGC GTTGCTGGCG
     GTTTTCCGGT CGTTTTCCGG TCCTTGGCAT TTTTCCGGCG CAACGACCGC

7101 TTTTTCCATA GGCTCCGCCC CCCTGACGAG CATCACAAAA ATCGACGCTC
     AAAAAGGTAT CCGAGGCGGG GGGACTGCTC GTAGTGTTTT TAGCTGCGAG

7151 AAGTCAGAGG TGGCGAAACC CGACAGGACT ATAAAGATAC CAGGCGTTTC
     TTCAGTCTCC ACCGCTTTGG GCTGTCCTGA TATTTCTATG GTCCGCAAAG

7201 CCCCTGGAAG CTCCCTCGTG CGCTCTCCTG TTCCGACCCT GCCGCTTACC
     GGGGACCTTC GAGGGAGCAC GCGAGAGGAC AAGGCTGGGA CGGCGAATGG

7251 GGATACCTGT CCGCCTTTCT CCCTTCGGGA AGCGTGGCGC TTTCTCATAG
     CCTATGGACA GGCGGAAAGA GGGAAGCCCT TCGCACCGCG AAAGAGTATC

7301 CTCACGCTGT AGGTATCTCA GTTCGGTGTA GGTCGTTCGC TCCAAGCTGG
     GAGTGCGACA TCCATAGAGT CAAGCCACAT CCAGCAAGCG AGGTTCGACC

7351 GCTGTGTGCA CGAACCCCCC GTTCAGCCCG ACCGCTGCGC CTTATCCGGT
     CGACACACGT GCTTGGGGGG CAAGTCGGGC TGGCGACGCG GAATAGGCCA

7401 AACTATCGTC TTGAGTCCAA CCCGGTAAGA CACGACTTAT CGCCACTGGC
     TTGATAGCAG AACTCAGGTT GGGCCATTCT GTGCTGAATA GCGGTGACCG

7451 AGCAGCCACT GGTAACAGGA TTAGCAGAGC GAGGTATGTA GGCGGTGCTA
     TCGTCGGTGA CCATTGTCCT AATCGTCTCG CTCCATACAT CCGCCACGAT

7501 CAGAGTTCTT GAAGTGGTGG CCTAACTACG GCTACACTAG AAGGACAGTA
     GTCTCAAGAA CTTCACCACC GGATTGATGC CGATGTGATC TTCCTGTCAT

7551 TTTGGTATCT GCGCTCTGCT GAAGCCAGTT ACCTTCGGAA AAAGAGTTGG
     AAACCATAGA CGCGAGACGA CTTCGGTCAA TGGAAGCCTT TTTCTCAACC

7601 TAGCTCTTGA TCCGGCAAAC AAACCACCGC TGGTAGCGGT GGTTTTTTTG
     ATCGAGAACT AGGCCGTTTG TTTGGTGGCG ACCATCGCCA CCAAAAAAAC

7651 TTTGCAAGCA GCAGATTACG CGCAGAAAAA AAGGATCTCA AGAAGATCCT
     AAACGTTCGT CGTCTAATGC GCGTCTTTTT TTCCTAGAGT TCTTCTAGGA

7701 TTGATCTTTT CTACGGGGTC TGACGCTCAG TGGAACGAAA ACTCACGTTA
     AACTAGAAAA GATGCCCCAG ACTGCGAGTC ACCTTGCTTT TGAGTGCAAT

7751 AGGGATTTTG GTCATGAGAT TATCAAAAAG GATCTTCACC TAGATCCTTT
     TCCCTAAAAC CAGTACTCTA ATAGTTTTTC CTAGAAGTGG ATCTAGGAAA

7801 TAAATTAAAA ATGAAGTTTT AAATCAATCT AAAGTATATA TGAGTAAACT
     ATTTAATTTT TACTTCAAAA TTTAGTTAGA TTTCATATAT ACTCATTTGA

7851 TGGTCTGACA GTTACCAATG CTTAATCAGT GAGGCACCTA TCTCAGCGAT
     ACCAGACTGT CAATGGTTAC GAATTAGTCA CTCCGTGGAT AGAGTCGCTA

7901 CTGTCTATTT CGTTCATCCA TAGTTGCCTG ACTCCCCGTC GTGTAGATAA
     GACAGATAAA GCAAGTAGGT ATCAACGGAC TGAGGGGCAG CACATCTATT

7951 CTACGATACG GGAGGGCTTA CCATCTGGCC CCAGTGCTGC AATGATACCG
     GATGCTATGC CCTCCCGAAT GGTAGACCGG GGTCACGACG TTACTATGGC

8001 CGAGACCCAC GCTCACCGGC TCCAGATTTA TCAGCAATAA ACCAGCCAGC
     GCTCTGGGTG CGAGTGGCCG AGGTCTAAAT AGTCGTTATT TGGTCGGTCG
```

```
                              -continued
8051 CGGAAGGGCC GAGCGCAGAA GTGGTCCTGC AACTTTATCC GCCTCCATCC
     GCCTTCCCGG CTCGCGTCTT CACCAGGACG TTGAAATAGG CGGAGGTAGG 8101 AGTCTATTAA TTGTTGCCGG GAAGCTAGAG TAAGTAGTTC GCCAGTTAAT
     TCAGATAATT AACAACGGCC CTTCGATCTC ATTCATCAAG CGGTCAATTA 8151 AGTTTGCGCA ACGTTGTTGC CATTGCTACA GGCATCGTGG TGTCACGCTC
     TCAAACGCGT TGCAACAACG GTAACGATGT CCGTAGCACC ACAGTGCGAG 8201 GTCGTTTGGT ATGGCTTCAT TCAGCTCCGG TTCCCAACGA TCAAGGCGAG
     CAGCAAACCA TACCGAAGTA AGTCGAGGCC AAGGGTTGCT AGTTCCGCTC 8251 TTACATGATC CCCCATGTTG TGCAAAAAAG CGGTTAGCTC CTTCGGTCCT
     AATGTACTAG GGGGTACAAC ACGTTTTTTC GCCAATCGAG GAAGCCAGGA 8301 CCGATCGTTG TCAGAAGTAA GTTGGCCGCA GTGTTATCAC TCATGGTTAT
     GGCTAGCAAC AGTCTTCATT CAACCGGCGT CACAATAGTG AGTACCAATA 8351 GGCAGCACTG CATAATTCTC TTACTGTCAT GCCATCCGTA AGATGCTTTT
     CCGTCGTGAC GTATTAAGAG AATGACAGTA CGGTAGGCAT TCTACGAAAA 8401 CTGTGACTGG TGAGTACTCA ACCAAGTCAT TCTGAGAATA GTGTATGCGG
     GACACTGACC ACTCATGAGT TGGTTCAGTA AGACTCTTAT CACATACGCC 8451 CGACCGAGTT GCTCTTGCCC GGCGTCAATA CGGGATAATA CCGCGCCACA
     GCTGGCTCAA CGAGAACGGG CCGCAGTTAT GCCCTATTAT GGCGCGGTGT 8501 TAGCAGAACT TTAAAAGTGC TCATCATTGG AAAACGTTCT TCGGGGCGAA
     ATCGTCTTGA AATTTTCACG AGTAGTAACC TTTTGCAAGA AGCCCCGCTT 8551 AACTCTCAAG GATCTTACCG CTGTTGAGAT CCAGTTCGAT GTAACCCACT
     TTGAGAGTTC CTAGAATGGC GACAACTCTA GGTCAAGCTA CATTGGGTGA 8601 CGTGCACCCA ACTGATCTTC AGCATCTTTT ACTTTCACCA GCGTTTCTGG
     GCACGTGGGT TGACTAGAAG TCGTAGAAAA TGAAAGTGGT CGCAAAGACC 8651 GTGAGCAAAA ACAGGAAGGC AAAATGCCGC AAAAAAGGGA ATAAGGGCGA
     CACTCGTTTT TGTCCTTCCG TTTTACGGCG TTTTTTCCCT TATTCCCGCT 8701 CACGGAAATG TTGAATACTC ATACTCTTCC TTTTTCAATA TTATTG
     GTGCCTTTAC AACTTATGAG TATGAGAAGG AAAAAGTTAT AATAAC Sequence of p(CAB)2
   1 TGAAGCATTT ATCAGGGTTA TTGTCTCATG AGCGGATACA TATTTGAATG (SEQ ID NO: 12)
     ACTTCGTAAA TAGTCCCAAT AACAGAGTAC TCGCCTATGT ATAAACTTAC (SEQ ID NO: 13)

51 TATTTAGAAA AATAAACAAA TAGGGGTTCC GCGCACATTT CCCCGAAAAG
     ATAAATCTTT TTATTTGTTT ATCCCCAAGG CGCGTGTAAA GGGGCTTTTC

101 TGCCACCTGA CGTCTAAGAA ACCATTATTA TCATGACATT AACCTATAAA
     ACGGTGGACT GCAGATTCTT TGGTAATAAT AGTACTGTAA TTGGATATTT

151 AATAGGCGTA TCACGAGGCC CTTTCGTCTC GCGCGTTTCG GTGATGACGG
     TTATCCGCAT AGTGCTCCGG GAAAGCAGAG CGCGCAAAGC CACTACTGCC

201 TGAAAACCTC TGACACATGC AGCTCCCGGA GACGGTCACA GCTTGTCTGT
     ACTTTTGGAG ACTGTGTACG TCGAGGGCCT CTGCCAGTGT CGAACAGACA

251 AAGCGGATGC CGGGAGCAGA CAAGCCCGTC AGGGCGCGTC AGCGGGTGTT
     TTCGCCTACG GCCCTCGTCT GTTCGGGCAG TCCCGCGCAG TCGCCCACAA

301 GGCGGGTGTC GGGGCTGGCT TAACTATGCG GCATCAGAGC AGATTGTACT
     CCGCCCACAG CCCCGACCGA ATTGATACGC CGTAGTCTCG TCTAACATGA

351 GAGAGTGCAC CATATGCGGT GTGAAATACC GCACAGATGC GTAAGGAGAA
     CTCTCACGTG GTATACGCCA CACTTTATGG CGTGTCTACG CATTCCTCTT

401 AATACCGCAT CAGGCGCCAT TCGCCATTCA GGCTGCGCAA CTGTTGGGAA
     TTATGGCGTA GTCCGCGGTA AGCGGTAAGT CCGACGCGTT GACAACCCTT

451 GGGCGATCGG TGCGGGCCTC TTCGCTATTA CGCCAGCTGG CGAAAGGGGG
     CCCGCTAGCC ACGCCCGGAG AAGCGATAAT GCGGTCGACC GCTTTCCCCC

501 ATGTGCTGCA AGGCGATTAA GTTGGGTAAC GCCAGGGTTT TCCCAGTCAC
     TACACGACGT TCCGCTAATT CAACCCATTG CGGTCCCAAA AGGGTCAGTG

551 GACGTTGTAA AACGACGGCC AGTGAATTCA TGACTGCAAT TTTAGAGAGA
     CTGCAACATT TTGCTGCCGG TCACTTAAGT ACTGACGTTA AAATCTCTCT
```

```
 601 CGCGAAAGCG AAAGCCTATG GGGTCGCTTC TGTAACTGGA TAACTAGCAC
     GCGCTTTCGC TTTCGGATAC CCCAGCGAAG ACATTGACCT ATTGATCGTG

651 TGAAACCGT  CTTTACATTG GATGGTTTGG TGTTTTGATG ATCCCTACCT
     ACTTTTGGCA GAAATGTAAC CTACCAAACC ACAAAACTAC TAGGGATGGA

701 TATTGACGGC AACTTCTGTA TTTATTATTG CCTTCATTGC TGCTCCTCCA
     ATAACTGCCG TTGAAGACAT AAATAATAAC GGAAGTAACG ACGAGGAGGT

751 GTAGACATTG ATGGTATTCG TGAACCTGTT TCAGGGTCTC TACTTTACGG
     CATCTGTAAC TACCATAAGC ACTTGGACAA AGTCCCAGAG ATGAAATGCC

801 AAACAATATT ATTTCCGGTG CCATTATTCC TACTTCTGCA GCTATAGGTT
     TTTGTTATAA TAAAGGCCAC GGTAATAAGG ATGAAGACGT CGATATCCAA

851 TACATTTTTA CCCAATCTGG GAAGCGGCAT CCGTTGATGA ATGGTTATAC
     ATGTAAAAAT GGGTTAGACC CTTCGCCGTA GGCAACTACT TACCAATATG

901 AACGGTGGTC CTTATGAACT AATTGTTCTA CACTTCTTAC TTGGCGTAGC
     TTGCCACCAG GAATACTTGA TTAACAAGAT GTGAAGAATG AACCGCATCG

951 TTGTTACATG GGTCGTGAGT GGGAGCTTAG TTTCCGTCTG GGTATGCGAC
     AACAATGTAC CCAGCACTCA CCCTCGAATC AAAGGCAGAC CCATACGCTG

1001 CTTGGATTGC TGTTGCATAT TCAGCTCCTG TTGCAGCTGC TACCGCAGTT
     GAACCTAACG ACAACGTATA AGTCGAGGAC AACGTCGACG ATGGCGTCAA

1051 TTCTTGATCT ACCCAATTGG TCAAGGAAGT TTTTCTGATG GTATGCCTCT
     AAGAACTAGA TGGGTTAACC AGTTCCTTCA AAAAGACTAC CATACGGAGA

1101 AGGAATCTCT GGTACTTTCA ATTTCATGAT TGTATTCCAG GCTGAGCACA
     TCCTTAGAGA CCATGAAAGT TAAAGTACTA ACATAAGGTC CGACTCGTGT

1151 ACATCCTTAT GCACCCATTT CACATGTTAG GCGTAGCTGG TGTATTCGGC
     TGTAGGAATA CGTGGGTAAA GTGTACAATC CGCATCGACC ACATAAGCCG

1201 GGCTCCCTAT TCAGTGCTAT GCATGGTTCC TTGGTAACTT CTAGTTTGAT
     CCGAGGGATA AGTCACGATA CGTACCAAGG AACCATTGAA GATCAAACTA

1251 CAGGGAAACC ACAGAAAATG AATCTGCTAA TGAAGGTTAC AGATTCGGTC
     GTCCCTTTGG TGTCTTTTAC TTAGACGATT ACTTCCAATG TCTAAGCCAG

1301 AAGAGGAAGA AACTTATAAC ATCGTAGCCG CTCATGGTTA TTTTGGCCGA
     TTCTCCTTCT TTGAATATTG TAGCATCGGC GAGTACCAAT AAAACCGGCT

1351 TTGATCTTCC AATATGCTAG TTTCAACAAC TCTCGTTCGT TACACTTCTT
     AACTAGAAGG TTATACGATC AAAGTTGTTG AGAGCAAGCA ATGTGAAGAA

1401 CCTAGCTGCT TGGCCTGTAG TAGGTATCTG GTTTACCGCT TTAGGTATCA
     GGATCGACGA ACCGGACATC ATCCATAGAC CAAATGGCGA AATCCATAGT

1451 GCACTATGGC TTTCAACCTA AATGGTTTCA ATTTCAACCA ATCTGTAGTT
     CGTGATACCG AAAGTTGGAT TTACCAAAGT TAAAGTTGGT TAGACATCAA

1501 GACAGTCAAG GCCGTGTAAT TAATACTTGG GCTGATATCA TTAACCGTGC
     CTGTCAGTTC CGGCACATTA ATTATGAACC CGACTATAGT AATTGGCACG

1551 TAACCTTGGT ATGGAAGTTA TGCATGAACG TAATGCTCAC AACTTCCCTC
     ATTGGAACCA TACCTTCAAT ACGTACTTGC ATTACGAGTG TTGAAGGGAG

1601 TAGACCTAGC TGCTATCGAA GCTCCATCTA CAAAGGGAGA AGTCGACGGT
     ATCTGGATCG ACGATAGCTT CGAGGTAGAT GTTTACCTAT TCAGCTGCCA

1651 ATCGATAAGC TTCCCCGGGA GACCACAACG GTTTCCCTCT AGAAATAATT
     TAGCTATTCG AAGGGGCCCT CTGGTGTTGC CAAAGGGAGA TCTTTATTAA

1701 TTGTTTAACT TTAAGAAGGA GATATACATA TGAACCCGAA CTCATTTCAA
     AACAAATTGA AATTCTTCCT CTATATGTAT ACTTGGGCTT GAGTAAAGTT

1751 TTCAAAGAAA ACATACTACA ATTTTTTTCT GTACATGATG ACATCTGGAA
     AAGTTTCTTT TGTATGATGT TAAAAAAAGA CATGTACTAC TGTAGACCTT

1801 AAAATTACAA GAATTTTATT ATGGGCAAAG CCCAATTAAT GAGGCTTTGG
     TTTTAATGTT CTTAAAATAA TACCCGTTTC GGGTTAATTA CTCCGAAACC

1851 CGCAGCTCAA CAAAGAAGAT ATGTCTTTGT TCTTTGAAGC ACTATCTAAA
     GCGTCGAGTT GTTTCTTCTA TACAGAAACA AGAAACTTCG TGATAGATTT

1901 AACCCAGCTC GCATGATGGA AATGCAATGG AGCTGGTGGC AAGGTCAAAT
     TTGGGTCGAG CGTACTACCT TTACGTTACC TCGACCACCG TTCCAGTTTA
```

-continued

```
1951 ACAAATCTAC CAAAATGTGT TGATGCGCAG CGTGGCCAAA GATGTAGCAC
     TGTTTAGATG GTTTTACACA ACTACGCGTC GCACCGGTTT CTACATCGTG

2001 CATTTATTCA GCCTGAAAGT GGTGATCGTC GTTTTAACAG CCCATTATGG
     GTAAATAAGT CGGACTTTCA CCACTAGCAG CAAAATTGTC GGGTAATACC

2051 CAAGAACACC CAAATTTTGA CTTGTTGTCA CAGTCTTATT TACTGTTTAG
     GTTCTTGTGG GTTTAAAACT GAACAACAGT GTCAGAATAA ATGACAAATC

2101 CCAGTTAGTG CAAAACATGG TAGATGTGGT CGAAGGTGTT CCAGACAAAG
     GGTCAATCAC GTTTTGTACC ATCTACACCA GCTTCCACAA GGTCTGTTTC

2151 TTCGCTATCG TATTCACTTC TTTACCCGCC AAATGATCAA TGCGTTATCT
     AAGCGATAGC ATAAGTGAAG AAATGGGCGG TTTACTAGTT ACGCAATAGA

2201 CCAAGTAACT TTCTGTGGAC TAACCCAGAA GTGATTCAGC AAACTGTAGC
     GGTTCATTGA AAGACACCTG ATTGGGTCTT CACTAAGTCG TTTGACATCG

2251 TGAACAAGGT GAAAACTTAG TCCGTGGCAT GCAAGTTTTC CATGATGATG
     ACTTGTTCCA CTTTTGAATC AGGCACCGTA CGTTCAAAAG GTACTACTAC

2301 TCATGAATAG CGGCAAGTAT TTATCTATTC GCATGGTGAA TAGCGACTCT
     AGTACTTATC GCCGTTCATA AATAGATAAG CGTACCACTT ATCGCTGAGA

2351 TTCAGCTTGG GCAAAGATTT AGCTTACACC CCTGGTGCAG TCGTCTTTGA
     AAGTCGAACC CGTTTCTAAA TCGAATGTGG GGACCACGTC AGCAGAAACT

2401 AAATGACATT TTCCAATTAT TGCAATATGA AGCAACTACT GAAATGTGT
     TTTACTGTAA AAGGTTAATA ACGTTATACT TCGTTGATGA CTTTTACACA

2451 ATCAAACCCC TATTCTAGTC GTACCACCGT TTATCAATAA ATATTATGTG
     TAGTTTGGGG ATAAGATCAG CATGGTGGCA AATAGTTATT TATAATACAC

2501 CTGGATTTAC GCGAACAAAA CTCTTTAGTG AACTGGTTGC GCCAGCAAGG
     GACCTAAATG CGCTTGTTTT GAGAAATCAC TCGACCACCG CGGTCGTTCC

2551 TCATACAGTC TTTTTAATGT CATGGCGTAA CCCAAATGCC GAACAGAAAG
     AGTATGTCAG AAAAATTACA GTACCGCATT GGGTTTACGG CTTGTCTTTC

2601 AATTGACTTT TGCCGATCTC ATTACACAAG GTTCAGTGGA AGCTTTGCGT
     TTAACTGAAA ACGGCTAGAG TAATGTGTTC CAAGTCACCT TCGAAACGCA

2651 GTAATTGAAG AAATTACCGG TGAAAAAGAG GCCAACTGCA TTGGCTACTG
     CATTAACTTC TTTAATGGCC ACTTTTCTC CGGTTGACGT AACCGATGAC

2701 TATTGGTGGT ACGTTACTTG CTGCGACTCA AGCCTATTAC GTGGCAAAAC
     ATAACCACCA TGCAATGAAC GACGCTGAGT TCGGATAATG CACCGTTTTG

2751 GCCTGAAAAA TCACGTAAAG TCTGCGACCT ATATGGCCAC CATTATCGAC
     CGGACTTTTT AGTGCATTTC AGACGCTGGA TATACCGGTG GTAATAGCTG

2801 TTTGAAAACC CAGGCAGCTT AGGTGTATTT ATTAATGAAC CTGTAGTGAG
     AAACTTTTGG GTCCGTCGAA TCCACATAAA TAATTACTTG GACATCACTC

2851 CGGTTTAGAA AACCTGAACA ATCAATTGGG TTATTTCGAT GGTCGTCAGT
     GCCAAATCTT TTGGACTTGT TAGTTAACCC AATAAAGCTA CCAGCAGTCA

2901 TGGCAGTTAC CTTCAGTTTA CTGCGTGAAA ATACGCTGTA CTGGATTTAC
     ACCGTCAATG GAAGTCAAAT GACGCACTTT TATGCGACAT GACCTAAATG

2951 TACATCGACA ACTACTTAAA AGGTAAAGAA CCTTCTGATT TTGATATTTT
     ATGTAGCTGT TGATGAATTT TCCATTTCTT GGAAGACTAA AACTATAAAA

3001 ATATTCGAAC AGCGATGGTA CGAATATCCC TGCCAAAATT CATAATTTCT
     TATAACCTTG TCGCTACCAT GCTTATAGGG ACGGTTTTAA GTATTAAAGA

3051 TATTGCGCAA TTTGTATTTG AACAATGAAT TGATTTCACC AAATGCCGTT
     ATAACGCGTT AAACATAAAC TTGTTACTTA ACTAAAGTGG TTTACGGCAA

3101 AAGGTTAACG GTGTGGGCTT GAATCTATCT CGTGTAAAAA CACCAAGCTT
     TTCCAATTGC CACACCCGAA CTTAGATAGA GCACATTTTT GTGGTTCGAA

3151 CTTTATTGCG ACGCAGGAAG ACCATATCGC ACTTTGGGAT ACTTGTTCC
     GAAATAACGC TGCGTCCTTC TGGTATAGCG TGAAACCCTA TGAACAAAGG

3201 GTGGCGCAGA TTACTTGGGT GGTGAATCAA CCTTGGTTTT AGGTGAATCT
     CACCGCGTCT AATGAACCCA CCACTTAGTT GGAACCAAAA TCCACTTAGA

3251 GGACACGTAG CAGGTATTGT CAATCCTCCA AGCCGTAATA AATACGGTTG
     CCTGTGCATC GTCCATAACA GTTAGGAGGT TCGGCATTAT TTATGCCAAC
```

-continued

```
3301 CTACACCAAT GCTGCCAAGT TTGAAAATAC CAAACAATGG CTAGATGGCG
     GATGTGGTTA CGACGGTTCA AACTTTTATG GTTTGTTACC GATCTACCGC

3351 CAGAATATCA CCCTGAATCT TGGTGGTTGC GCTGGCAGGC ATGGGTCACA
     GTCTTATAGT GGGACTTAGA ACCACCAACG CGACCGTCCG TACCCAGTGT

3401 CCGTACACTG GTGAACAAGT CCCTGCCCGC AACTTGGGTA ATGCGCAGTA
     GGCATGTGAC CACTTGTTCA GGGACGGGCG TTGAACCCAT TACGCGTCAT

3451 TCCAAGCATT GAAGCGGCAC CGGGTCGCTA TGTTTTGGTA AATTTATTCT
     AGGTTCGTAA CTTCGCCGTG GCCCAGCGAT ACAAAACCAT TTAAATAAGA

3501 AAGCGGCCGC CACCGCGGTG GAGCTCAATA AAAAAAATCT AGATGCTTAT
     TTCGCCGGCG GTGGCGCCAC CTCGAGTTAT TTTTTTTACA TCTACGAATA

3551 GATTCAGTAG TAGGAGGCAA ACCATATGAA AGATGTTGTG ATTGTTGCAG
     CTAAGTCATC ATCCTCCGTT TGGTATACTT TCTACAACAC TAACAACGTC

3601 CAAAACGTAC TGCGATTGGT AGCTTTTTAG GTAGTCTTGC ATCTTTATCT
     GTTTTGCATG ACGCTAACCA TCGAAAAATC CATCAGAACG TAGAAATAGA

3651 GCACCACAGT TGGGGCAAAC AGCAATTCGT GCAGTTTTAG ACAGCGCTAA
     CGTGGTGTCA ACCCCGTTTG TCGTTAAGCA CGTCAAAATC TGTCGCGATT

3701 TGTAAAACCT GAACAAGTTG ATCAGGTGAT TATGGGCAAC GTACTCACGA
     ACATTTTGGA CTTGTTCAAC TAGTCCACTA ATACCCGTTG CATGAGTGCT

3751 CAGGCGTGGG ACAAAACCCT GCACGTCAGG CAGCAATTGC TGCTGGTATT
     GTCCGCACCC TGTTTTGGGA CGTGCAGTCC GTCGTTAACG ACGACCATAA

3801 CCAGTACAAG TGCCTGCATC TACGCTGAAT GTCGTCTGTG GTTCAGGTTT
     GGTCATGTTC ACGGACGTAG ATGCGACTTA CAGCAGACAC CAAGTCCAAA

3851 GCGTGCGGTA CATTTGGCAG CACAAGCCAT TCAATGCGAT GAAGCCGACA
     CGCACGCCAT GTAAACCGTC GTGTTCGGTA AGTTACGCTA CTTCGGCTGT

3901 TTGTGGTCGC AGGTGGTCAA GAATCTATCT CACAAAGTGC GCACTATATG
     AACACCAGCG TCCACCAGTT CTTAGATACA GTGTTTCACG CGTGATATAC

3951 CAGCTGCGTA ATGGGCAAAA AATGGGTAAT GCACAATTGG TGGATAGCAT
     GTCGACGCAT TACCCGTTTT TTACCCATTA CGTGTTAACC ACCTATCGTA

4001 GGTGGCTGAT GGTTTAACCG ATGCCTATAA CCAGTATCAA ATGGGTATTA
     CCACCGACTA CCAAATTGGC TACGGATATT GGTCATAGTT TACCCATAAT

4051 CCGCAGAAAA TATTGTAGAA AAACTGGGTT TAAACCGTGA AGAACAAGAT
     GGCGTCTTTT ATAACATCTT TTTGACCCAA ATTTGGCACT TCTTGTTCTA

4101 CAACTTGCAT TGACTTCACA ACAACGTGCT GCGGCAGCTC AGGCAGCTGG
     GTTGAACGTA ACTGAAGTGT TGTTGCACGA CGCCGTCGAG TCCGTCGACC

4151 CAAGTTTAAA GATGAAATTG CCGTAGTCAG CATTCCACAA CGTAAAGGTG
     GTTCAAATTT CTACTTTAAC GGCATCAGTC GTAAGGTGTT GCATTTCCAC

4201 AGCCTGTTGT ATTTGCTGAA GATGAATACA TTAAAGCCAA TACCAGCCTT
     TCGGACAACA TAAACGACTT CTACTTATGT AATTTCGGTT ATGGTCGGAA

4251 GAAAGCCTCA CAAAACTACG CCCAGCCTTT AAAAAAGATG GTAGCGTAAC
     CTTTCGGAGT GTTTTGATGC GGGTCGGAAA TTTTTTCTAC CATCGCATTG

4301 CGCAGGTAAT GCTTCAGGCA TTAATGATGG TGCAGCAGCA GTACTGATGA
     GCGTCCATTA CGAAGTCCGT AATTACTACC ACGTCGTCGT CATGACTACT

4351 TGAGTGCGGA CAAAGCAGCA GAATTAGGTC TTAAGCCATT GGCACGTATT
     ACTCACGCCT GTTTCGTCGT CTTAATCCAG AATTCGGTAA CCGTGCATAA

4401 AAAGGCTATG CCATGTCTGG TATTGAGCCT GAAATTATGG GGCTTGGTCC
     TTTCCGATAC GGTACAGACC ATAACTCGGA CTTTAATACC CCGAACCAGG

4451 TGTCGATGCA GTAAAGAAAA CCCTCAACAA AGCAGGCTGG AGCTTAGATC
     ACAGCTACGT CATTTCTTTT GGGAGTTGTT TCGTCCGACC TCGAATCTAG

4501 AGGTTGATTT GATTGAAGCC AATGAAGCAT TTGCTGCACA GGCTTGGGT
     TCCAACTAAA CTAACTTCGG TTACTTCGTA AACGACGTGT CCGAAACCCA

4551 GTTGCTAAAG AATTAGGCTT AGACCTGGAT AAAGTCAACG TCAATGGCGG
     CAACGATTTC TTAATCCGAA TCTGGACCTA TTTCAGTTGC AGTTACCGCC

4601 TGCAATTGCA TTGGGTCACC CAATTGGGGC TTCAGGTTGC CGTATTTTGG
     ACGTTAACGT AACCCAGTGG GTTAACCCCG AAGTCCAACG GCATAAAACC
```

-continued

```
4651 TGACTTTATT ACATGAAATG CAGCGCCGTG ATGCCAAGAA AGGCATTGCA
     ACTGAAATAA TGTACTTTAC GTCGCGGCAC TACGGTTCTT TCCGTAACGT

4701 ACCCTCTGTG TTGGCGGTGG TATGGGTGTT GCACTTGCAG TTGAACGTGA
     TGGGAGACAC AACCGCCACC ATACCCACAA CGTGAACGTC AACTTGCACT

4751 CTAAGCGGCC GCTCGAGTGG CGGCTCAAGA TCAGCCTCAT CAAAACCTTA
     GATTCGCCGG CGAGCTCACC GCCGAGTTCT AGTCGGAGTA GTTTTGGAAT

4801 TATTCCCTGA GGAGGTTCTA CCCATATGAC AACATTACAA GGTAAAGTAG
     ATAAGGGACT CCTCCAAGAT GGGTATACTG TTGTAATGTT CCATTTCATC

4851 CAATCGTAAC AGGCGGATCT AAAGGTATCG GGGCAGCAAT TACACGTGAG
     GTTAGCATTG TCCGCCTAGA TTTCCATAGC CCCGTCGTTA ATGTGCACTC

4901 CTTGCTTCTA ATGGAGTAAA AGTAGCAGTA AACTATAACA GCAGTAAAGA
     GAACGAAGAT TACCTCATTT TCATCGTCAT TTGATATTGT CGTCATTTCT

4951 ATCTGCAGAA GCAATTGTAA AAGAAATTAA AGACAACGGC GGAGAAGCTA
     TAGACGTCTT CGTTAACATT TTCTTTAATT TCTGTTGCCG CCTCTTCGAT

5001 TTGCGGTTCA AGCTGACGTG TCTTATGTAG ATCAAGCAAA ACACCTAATC
     AACGCCAAGT TCGACTGCAC AGAATACATC TAGTTCGTTT TGTGGATTAG

5051 GAAGAAACAA AAGCTGCGTT TGGTCAATTA GACATTCTAG TAAACAATGC
     CTTCTTTGTT TTCGACGCAA ACCAGTTAAT CTGTAAGATC ATTTGTTACG

5101 TGGAATTACG CGCGACCGTT CATTCAAGAA GTTAGGTGAA GAAGATTGGA
     ACCTTAATGC GCGCTGGCAA GTAAGTTCTT CAATCCACTT CTTCTAACCT

5151 AAAAAGTAAT TGATGTAAAC TTACATAGCG TATACAACAC AACATCAGCT
     TTTTTCATTA ACTACATTTG AATGTATCGC ATATGTTGTG TTGTAGTCGA

5201 GCGCTAACGC ACCTTTTAGA ATCTGAAGGT GGTCGTGTTA TCAATATTTC
     CGCGATTGCG TGGAAAATCT TAGACTTCCA CCAGCACAAT AGTTATAAAG

5251 ATCAATTATT GGTCAAGCGG GCGGATTTGG TCAAACAAAC TACTCAGCTG
     TAGTTAATAA CCAGTTCGCC CGCCTAAACC AGTTTGTTTG ATGAGTCGAC

5301 CTAAAGCAGG TATGCTAGGA TTCACTAAAT CATTAGCTCT TGAACTAGCT
     GATTTCGTCC ATACGATCCT AAGTGATTTA GTAATCGAGA ACTTGATCGA

5351 AAGACAGGCG TAACGGTTAA TGCAATTTGC CCAGGATTTA TTGAAACGGA
     TTCTGTCCGC ATTGCCAATT ACGTTAAACG GGTCCTAAAT AACTTTGCCT

5401 AATGGTGATG GCAATTCCTG AAGATGTTCG TGCAAAAATT GTTGCGAAAA
     TTACCACTAC CGTTAAGGAC TTCTACAAGC ACGTTTTTAA CAACGCTTTT

5451 TTCCAACTCG TCGCTTAGGT CACGCTGAAG AAATTGCACG TGGAGTTGTT
     AAGGTTGAGC AGCGAATCCA GTGCGACTTC TTTAACGTGC ACCTCAACAA

5501 TACTTAGCAA AAGACGGCGC GTACATTACA GGACAACAGT TAAACATTAA
     ATGAATCGTT TTCTGCCGCG CATGTAATGT CCTGTTGTCA ATTTGTAATT

5551 CGGCGGCTTA TACATGTAAT GGATCCAATC GATACAAGTG AGTTGTAGGG
     GCCGCCGAAT ATGTACATTA CCTAGGTTAG CTATGTTCAC TCAACATCCC

5601 AGGCAACCAT GGCAGAAGCG GTGATCGCCG AAGTATCGAC TCAACTATCA
     TCCGTTGGTA CCGTCTTCGC CACTAGCGGC TTCATAGCTG AGTTGATAGT

5651 GAGGTAGTTG GCGTCATCGA GCGCCATCTC GAACCGACGT TGCTGGCCGT
     CTCCATCAAC CGCAGTAGCT CGCGGTAGAG CTTGGCTGCA ACGACCGGCA

5701 ACATTTGTAC GGCTCCGCAG TGGATGGCGG CCTGAAGCCA CACAGTGATA
     TGTAAACATG CCGAGGCGTC ACCTACCGCC GGACTTCGGT GTGTCACTAT

5751 TTGATTTGCT GGTTACGGTG ACCGTAAGGC TTGATGAAAC AACGCGGCGA
     AACTAAACGA CCAATGCCAC TGGCATTCCG AACTACTTTG TTGCGCCGCT

5801 GCTTTGATCA ACGACCTTTT GGAAACTTCG GCTTCCCCTG GAGAGAGCGA
     CGAAACTAGT TGCTGGAAAA CCTTTGAAGC CGAAGGGGAC CTCTCTCGCT

5851 GATTCTCCGC GCTGTAGAAG TCACCATTGT TGTGCACGAC GACATCATTC
     CTAAGAGGCG CGACATCTTC AGTGGTAACA ACACGTGCTG CTGTAGTAAG

5901 CGTGGCGTTA TCCAGCTAAG CGCGAACTGC AATTTGGAGA ATGGCAGCGC
     GCACCGCAAT AGGTCGATTC GCGCTTGACG TTAAACCTCT TACCGTCGCG

5951 AATGACATTC TTGCAGGTAT CTTCGAGCCA GCCACGATCG ACATTGATCT
     TTACTGTAAG AACGTCCATA GAAGCTCGGT CGGTGCTAGC TGTAACTAGA
```

-continued

```
6001 GGCTATCTTG CTGACAAAAG CAAGAGAACA TAGCGTTGCC TTGGTAGGTC
     CCGATAGAAC GACTGTTTTC GTTCTCTTGT ATCGCAACGG AACCATCCAG

6051 CAGCGGCGGA GGAACTCTTT GATCCGGTTC CTGAACAGGA TCTATTTGAG
     GTCGCCGCCT CCTTGAGAAA CTAGGCCAAG GACTTGTCCT AGATAAACTC

6101 GCGCTAAATG AAACCTTAAC GCTATGGAAC TCGCCGCCCG ACTGGGCTGG
     CGCGATTTAC TTTGGAATTG CGATACCTTG AGCGGCGGGC TGACCCGACC

6151 CGATGAGCGA AATGTAGTGC TTACGTTGTC CCGCATTTGG TACAGCGCAG
     GCTACTCGCT TTACATCACG AATGCAACAG GGCGTAAACC ATGTCGCGTC

6201 TAACCGGCAA AATCGCGCCG AAGGATGTCG CTGCCGACTG GGCAATGGAG
     ATTGGCCGTT TTAGCGCGGC TTCCTACAGC GACGGCTGAC CCGTTACCTC

6251 CGCCTGCCGG CCCAGTATCA GCCCGTCATA CTTGAAGCTA GACAGGCTTA
     GCGGACGGCC GGGTCATAGT CGGGCAGTAT GAACTTCGAT CTGTCCGAAT

6301 TCTTGGACAA GAAGAAGATC GCTTGGCCTC GCGCGCAGAT CAGTTGGAAG
     AAAACTAGTT CTTCTTCTAG CGAACCGGAG CGCGCGTCTA GTCAACCTTC

6351 AATTTGTCCA CTACGTGAAA GGCGAGATCA CCAAGGTAGT CGGCAAATAA
     TTAAACAGGT GATGCACTTT CCGCTCTAGT GGTTCCATCA GCCGTTTATT

6401 ATCTAGGCCG AATTGGGCCT AGTCTATAGG AGGTTTTGAA AAGAAAGGAG
     TAGATCCGGC TTAACCCGGA TCAGATATCC TCCAAAACTT TTCTTTCCTC

6451 CAATAATCAT TTTCTTGTTC TATCAAGAGG GTGCTATTGC TCCTTTCTTT
     GTTATTAGTA AAAGAACAAG ATAGTTCTCC CACGATAACG AGGAAAGAAA

6501 TTTTCTTTTT ATTTATTTAC TAGTATTTTA CTTACATAGA CTTTTTTGTT
     AAAAGAAAAA TAAATAAATG ATCATAAAAT GAATGTATCT GAAAAACTAA

6551 TACATTATAG AAAAGAAGG AGAGGTTATT TTCTTGCATT TATTCATGAT
     ATGTAATATC TTTTCTTCC TCTCCAATAA AAGAACGTAA ATAAGTACTA

6601 TGAGTATTCT ATTTTGATTT TGTATTTGTT TAAAATTGTA GAAATAGAAC
     ACTCATAAGA TAAAACTAAA ACATAAACAA ATTTTAACAT CTTTATCTTG

6651 TTGTTTCTCT TCTTGCTAAT GTTACTATAT CTTTTTTGTT TTTTTTTTCC
     AACAAAGAGA AGAACGATTA CAATGATATA GAAAACTAA AAAAAAAGG

6701 AAAAAAAAAA TCAAATTTTG ACTTCTTCTT ATCTCTTATC TTTGAATATC
     TTTTTTTTTT AGTTTAAAAC TGAAGAAGAA TAGAGAATAG AAACTTATAG

6751 TCTTATCTTT GAAATAATAA TATCATTGAA ATAAGAAAGA AGAGCTATAT
     AGAATAGAAA CTTTATTATT ATAGTAACTT TATTCTTTCT TCTCGATATA

6801 TCGAACTTGA ATCTTTTGTT TTCTAATTTA AATAATGTAA AAACGGAATG
     AGCTTGAACT TAGAAAACAA AAGATTAAAT TTATTACATT TTTGCCTTAC

6851 TAAGTAGGCG AGGGGGCGGA TGTAGCCAAG TGGATCAAGG CAGTGGATTG
     ATTCATCCGC TCCCCCGCCT ACATCGGTTC ACCTAGTTCC GTCACCTAAC

6901 TGAATCCACC ATGCGCGGGT TCAATTCCCG TCGTTCGCCC ATAATTACTC
     ACTTAGGTGG TACGCGCCCA AGTTAAGGGC AGCAAGCGGG TATTAATGAG

6951 CTATTTTTTT TTTTTTGTA AAAACGAAGA ATTTAATTCG ATTTTCTCTC
     GATAAAAAAA AAAAAAACAT TTTTGCTTCT TAAATTAAGC TAAAAGAGAG

7001 CTATTTACTA CGGCGACGAA GAATCAAATT ATCACTATAT TTATTCCTTT
     GATAAATGAT GCCGCTGCTT CTTAGTTTAA TAGTGATATA AATAAGGAAA

7051 TTCTACTTCT TCTTCCAAGT GCAGGATAAC CCCAAGGGGT TGTGGGTTTT
     AAGATGAAGA AGAAGGTTCA CGTCCTATTG GGGTTCCCCA ACACCCAAAA

7101 TTTCTACCAA TTGGGGCTCT CCCTTCACCA CCCCCATGGG GATGGTCTAC
     AAAGATGGTT AACCCCGAGA GGGAAGTGGT GGGGGTACCC CTACCAGATG

7151 AGGGTTCATA ACTACTCCTC TTACTACAGG ACGCTTACCT AGCCAACGCT
     TCCCAAGTAT TGATGAGGAG AATGATGTCC TGCGAATGGA TCGGTTGCGA

7201 TAGATCCGGC TCTACCCAAA CTTTTCTGGT TCACCCCAAC ATTCCCCACT
     ATCTAGGCCG AGATGGGTTT GAAAAGACCA AGTGGGTTG TAAGGGGTGA

7251 TGTCCGACTG TTGCTGAGCA GTTTTTGGAT ATCAAACGGA CCTCCCCAGA
     ACAGGCTGAC AACGACTCGT CAAAAACCTA TAGTTTGCCT GGAGGGGTCT

7301 AGGTAATTTT AATGTGGCCG ATTTCCCCTC TTTTGCAATC AGTTTCGCTA
     TCCATTAAAA TTACACCGGC TAAAGGGGAG AAAACGTTAG TCAAAGCGAT
```

-continued

```
7351 CAGCACCCGC TGCTCTAGCT AATTGTCCAC CCTTTCCAAG TGTGATTTCT
     GTCGTGGGCG ACGAGATCGA TTAACAGGTG GGAAAGGTTC ACACTAAAGA

7401 ATGTTATGTA TGGCCGTGCC TAAGGGCATA TCGGTTGAAG TAGATTCTTC
     TACAATACAT ACCGGCACGG ATTCCCGTAT AGCCAACTTC ATCTAAGAAG

7451 TTTTGATCAA TCAAAACCCC TTCCCAAACT GTACAAGCTT GGCGTAATCA
     AAAACTAGTT AGTTTTGGGG AAGGGTTTGA CATGTTCGAA CCGCATTAGT

7501 TGGTCATAGC TGTTTCCTGT GTGAAATTGT TATCCGCTCA CAATTCCACA
     ACCAGTATCG ACAAAGGACA CACTTTAACA ATAGGCGAGT GTTAAGGTGT

7551 CAACATACGA GCCGGAAGCA TAAAGTGTAA AGCCTGGGGT GCCTAATGAG
     GTTGTATGCT CGGCCTTCGT ATTTCACATT TCGGACCCCA CGGATTACTC

7601 TGAGCTAACT CACATTAATT GCGTTGCGCT CACTGCCCGC TTTCCAGTCG
     ACTCGATTGA GTGTAATTAA CGCAACGCGA GTGACGGGCG AAAGGTCAGC

7651 GGAAACCTGT CGTGCCAGCT GCATTAATGA ATCGGCCAAC GCGCGGGGAG
     CCTTTGGACA GCACGGTCGA CGTAATTACT TAGCCGGTTG CGCGCCCCTC

7701 AGGCGGTTTG CGTATTGGGC GCTCTTCCGC TTCCTCGCTC ACTGACTCGC
     TCCGCCAAAC GCATAACCCG CGAGAAGGCG AAGGAGCGAG TGACTGAGCG

7751 TGCGCTCGGT CGTTCGGCTG CGGCGAGCGG TATCAGCTCA CTCAAAGGCG
     ACGCGAGCCA GCAAGCCGAC GCCGCTCGCC ATAGTCGAGT GAGTTTCCGC

7801 GTAATACGGT TATCCACAGA ATCAGGGGAT AACGCAGGAA AGAACATGTG
     CATTATGCCA ATAGGTGTCT TAGTCCCCTA TTGCGTCCTT TCTTGTACAC

7851 AGCAAAAGGC CAGCAAAAGG CCAGGAACCG TAAAAAGGCC GCGTTGCTGG
     TCGTTTTCCG GTCGTTTTCC GGTCCTTGGC ATTTTTCCGG CGCAACGACC

7901 CGTTTTTCCA TAGGCTCCGC CCCCCTGACG AGCATCACAA AAATCGACGC
     GCAAAAAGGT ATCCGAGGCG GGGGGACTGC TCGTAGTGTT TTTAGCTGCG

7951 TCAAGTCAGA GGTGGCGAAA CCCGACAGGA CTATAAAGAT ACCAGGCGTT
     AGTTCAGTCT CCACCGCTTT GGGCTGTCCT GATATTTCTA TGGTCCGCAA

8001 TCCCCCTGGA AGCTCCCTCG TGCGCTCTCC TGTTCCGACC CTGCCGCTTA
     AGGGGGACCT TCGAGGGAGC ACGCGAGAGG ACAAGGCTGG GACGGCGAAT

8051 CCGGATACCT GTCCGCCTTT CTCCCTTCGG GAAGCGTGGC GCTTTCTCAT
     GGCCTATGGA CAGGCGGAAA GAGGGAAGCC CTTCGCACCG CGAAAGAGTA

8101 AGCTCACGCT GTAGGTATCT CAGTTCGGTG TAGGTCGTTC GCTCCAAGCT
     TCGAGTGCGA CATCCATAGA GTCAAGCCAC ATCCAGCAAG CGAGGTTCGA

8151 GGGCTGTGTG CACGAACCCC CCGTTCAGCC CGACCGCTGC GCCTTATCCG
     CCCGACACAC GTGCTTGGGG GGCAAGTCGG GCTGGCGACG CGGAATAGGC

8201 GTAACTATCG TCTTGAGTCC AACCCGGTAA GACACGACTT ATCGCCACTG
     CATTGATAGC AGAACTCAGG TTGGGCCATT CTGTGCTGAA TAGCGGTGAC

8251 GCAGCAGCCA CTGGTAACAG GATTAGCAGA GCGAGGTATG TAGGCGGTGC
     CGTCGTCGGT GACCATTGTC CTAATCGTCT CGCTCCATAC ATCCGCCACG

8301 TACAGAGTTC TTGAAGTGGT GGCCTAACTA CGGCTACACT AGAAGGACAG
     ATGTCTCAAG AACTTCACCA CCGGATTGAT GCCGATGTGA TCTTCCTGTC

8351 TATTTGGTAT CTGCGCTCTG CTGAAGCCAG TTACCTTCGG AAAAAGAGTT
     ATAAACCATA GACGCGAGAC GACTTCGGTC AATGGAAGCC TTTTTCTCAA

8401 GGTAGCTCTT GATCCGGCAA ACAAACCACC GCTGGTAGCG GTGGTTTTTT
     CCATCGAGAA CTAGGCCGTT TGTTTGGTGG CGACCATCGC CACCAAAAAA

8451 TGTTTGCAAG CAGCAGATTA CGCGCAGAAA AAAAGGATCT CAAGAAGATC
     ACAAACGTTC GTCGTCTAAT GCGCGTCTTT TTTTCCTAGA GTTCTTCTAG

8501 CTTTGATCTT TTCTACGGGG TCTGACGCTC AGTGGAACGA AAACTCACGT
     GAAACTAGAA AAGATGCCCC AGACTGCGAG TCACCTTGCT TTTGAGTGCA

8551 TAAGGGATTT TGGTCATGAG ATTATCAAAA AGGATCTTCA CCTAGATCCT
     ATTCCCTAAA ACCAGTACTC TAATAGTTTT TCCTAGAAGT GGATCTAGGA

8601 TTTAAATTAA AAATGAAGTT TTAAATCAAT CTAAAGTATA TATGAGTAAA
     AAATTTAATT TTTACTTCAA AATTTAGTTA GATTTCATAT ATACTCATTT

8651 CTTGGTCTGA CAGTTACCAA TGCTTAATCA GTGAGGCACC TATCTCAGCG
     GAACCAGACT GTCAATGGTT ACGAATTAGT CACTCCGTGG ATAGAGTCGC
```

-continued

```
8701 ATCTGTCTAT TTCGTTCATC CATAGTTGCC TGACTCCCCG TCGTGTAGAT
     TAGACAGATA AAGCAAGTAG GTATCAACGG ACTGAGGGGC AGCACATCTA

8751 AACTACGATA CGGGAGGGCT TACCATCTGG CCCCAGTGCT GCAATGATAC
     TTGATGCTAT GCCCTCCCGA ATGGTAGACC GGGGTCACGA CGTTACTATG

8801 CGCGAGACCC ACGCTCACCG GCTCCAGATT TATCAGCAAT AAACCAGCCA
     GCGCTCTGGG TGCGAGTGGC CGAGGTCTAA ATAGTCGTTA TTTGGTCGGT

8851 GCCGGAAGGG CCGAGCGCAG AAGTGGTCCT GCAACTTTAT CCGCCTCCAT
     CGGCCTTCCC GGCTCGCGTC TTCACCAGGA CGTTGAAATA GGCGGAGGTA

8901 CCAGTCTATT AATTGTTGCC GGGAAGCTAG AGTAAGTAGT TCGCCAGTTA
     GGTCAGATAA TTAACAACGG CCCTTCGATC TCATTCATCA AGCGGTCAAT

8951 ATAGTTTGCG CAACGTTGTT GCCATTGCTA CAGGCATCGT GGTGTCACGC
     TATCAAACGC GTTGCAACAA CGGTAACGAT GTCCGTAGCA CCACAGTGCG

9001 TCGTCGTTTG GTATGGCTTC ATTCAGCTCC GGTTCCCAAC GATCAAGGCG
     AGCAGCAAAC CATACCGAAG TAAGTCGAGG CCAAGGGTTG CTAGTTCCGC

9051 AGTTACATGA TCCCCCATGT TGTGCAAAAA AGCGGTTAGC TCCTTCGGTC
     TCAATGTACT AGGGGGTACA ACACGTTTTT TCGCCAATCG AGGAAGCCAG

9101 CTCCGATCGT TGTCAGAAGT AAGTTGGCCG CAGTGTTATC ACTCATGGTT
     GAGGCTAGCA ACAGTCTTCA TTCAACCGGC GTCACAATAG TGAGTACCAA

9151 ATGGCAGCAC TGCATAATTC TCTTACTGTC ATGCCATCCG TAAGATGCTT
     TACCGTCGTG ACGTATTAAG AGAATGACAG TGCGAGTGGC ATTCTACGAA

9201 TTCTGTGACT GGTGAGTACT CAACCAAGTC ATTCTGAGAA TAGTGTATGC
     AAGACACTGA CCACTCATGA GTTGGTTCAG TAAGACTCTT ATCACATACG

9251 GGCGACCGAG TTGCTCTTGC CCGGCGTCAA TACGGGATAA TACCGCGCCA
     CCGCTGGCTC AACGAGAACG GGCCGCAGTT ATGCCCTATT ATGGCGCGGT

9301 CATAGCAGAA CTTTAAAAGT GCTCATCATT GGAAAACGTT CTTCGGGGCG
     GTATCGTCTT GAAATTTTCA CGAGTAGTAA CCTTTTGCAA GAAGCCCCGC

9351 AAAACTCTCA AGGATCTTAC CGCTGTTGAG ATCCAGTTCG ATGTAACCCA
     TTTTGAGAGT TCCTAGAATG GCGACAACTC TAGGTCAAGC TACATTGGGT

9401 CTCGTGCACC CAACTGATCT TCAGCATCTT TTACTTTCAC CAGCGTTTCT
     GAGCACGTGG GTTGACTAGA AGTCGTAGAA AATGAAAGTG GTCGCAAAGA

9451 GGGTGAGCAA AAACAGGAAG GCAAAATGCC GCAAAAAAGG GAATAAGGGC
     CCCACTCGTT TTTGTCCTTC CGTTTTACGG CGTTTTTTCC CTTATTCCCG

9501 GACACGGAAA TGTTGAATAC TCATACTCTT CCTTTTTCAA TATTAT
     CTGTGCCTTT ACAACTTATG AGTATGAGAA GGAAAAAGTT ATAATA
```

We claim:

1. A fertile transplastomic plant comprising one or more plastids engineered to contain one or more expression cassettes for the plastid-encoded expression of genes encoding enzymes for the production of polyhydroxyalkanoate (PHA),
    wherein the one or more expression cassettes comprise untranslated regions (UTRs) with a sequence length of about 55 nucleotides or fewer, or
    wherein the one or more expression cassettes comprise a total plastidial DNA content of about 3% or less,
    wherein the genes encoding enzymes for the production of PHA have codon usage similar to the plastome of the host plant and are inserted into an existing transcriptional unit of the host plastid, and are under the control of the transcriptional unit, and
    wherein the fertile transplastomic plant produces greater than 10% polyhydroxyalkanoate per unit dry cell weight (dwt) in leaves and produces seeds that are able to germinate and produce viable transplastomic plants.

2. The transplastomic plant of claim 1 wherein the genes are modified or synthesized to improve codon usage for expression in the plastome of the host plant.

3. The transplastomic plant of claim 1 wherein the transgenic plant is engineered to express one or more genes selected from the group consisting of phaA, phaB, and phaC.

4. The transplastomic plant of claim 1 wherein the plant is a dicot or monocot.

5. The transplastomic plant of claim 1 wherein the plant is selected from the group consisting of *B. napus, B. rappa, B. carinata* and *B. juncea; Camelina sativa, Crambe, jatropha*, castor; *Arabidopsis thaliana*; maize; soybean; cottonseed; sunflower; palm; algae; coconut; safflower; peanut; *Sinapis alba*; sugarcane; silage corn; alfalfa; switchgrass; miscanthus; hemp; sorghum; and tobacco.

6. The transplastomic plant of claim 1, where some regions of the leaves of the plant produce greater than 10% dwt PHA.

7. The transplastomic plant of claim 1 wherein PHA levels can reach at least 20% dwt in some regions of leaf.

8. The transplastomic plant of claim 1 wherein the polyhydroxyalkanoate is poly(3-hydroxybutyrate) (P3HB).

9. A seed of the transplastomic plant of claim 1.

10. A biorefinery fuel or energy feedstock comprising plant material or plant parts of the transplastomic plant according to claim 1.

11. The feedstock of claim 10 wherein the feedstock comprises at least about 8% PHB throughout the whole plant.

12. A method for producing a fertile transplastomic plant that produces greater than 10% PHA per unit dwt in its leaves, the method comprising:
    selecting a host plant; and
    transfecting one or more plastids of the host plant with a vector containing one or more expression cassettes for the plastid-encoded expression of genes encoding enzymes for the production of polyhydroxyalkanoate (PHA), the expression cassettes comprising:
    (a) genes encoding enzymes for the production of PHA, wherein the genes are selected for codon usage and GC content similar to the plastome of the host plant, are inserted into an existing transcriptional unit of the host plastid and are under the control of the transcriptional unit;
    (b) untranslated regions (UTRs) with a sequence length of about 55 nucleotides or fewer; and
    (c) a total plastidial DNA content of about 3% or less of the vector excluding a left flank and a right flank that together mediate integration of the vector into the one or more plastids;

wherein the fertile transplastomic plant produces seeds that are able to germinate and produce viable transplastomic plants.

13. The method of claim 12 wherein the polyhydroxyalkanoate comprises P3HB.

14. A method for producing a fertile transplastomic plant that produces PHA in its leaves, the method comprising:
   selecting a host plant; and
   transfecting one or more plastids of the host plant with a vector comprising:
   (a) a left flank and a right flank that together mediate integration of the vector into the one or more plastids;
   (b) genes between the left flank and right flank, wherein the genes encode enzymes for the production of PHA and have codon usage and GC content similar to the plastome of the host plant, and
   (c) one or more untranslated regions (UTRs) which allow a high level of expression of the genes, wherein sequence identity of the one or more UTRs with the host plastome is sufficiently low that, after the vector is integrated into the host plastid, the rate of recombination of the vector sequences with the host plastome is reduced relative to a corresponding host plastid not transfected with the UTRs;
   thereby producing a fertile transplastomic plant that produces greater than 10% polyhydroxyalkanoate per unit dry cell weight (dwt) in its leaves and produces seeds that are able to germinate and produce viable transplastomic plants.

15. The method of claim 14 wherein the polyhydroxyalkanoate comprises P3HB.

16. A fertile transplastomic plant produced according to the method of claim 12.

* * * * *

SEQUENCE LISTING

<160> NUMBER OF SEQ ID NOS: 13

<210> SEQ ID NO 1
<211> LENGTH: 15
<212> TYPE: DNA
<213> ORGANISM: Unknown
<220> FEATURE:
<223> OTHER INFORMATION: Downstream box sequence

<400> SEQUENCE: 1
atggctagca tttcc                                                    15

<210> SEQ ID NO 2
<211> LENGTH: 20
<212> TYPE: DNA
<213> ORGANISM: Artificial Sequence
<220> FEATURE:
<223> OTHER INFORMATION: Synthetc primer KMB41

<400> SEQUENCE: 2

-continued ttgagctgcg ccaaagcctc                                          20

<210> SEQ ID NO 3
<211> LENGTH: 22
<212> TYPE: DNA
<213> ORGANISM: Artificial Sequence
<220> FEATURE:
<223> OTHER INFORMATION: Synthetic KMB77 primer

<400> SEQUENCE: 3
cttgtgctag aactttagct cg                                       22

<210> SEQ ID NO 4
<211> LENGTH: 26
<212> TYPE: DNA
<213> ORGANISM: Artificial Sequence
<220> FEATURE:
<223> OTHER INFORMATION: Synthetic KMB153 primer

<400> SEQUENCE: 4
ccacccatgt ggtacttcat tctacg                                   26

<210> SEQ ID NO 5
<211> LENGTH: 26
<212> TYPE: DNA
<213> ORGANISM: Artificial Sequence
<220> FEATURE:
<223> OTHER INFORMATION: Synthetic KMB 36 primer

<400> SEQUENCE: 5
gagttgtagg gaggcaacca tggcag                                   26

<210> SEQ ID NO 6
<211> LENGTH: 26
<212> TYPE: DNA
<213> ORGANISM: Artificial Sequence
<220> FEATURE:
<223> OTHER INFORMATION: Synthetic KMB 96 primer

<400> SEQUENCE: 6
cttctgtaac tggataacta gcactg                                   26

<210> SEQ ID NO 7
<211> LENGTH: 27
<212> TYPE: DNA
<213> ORGANISM: Artificial Sequence
<220> FEATURE:
<223> OTHER INFORMATION: Synthetic KMB 97 primer

<400> SEQUENCE: 7
gttaccaagg aaccatgcat agcactg                                  27

<210> SEQ ID NO 8
<211> LENGTH: 8746
<212> TYPE: DNA
<213> ORGANISM: Artificial Sequence
<220> FEATURE:
<223> OTHER INFORMATION: Synthetic pUCaadA plasmid (forward strand)

<400> SEQUENCE: 8
aagcatttat cagggttatt gtctcatgag cggatacata tttgaatgta tttagaaaaa    60
taaacaaata ggggttccgc gcacatttcc ccgaaaagtg ccacctgacg tctaagaaac   120
cattattatc atgacattaa cctataaaaa taggcgtatc acgaggccct ttcgtctcgc   180
gcgtttcggt gatgacggtg aaaacctctg acacatgcag ctcccggaga cggtcacagc   240

```
ttgtctgtaa gcggatgccg ggagcagaca agcccgtcag ggcgcgtcag cgggtgttgg      300
cgggtgtcgg ggctggctta actatgcggc atcagagcag attgtactga gagtgcacca      360
tatgcggtgt gaaataccgc acagatgcgt aaggagaaaa taccgcatca ggcgccattc      420
gccattcagg ctgcgcaact gttgggaagg gcgatcggtg cgggcctctt cgctattacg      480
ccagctggcg aaggggggat gtgctgcaag gcgattaagt tgggtaacgc cagggttttc      540
ccagtcacga cgttgtaaaa cgacggccag tgaattcatg actgcaattt tagagagacg      600
cgaaagcgaa agcctatggg gtcgcttctg taactggata actagcactg aaaaccgtct      660
ttacattgga tggtttggtg ttttgatgat ccctacctta ttgacggcaa cttctgtatt      720
tattattgcc ttcattgctg ctcctccagt agacattgat ggtattcgtg aacctgtttc      780
agggtctcta ctttacggaa acaatattat ttccggtgcc attattccta cttctgcagc      840
tataggttta cattttttacc caatctggga agcggcatcc gttgatgaat ggttatacaa      900
cggtggtcct tatgaactaa ttgttctaca cttcttactt ggcgtagctt gttacatggg      960
tcgtgagtgg gagcttagtt ccgtctggga tatgcgacct tggattgctg ttgcatattc     1020
agctcctgtt gcagctgcta ccgcagtttt cttgatctac ccaattggtc aaggaagttt     1080
ttctgatggt atgcctctag gaatctctgg tactttcaat ttcatgattg tattccaggc     1140
tgagcacaac atccttatgc acccatttca catgttaggc gtagctggtg tattcggcgg     1200
ctccctattc agtgctatgc atggttcctt ggtaacttct agtttgatca gggaaaccac     1260
agaaaatgaa tctgctaatg aaggttacag attcggtcaa gaggaagaaa cttataacat     1320
cgtagccgct catggttatt ttggccgatt gatcttccaa tatgctagtt caacaactc      1380 tcgttcgtta cacttcttcc tagctgcttg gcctgtagta ggtatctggt ttaccgcttt     1440
aggtatcagc actatggctt tcaacctaaa tggtttcaat ttcaaccaat ctgtagttga     1500
cagtcaaggc cgtgtaatta atacttgggc tgatatcatt aaccgtgcta accttggtat     1560
ggaagttatg catgaacgta atgctcacaa cttccctcta gacctagctg ctatcgaagc     1620
tccatctaca aatggataag tcgacggtat cgataagctt ccccgggaga ccacaacggt     1680
ttccctctag aaataatttt gtttaacttt aagaaggaga tatacatatg aacccgaact     1740
catttcaatt caaagaaaac atactacaat ttttttctgt acatgatgac atctggaaaa     1800
aattacaaga attttattat gggcaaagcc caattaatga ggctttggcg cagctcaaca     1860
aagaagatat gtctttgttc tttgaagcac tatctaaaaa cccagctcgc atgatggaaa     1920
tgcaatggag ctggtggcaa ggtcaaatac aaatctacca aaatgtgttg atgcgcagcg     1980
tggccaaaga tgtagcacca tttattcagc ctgaaagtgg tgatcgtcgt tttaacagcc     2040
cattatggca agaacaccca aattttgact tgttgtcaca gtcttattta ctgtttagcc     2100
agttagtgca aaacatggta gatgtggtcg aaggtgttcc agacaaagtt cgctatcgta     2160
ttcacttctt tacccgccaa atgatcaatg cgttatctcc aagtaacttt ctgtggacta     2220
acccagaagt gattcagcaa actgtagctg aacaaggtga aaacttagtc cgtggcatgc     2280 aagtttttcca tgatgatgtc atgaatagcg gcaagtattt atctattcgc atggtgaata     2340
gcgactcttt cagcttgggc aaagatttag cttacacccc tggtgcagtc gtctttgaaa     2400
atgacatttt ccaattattg caatatgaag caactactga aaatgtgtat caaaccccta     2460
ttctagtcgt accaccgttt atcaataaat attatgtgct ggatttacgc gaacaaaact     2520
ctttagtgaa ctggttgcgc cagcaaggtc atacagtctt tttaatgtca tggcgtaacc     2580
```

```
caaatgccga acagaaagaa ttgacttttg ccgatctcat tacacaaggt tcagtggaag    2640
ctttgcgtgt aattgaagaa attaccggtg aaaaagaggc caactgcatt ggctactgta    2700
ttggtggtac gttacttgct gcgactcaag cctattacgt ggcaaaacgc ctgaaaaatc    2760
acgtaaagtc tgcgacctat atggccacca ttatcgactt tgaaaaccca ggcagcttag    2820
gtgtatttat taatgaacct gtagtgagcg gtttagaaaa cctgaacaat caattgggtt    2880
atttcgatgg tcgtcagttg gcagttacct tcagtttact gcgtgaaaat acgctgtact    2940
ggaattacta catcgacaac tacttaaaag gtaaagaacc ttctgatttt gatattttat    3000
attggaacag cgatggtacg aatatccctg ccaaaattca taatttctta ttgcgcaatt    3060
tgtatttgaa caatgaattg atttcaccaa atgccgttaa ggttaacggt gtgggcttga    3120
atctatctcg tgtaaaaaca ccaagcttct ttattgcgac gcaggaagac catatcgcac    3180
tttgggatac ttgtttccgt ggcgcagatt acttgggtgg tgaatcaacc ttggttttag    3240
gtgaatctgg acacgtagca ggtattgtca atcctccaag ccgtaataaa tacgttgct     3300
acaccaatgc tgccaagttt gaaaatacca acaatggct agatggcgca gaatatcacc     3360
ctgaatcttg gtggttgcgc tggcaggcat gggtcacacc gtacactggt gaacaagtcc    3420
ctgcccgcaa cttgggtaat gcgcagtatc caagcattga agcggcaccg gtcgctatg     3480
ttttggtaaa tttattctaa gcggccgcca ccgcggtgga gctcaataaa aaaaatctag    3540
atgcttatga ttcagtagta ggaggcaaac catatgaaag atgttgtgat tgttgcagca    3600
aaacgtactg cgattggtag ctttttaggt agtcttgcat ctttatctgc accacagttg    3660
gggcaaacag caattcgtgc agttttagac agcgctaatg taaaacctga acaagttgat    3720
caggtgatta tgggcaacgt actcacgaca ggcgtgggac aaaaccctgc acgtcaggca    3780
gcaattgctg ctggtattcc agtacaagtg cctgcatcta cgctgaatgt cgtctgtggt    3840
tcaggtttgc gtgcggtaca tttggcagca caagccattc aatgcgatga agccgacatt    3900
gtggtcgcag gtggtcaaga atctatgtca caaagtgcgc actatatgca gctgcgtaat    3960
gggcaaaaaa tgggtaatgc acaattggtg gatagcatgg tggctgatgg tttaaccgat    4020
gcctataacc agtatcaaat gggtattacc gcagaaaata ttgtagaaaa actgggttta    4080
aaccgtgaag aacaagatca acttgcattg acttcacaac aacgtgctgc ggcagctcag    4140
gcagctggca gtttaagaga tgaaattgcc gtagtcagca ttccacaacg taaaggtgag    4200
cctgttgtat ttgctgaaga tgaatacatt aaagccaata ccagccttga aagcctcaca    4260
aaactacgcc cagcctttaa aaaagatggt agcgtaaccg caggtaatgc ttcaggcatt    4320
aatgatggtg cagcagcagt actgatgatg agtgcggaca aagcagcaga attaggtctt    4380
aagccattgg cacgtattaa aggctatgcc atgtctggta ttgagcctga aattatgggg    4440
cttggtcctg tcgatgcagt aaagaaaacc ctcaacaaag caggctggag cttagatcag    4500
gttgatttga ttgaagccaa tgaagcattt gctgcacagg ctttgggtgt tgctaaagaa    4560
ttaggcttag acctggataa agtcaacgtc aatgcggtg caattgcatt gggtcaccca    4620
attggggctt caggttgccg tattttggtg actttattac atgaaatgca gcgccgtgat    4680
gccaagaaag gcattgcaac cctctgtgtt ggcggtggta tgggtgttgc acttgcagtt    4740
gaacgtgact aagcggccgc tcgagtttgg atccaatcga tacaagtgag ttgtagggag    4800
gcaaccatgg cagaagcggt gatcgccgaa gtatcgactc aactatcaga ggtagttggc    4860
gtcatcgagc gccatctcga accgacgttg ctggccgtac atttgtacgg ctccgcagtg    4920
gatggcggcc tgaagccaca cagtgatatt gatttgctgg ttacggtgac cgtaaggctt    4980
```

```
gatgaaacaa cgcggcgagc tttgatcaac gacctttgg aaacttcggc ttcccctgga    5040
gagagcgaga ttctccgcgc tgtagaagtc accattgttg tgcacgacga catcattccg    5100
tggcgttatc cagctaagcg cgaactgcaa tttggagaat ggcagcgcaa tgacattctt    5160
gcaggtatct tcgagccagc cacgatcgac attgatctgg ctatcttgct gacaaaagca    5220
agagaacata gcgttgcctt ggtaggtcca gcggcggagg aactctttga tccggttcct    5280
gaacaggatc tatttgaggc gctaaatgaa accttaacgc tatggaactc gccgcccgac    5340
tgggctggcg atgagcgaaa tgtagtgctt acgttgtccc gcatttggta cagcgcagta    5400
accggcaaaa tcgcgccgaa ggatgtcgct gccgactggg caatgagcg cctgccggcc    5460 cagtatcagc ccgtcatact tgaagctaga caggcttatc ttggacaaga agaagatcgc    5520
ttggcctcgc gcgcagatca gttggaagaa tttgtccact acgtgaaagg cgagatcacc    5580
aaggtagtcg gcaaataaat ctaagccgaa ttgggcctag tctataggag gttttgaaaa    5640
gaaaggagca ataatcattt tcttgttcta tcaagagggt gctattgctc ctttcttttt    5700
ttctttttat ttatttacta gtatttact tacatagact ttttgttta cattatagaa    5760 aaagaaggag aggttatttt cttgcattta ttcatgattg agtattctat tttgattttg    5820
tatttgttta aaattgtaga aatagaactt gtttctcttc ttgctaatgt tactatatct    5880
ttttgatttt ttttttccaa aaaaaaaatc aaattttgac ttcttcttat ctcttatctt    5940
tgaatatctc ttatctttga aataataata tcattgaaat aagaaagaag agctatattc    6000
gaacttgaat cttttgtttt ctaatttaaa taatgtaaaa acggaatgta agtaggcgag    6060
ggggcggatg tagccaagtg gatcaaggca gtggattgtg aatccaccat gcgcgggttc    6120
aattcccgtc gttcgcccat aattactcct attttttttt tttttgtaaa acgaagaat    6180 ttaattcgat tttctctcct atttactacg gcgacgaaga atcaaattat cactatattt    6240
attccttttt ctacttcttc ttccaagtgc aggataaccc caaggggttg tgggttttt    6300 tctaccaatt ggggctctcc cttcaccacc cccatgggga tggtctacag ggttcataac    6360
tactcctctt actacaggac gcttacctag ccaacgctta gatccggctc tacccaaact    6420
tttctggttc accccaacat tccccacttg tccgactgtt gctgagcagt ttttggatat    6480
caaacggacc tccccagaag gtaattttaa tgtggccgat tcccctctt ttgcaatcag    6540 tttcgctaca gcaccgctg ctctagctaa ttgtccaccc tttccaagtg tgatttctat    6600
gttatgtatg ccgtgccta agggcatatc ggttgaagta gattcttctt ttgatcaatc    6660
aaaacccctt cccaaactgt acaagcttgg cgtaatcatg gtcatagctg tttcctgtgt    6720
gaaattgtta ccgctcaca attccacaca acatacgagc cggaagcata agtgtaaag    6780 cctggggtgc ctaatgagtg agctaactca cattaattgc gttgcgctca ctgcccgctt    6840
tccagtcggg aaacctgtcg tgccagctgc attaatgaat cggccaacgc gcggggagag    6900
gcggtttgcg tattgggcgc tcttccgctt cctcgctcac tgactcgctg cgctcggtcg    6960
ttcggctgcg gcgagcggta tcagctcact caaaggcggt aatacggtta tccacagaat    7020
caggggataa cgcaggaaag aacatgtgag caaaaggcca gcaaaaggcc aggaaccgta    7080
aaaaggccgc gttgctggcg ttttccata ggctccgccc ccctgacgag catcacaaaa    7140
atcgacgctc aagtcagagg tggcgaaacc cgacaggact ataagatac caggcgtttc    7200 cccctggaag ctccctcgtg cgctctcctg ttccgaccct gccgcttacc ggatacctgt    7260
ccgcctttct cccttcggga agcgtggcgc tttctcatag ctcacgctgt aggtatctca    7320
```

```
gttcggtgta ggtcgttcgc tccaagctgg gctgtgtgca cgaaccccc gttcagcccg      7380
accgctgcgc cttatccggt aactatcgtc ttgagtccaa cccggtaaga cacgacttat      7440
cgccactggc agcagccact ggtaacagga ttagcagagc gaggtatgta ggcggtgcta      7500
cagagttctt gaagtggtgg cctaactacg gctacactag aaggacagta tttggtatct      7560
gcgctctgct gaagccagtt accttcggaa aaagagttgg tagctcttga tccggcaaac      7620
aaaccaccgc tggtagcggt ggtttttttg tttgcaagca gcagattacg cgcagaaaaa      7680
aaggatctca agaagatcct ttgatctttt ctacggggtc tgacgctcag tggaacgaaa      7740
actcacgtta agggattttg gtcatgagat tatcaaaaag gatcttcacc tagatccttt      7800
taaattaaaa atgaagtttt aaatcaatct aaagtatata tgagtaaact tggtctgaca      7860
gttaccaatg cttaatcagt gaggcaccta tctcagcgat ctgtctattt cgttcatcca      7920
tagttgcctg actccccgtc gtgtagataa ctacgatacg ggagggctta ccatctggcc      7980
ccagtgctgc aatgataccg cgagacccac gctcaccggc tccagattta tcagcaataa      8040
accagccagc cggaagggcc gagcgcagaa gtggtcctgc aactttatcc gcctccatcc      8100
agtctattaa ttgttgccgg gaagctagag taagtagttc gccagttaat agtttgcgca      8160
acgttgttgc cattgctaca ggcatcgtgg tgtcacgctc gtcgtttggt atggcttcat      8220
tcagctccgg ttcccaacga tcaaggcgag ttacatgatc ccccatgttg tgcaaaaaag      8280
cggttagctc cttcggtcct ccgatcgttg tcagaagtaa gttggccgca gtgttatcac      8340
tcatggttat ggcagcactg cataattctc ttactgtcat gccatccgta agatgctttt      8400
ctgtgactgg tgagtactca accaagtcat tctgagaata gtgtatgcgg cgaccgagtt      8460
gctcttgccc ggcgtcaata cgggataata ccgcgccaca tagcagaact ttaaaagtgc      8520
tcatcattgg aaaacgttct cggggcgaaa actctcaag gatcttaccg ctgttgagat      8580
ccagttcgat gtaacccact cgtgcaccca actgatcttc agcatctttt actttcacca      8640
gcgtttctgg gtgagcaaaa acaggaaggc aaaatgccgc aaaaaaggga ataagggcga      8700
cacggaaatg ttgaatactc atactcttcc ttttcaata ttattg                     8746
```

<210> SEQ ID NO 9
<211> LENGTH: 8746
<212> TYPE: DNA
<213> ORGANISM: Artificial Sequence
<220> FEATURE:
<223> OTHER INFORMATION: Synthetic pUCaadA plasmid (reverse strand)

<400> SEQUENCE: 9

```
ttcgtaaata gtcccaataa cagagtactc gcctatgtat aaacttacat aaatcttttt       60
atttgtttat ccccaaggcg cgtgtaaagg ggcttttcac ggtggactgc agattctttg      120
gtaataatag tactgtaatt ggatattttt atccgcatag tgctccggga aagcagagcg      180
cgcaaagcca ctactgccac tttttggaga ctgtgtacgtc gagggcctct gccagtgtcg      240
aacagacatt cgcctacggc cctcgtctgt tcgggcagtc ccgcgcagtc gcccacaacc      300
gcccacagcc ccgaccgaat tgatacgccg tagtctcgtc taacatgact ctcacgtggt      360
atacgccaca ctttatggcg tgtctacgca ttcctctttt atggcgtagt ccgcggtaag      420
cggtaagtcc gacgcgttga caacccttcc cgctagccac gcccggagaa gcgataatgc      480
ggtcgaccgc tttcccccta cacgacgttc cgctaattca acccattgcg gtcccaaaag      540
ggtcagtgct gcaacatttt gctgccggtc acttaagtac tgacgttaaa atctctctgc      600
gctttcgctt tcggataccc cagcgaagac attgacctat tgatcgtgac ttttggcaga      660
```

```
aatgtaacct accaaaccac aaaactacta gggatggaat aactgccgtt gaagacataa      720
ataataacgg aagtaacgac gaggaggtca tctgtaacta ccataagcac ttggacaaag      780
tcccagagat gaaatgcctt tgttataata aaggccacgg taataaggat gaagacgtcg      840
atatccaaat gtaaaaatgg gttagaccct tcgccgtagg caactactta ccaatatgtt      900
gccaccagga atacttgatt aacaagatgt gaagaatgaa ccgcatcgaa caatgtaccc      960
agcactcacc ctcgaatcaa aggcagaccc atacgctgga acctaacgac aacgtataag     1020
tcgaggacaa cgtcgacgat ggcgtcaaaa gaactagatg ggttaaccag ttccttcaaa     1080
aagactacca tacggagatc cttagagacc atgaaagtta aagtactaac ataaggtccg     1140
actcgtgttg taggaatacg tgggtaaagt gtacaatccg catcgaccac ataagccgcc     1200
gagggataag tcacgatacg taccaaggaa ccattgaaga tcaaactagt cccctttggtg    1260 tcttttactt agacgattac ttccaatgtc taagccagtt ctccttcttt gaatattgta     1320
gcatcggcga gtaccaataa aaccggctaa ctagaaggtt atacgatcaa agttgttgag     1380
agcaagcaat gtgaagaagg atcgacgaac cggacatcat ccatagacca aatggcgaaa     1440
tccatagtcg tgataccgaa agttggattt accaaagtta aagttggtta gacatcaact     1500
gtcagttccg gcacattaat tatgaacccg actatagtaa ttggcacgat tggaaccata     1560
ccttcaatac gtacttgcat tacgagtgtt gaagggagag ctggatcgac gatagcttcg     1620
aggtagatgt ttacctattc agctgccata gctattcgaa ggggccctct ggtgttgcca     1680
aagggagatc tttattaaaa caaattgaaa ttcttcctct atatgtatac ttgggcttga     1740
gtaaagttaa gtttctttg tatgatgtta aaaaagaca tgtactactg tagaccttt       1800 ttaatgttct taaaataata cccgtttcgg gttaattact ccgaaaccgc gtcgagttgt     1860
ttcttctata cagaaacaag aaacttcgtg atagatttt gggtcgagcg tactacctt       1920 acgttacctc gaccaccgtt ccagtttatg tttagatggt tttacacaac tacgcgtcgc     1980
accggtttct acatcgtggt aaataagtcg gactttcacc actagcagca aaattgtcgg     2040
gtaataccgt tcttgtgggt ttaaaactga acaacagtgt cagaataaat gacaaatcgg     2100
tcaatcacgt tttgtaccat ctacaccagc ttccacaagg tctgtttcaa gcgatagcat     2160
aagtgaagaa atgggcggtt tactagttac gcaatagagg ttcattgaaa gacacctgat     2220
tgggtcttca ctaagtcgtt tgacatcgac ttgttccact tttgaatcag gcaccgtacg     2280
ttcaaaaggt actactacag tacttatcgc cgttcataaa tagataagcg taccacttat     2340
cgctgagaaa gtcgaacccg tttctaaatc gaatgtgggg accacgtcag cagaaacttt     2400
tactgtaaaa ggttaataac gttatacttc gttgatgact tttacacata gtttggggat     2460
aagatcagca tggtggcaaa tagttatta taatacacga cctaaatgcg cttgttttga      2520
gaaatcactt gaccaacgcg gtcgttccag tatgtcagaa aaattacagt accgcattgg     2580
gtttacggct tgtctttctt aactgaaaac ggctagagta atgtgttcca agtcaccttc     2640
gaaacgcaca ttaacttctt taatggccac tttttctccg gttgacgtaa ccgatgacat     2700
aaccaccatg caatgaacga cgctgagttc ggataatgca ccgttttgcg gacttttag      2760 tgcatttcag acgctggata taccggtggt aatagctgaa actttgggt ccgtcgaatc      2820 cacataaata attacttgga catcactcgc caaatctttt ggacttgtta gttaacccaa     2880
taaagctacc agcagtcaac cgtcaatgga agtcaaatga cgcacttta tgcgacatga      2940 ccttaatgat gtagctgttg atgaattttc catttcttgg aagactaaaa ctataaaata     3000
```

```
taaccttgtc gctaccatgc ttatagggac ggttttaagt attaaagaat aacgcgttaa    3060
acataaactt gttacttaac taaagtggtt tacggcaatt ccaattgcca cacccgaact    3120
tagatagagc acatttttgt ggttcgaaga ataacgctg cgtccttctg gtatagcgtg     3180
aaaccctatg aacaaggca ccgcgtctaa tgaacccacc acttagttgg aaccaaaatc     3240
cacttagacc tgtgcatcgt ccataacagt taggaggttc ggcattattt atgccaacga    3300
tgtggttacg acggttcaaa cttttatggt ttgttaccga tctaccgcgt cttatagtgg    3360
gacttagaac caccaacgcg accgtccgta cccagtgtgg catgtgacca cttgttcagg    3420
gacgggcgtt gaacccatta cgcgtcatag gttcgtaact tcgccgtggc ccagcgatac    3480
aaaaccattt aataagatt cgccggcggt ggcgccacct cgagttattt ttttttagatc    3540 tacgaatact aagtcatcat cctccgtttg gtatactttc tacaacacta caacgtcgt     3600 tttgcatgac gctaaccatc gaaaaatcca tcagaacgta gaaatagacg tggtgtcaac    3660 cccgttgtc gttaagcacg tcaaaatctg tcgcgattac attttggact tgttcaacta    3720
gtccactaat acccgttgca tgagtgctgt ccgcaccctg ttttgggacg tgcagtccgt    3780
cgttaacgac gaccataagg tcatgttcac ggacgtagat gcgacttaca gcagacacca    3840
agtccaaacg cacgccatgt aaaccgtcgt gttcggtaag ttacgctact tcggctgtaa    3900
caccagcgtc caccagttct tagatacagt gtttcacgcg tgatatacgt cgacgcatta    3960
cccgtttttt acccattacg tgttaaccac ctatcgtacc accgactacc aaattggcta    4020
cggatattgg tcatagttta cccataatgg cgtcttttat aacatctttt tgacccaaat    4080
ttggcacttc ttgttctagt tgaacgtaac tgaagtgttg ttgcacgacg ccgtcgagtc    4140
cgtcgaccgt tcaaatttct actttaacgg catcagtcgt aaggtgttgc atttccactc    4200
ggacaacata aacgacttct acttatgtaa tttcggttat ggtcggaact ttcggagtgt    4260
tttgatgcgg gtcggaaatt ttttctacca tcgcattggc gtccattacg aagtccgtaa    4320
ttactaccac gtcgtcgtca tgactactac tcacgcctgt ttcgtcgtct taatccagaa    4380
ttcggtaacc gtgcataatt tccgatacgg tacagaccat aactcggact ttaatacccc    4440
gaaccaggac agctacgtca tttcttttgg gagttgtttc gtccgacctc gaatctagtc    4500
caactaaact aacttcggtt acttcgtaaa cgacgtgtcc gaaacccaca acgatttctt    4560
aatccgaatc tggacctatt tcagttgcag ttaccgccac gttaacgtaa cccagtgggt    4620
taaccccgaa gtccaacggc ataaaaccac tgaaataatg tactttacgt cgcggcacta    4680
cggttctttc cgtaacgttg ggagacacaa ccgccaccat acccacaacg tgaacgtcaa    4740
cttgcactga ttcgccggcg agctcaaacc taggttagct atgttcactc aacatccctc    4800
cgttggtacc gtcttcgcca ctagcggctt catagctgag ttgatagtct ccatcaaccg    4860
cagtagctcg cggtagagct tggctgcaac gaccggcatg taaacatgcc gaggcgtcac    4920
ctaccgccgg acttcggtgt gtcactataa ctaaacgacc aatgccactg gcattccgaa    4980
ctactttgtt gcgccgctcg aaactagttg ctggaaaacc tttgaagccg aaggggacct    5040
ctctcgctct aagaggcgcg acatcttcag tggtaacaac acgtgctgct gtagtaaggc    5100
accgcaatag gtcgattcgc gcttgacgtt aaacctctta ccgtcgcgtt actgtaagaa    5160
cgtccataga agctcggtcg gtgctagctg taactagacc gatagaacga ctgttttcgt    5220
tctcttgtat cgcaacggaa ccatccaggt cgccgcctcc ttgagaaact aggccaagga    5280
cttgtcctag ataaactccg cgatttactt tggaattgcg ataccttgag cggcgggctg    5340
acccgaccgc tactcgcttt acatcacgaa tgcaacaggg cgtaaaccat gtcgcgtcat    5400
```

```
tggccgtttt agcgcggctt cctacagcga cggctgaccc gttacctcgc ggacggccgg    5460
gtcatagtcg ggcagtatga acttcgatct gtccgaatag aacctgttct tcttctagcg    5520
aaccggagcg cgcgtctagt caaccttctt aaacaggtga tgcactttcc gctctagtgg    5580
ttccatcagc cgtttattta gattcggctt aacccggatc agatatcctc caaaactttt    5640
ctttcctcgt tattagtaaa agaacaagat agttctccca cgataacgag gaaagaaaaa    5700
aagaaaaata aataaatgat cataaaatga atgtatctga aaaacaaat gtaatatctt    5760 tttcttcctc tccaataaaa gaacgtaaat aagtactaac tcataagata aaactaaaac    5820
ataaacaaat tttaacatct ttatcttgaa caaagagaag aacgattaca atgatataga    5880
aaaactaaaa aaaaaaggtt ttttttttag tttaaaactg aagaagaata gagaatagaa    5940
acttatagag aatagaaact ttattattat agtaacttta ttctttcttc tcgatataag    6000
cttgaactta gaaaacaaaa gattaaattt attacatttt tgccttacat tcatccgctc    6060
ccccgcctac atcggttcac ctagttccgt cacctaacac ttaggtggta cgcgcccaag    6120
ttaagggcag caagcgggta ttaatgagga taaaaaaaaa aaaacatttt ttgcttctta    6180
aattaagcta aaagagagga taaatgatgc cgctgcttct tagtttaata gtgatataaa    6240
taaggaaaaa gatgaagaag aaggttcacg tcctattggg gttccccaac acccaaaaaa    6300
agatggttaa ccccgagagg gaagtggtgg gggtaccect accagatgtc ccaagtattg    6360
atgaggagaa tgatgtcctg cgaatggatc ggttgcgaat ctaggccgag atgggtttga    6420
aaagaccaag tggggttgta aggggtgaac aggctgacaa cgactcgtca aaaacctata    6480
gtttgcctgg aggggtcttc cattaaaatt acaccggcta aaggggagaa aacgttagtc    6540
aaagcgatgt cgtgggcgac gagatcgatt aacaggtggg aaaggttcac actaaagata    6600
caatacatac cggcacggat tcccgtatag ccaacttcat ctaagaagaa aactagttag    6660
ttttggggaa gggtttgaca tgttcgaacc gcattagtac cagtatcgac aaaggacaca    6720
ctttaacaat aggcgagtgt taaggtgtgt tgtatgctcg gccttcgtat ttcacatttc    6780
ggaccccacg gattactcac tcgattgagt gtaattaacg caacgcgagt gacgggcgaa    6840
aggtcagccc tttggacagc acggtcgacg taattactta gccggttgcg cgcccctctc    6900
cgccaaacgc ataacccgcg agaaggcgaa ggagcgagtg actgagcgac gcgagccagc    6960
aagccgacgc cgctcgccat agtcgagtga gtttccgcca ttatgccaat aggtgtctta    7020
gtcccctatt gcgtcctttc ttgtacactc gttttccggt cgttttccgg tccttggcat    7080
ttttccggcg caacgaccgc aaaaaggtat ccgaggcggg gggactgctc gtagtgtttt    7140
tagctgcgag ttcagtctcc accgctttgg gctgtcctga tatttctatg gtccgcaaag    7200
ggggaccttc gagggagcac gcgagaggac aaggctggga cggcgaatgg cctatggaca    7260
ggcggaaaga gggaagccct tcgcaccgcg aaagagtatc gagtgcgaca tccatagagt    7320
caagccacat ccagcaagcg aggttcgacc cgacacacgt gcttgggggg caagtcgggc    7380
tggcgacgcg gaataggcca ttgatagcag aactcaggtt gggccattct gtgctgaata    7440
gcggtgaccg tcgtcggtga ccattgtcct aatcgtctcg ctccatacat ccgccacgat    7500
gtctcaagaa cttcaccacc ggattgatgc cgatgtgatc ttcctgtcat aaaccataga    7560
cgcgagacga cttcggtcaa tggaagcctt tttctcaacc atcgagaact aggccgtttg    7620
tttggtggcg accatcgcca ccaaaaaaac aaacgttcgt cgtctaatgc gcgtcttttt    7680
ttcctagagt tcttctagga aactagaaaa gatgccccag actgcgagtc accttgcttt    7740
```

```
tgagtgcaat tccctaaaac cagtactcta atagttttc ctagaagtgg atctaggaaa      7800
atttaatttt tacttcaaaa tttagttaga tttcatatat actcatttga accagactgt      7860
caatggttac gaattagtca ctccgtggat agagtcgcta gacagataaa gcaagtaggt      7920
atcaacggac tgaggggcag cacatctatt gatgctatgc cctcccgaat ggtagaccgg      7980
ggtcacgacg ttactatggc gctctgggtg cgagtggccg aggtctaaat agtcgttatt      8040
tggtcggtcg gccttccgg ctcgcgtctt caccaggacg ttgaaatagg cggaggtagg      8100
tcagataatt aacaacggcc cttcgatctc attcatcaag cggtcaatta tcaaacgcgt      8160
tgcaacaacg gtaacgatgt ccgtagcacc acagtgcgag cagcaaacca taccgaagta      8220
agtcgaggcc aagggttgct agttccgctc aatgtactag ggggtacaac acgttttttc      8280
gccaatcgag gaagccagga ggctagcaac agtcttcatt caaccggcgt cacaatagtg      8340
agtaccaata ccgtcgtgac gtattaagag aatgacagta cggtaggcat tctacgaaaa      8400
gacactgacc actcatgagt tggttcagta agactcttat cacatacgcc gctggctcaa      8460
cgagaacggg ccgcagttat gccctattat ggcgcggtgt atcgtcttga aattttcacg      8520
agtagtaacc ttttgcaaga agccccgctt ttgagagttc ctagaatggc gacaactcta      8580
ggtcaagcta cattgggtga gcacgtgggt tgactagaag tcgtagaaaa tgaaagtggt      8640
cgcaaagacc cactcgtttt tgtccttccg ttttacggcg ttttttccct tattcccgct      8700
gtgcctttac aacttatgag tatgagaagg aaaaagttat aataac                    8746
```

<210> SEQ ID NO 10
<211> LENGTH: 8796
<212> TYPE: DNA
<213> ORGANISM: Artificial Sequence
<220> FEATURE:
<223> OTHER INFORMATION: Synthetic p(CA)2 primer (forward strand)

<400> SEQUENCE: 10

```
aagcatttat cagggttatt gtctcatgag cggatacata tttgaatgta tttagaaaaa        60
taaacaaata ggggttccgc gcacatttcc ccgaaaagtg ccacctgacg tctaagaaac       120
cattattatc atgacattaa cctataaaaa taggcgtatc acgaggccct ttcgtctcgc       180
gcgtttcggt gatgacggtg aaaacctctg acacatgcag ctcccggaga cggtcacagc       240
ttgtctgtaa gcggatgccg ggagcagaca agcccgtcag ggcgcgtcag cgggtgttgg       300
cgggtgtcgg ggctggctta actatgcggc atcagagcag attgtactga gagtgcacca       360
tatgcggtgt gaaataccgc acagatgcgt aaggagaaaa taccgcatca ggcgccattc       420
gccattcagg ctgcgcaact gttgggaagg gcgatcggtg cgggcctctt cgctattacg       480
ccagctggcg aaagggggat gtgctgcaag gcgattaagt tgggtaacgc cagggttttc       540
ccagtcacga cgttgtaaaa cgacggccag tgaattcatg actgcaattt tagagagacg       600
cgaaagcgaa agcctatggg gtcgcttctg taactggata actagcactg aaaaccgtct       660
ttacattgga tggtttggtg ttttgatgat ccctacctta ttgacggcaa cttctgtatt       720
tattattgcc ttcattgctg ctcctccagt agacattgat ggtattcgtg aacctgtttc       780
agggtctcta ctttacggaa acaatattat ttccggtgcc attattccta cttctgcagc       840
tataggttta cattttacc caatctggga agcggcatcc gttgatgaat ggttatacaa       900
cggtggtcct tatgaactaa ttgttctaca cttcttactt ggcgtagctt gttacatggg       960
tcgtgagtgg gagcttagtt tccgtctggg tatgcgacct tggattgctg ttgcatattc      1020
agctcctgtt gcagctgcta ccgcagtttt cttgatctac ccaattggtc aaggaagttt      1080
```

```
ttctgatggt atgcctctag gaatctctgg tactttcaat tcatgattg tattccaggc    1140 tgagcacaac atccttatgc acccatttca catgttaggc gtagctggtg tattcggcgg    1200
ctccctattc agtgctatgc atggttcctt ggtaacttct agtttgatca gggaaaccac    1260
agaaaatgaa tctgctaatg aaggttacag attcggtcaa gaggaagaaa cttataacat    1320
cgtagccgct catggttatt ttggccgatt gatcttccaa tatgctagtt caacaactc    1380 tcgttcgtta cacttcttcc tagctgcttg gcctgtagta ggtatctggt ttaccgcttt    1440
aggtatcagc actatggctt tcaacctaaa tggtttcaat ttcaaccaat ctgtagttga    1500
cagtcaaggc cgtgtaatta atacttgggc tgatatcatt aaccgtgcta accttggtat    1560
ggaagttatg catgaacgta atgctcacaa cttccctcta gacctagctg ctatcgaagc    1620
tccatctaca aatggataag tcgacggtat cgataagctt ccccgggaga ccacaacggt    1680
ttccctctag aaataatttt gtttaacttt aagaaggaga tatacatatg aacccgaact    1740
catttcaatt caaagaaaac atactacaat ttttttctgt acatgatgac atctggaaaa    1800
aattacaaga attttattat gggcaaagcc caattaatga ggctttggcg cagctcaaca    1860
aagaagatat gtctttgttc tttgaagcac tatctaaaaa cccagctcgc atgatggaaa    1920
tgcaatggag ctggtggcaa ggtcaaatac aaatctacca aaatgtgttg atgcgcagcg    1980
tggccaaaga tgtagcacca tttattcagc ctgaaagtgg tgatcgtcgt tttaacagcc    2040
cattatggca agaacaccca aatttgact tgttgtcaca gtcttattta ctgtttagcc    2100
agttagtgca aaacatggta gatgtggtcg aaggtgttcc agacaaagtt cgctatcgta    2160
ttcacttctt tacccgccaa atgatcaatg cgttatctcc aagtaacttt ctgtggacta    2220
acccagaagt gattcagcaa actgtagctg aacaaggtga aaacttagtc cgtggcatgc    2280
aagttttcca tgatgatgtc atgaatagcg gcaagtattt atctattcgc atggtgaata    2340
gcgactcttt cagcttgggc aaagatttag cttacacccc tggtgcagtc gtctttgaaa    2400
atgacatttt ccaattattg caatatgaag caactactga aaatgtgtat caaacccta    2460 ttctagtcgt accaccgttt atcaataaat attatgtgct ggatttacgc gaacaaaact    2520
ctttagtgaa ctggttgcgc cagcaaggtc atacagtctt tttaatgtca tggcgtaacc    2580
caaatgccga acagaaagaa ttgacttttg ccgatctcat tacacaaggt tcagtggaag    2640
ctttgcgtgt aattgaagaa attaccggtg aaaaagaggc caactgcatt ggctactgta    2700
ttggtggtac gttacttgct gcgactcaag cctattacgt ggcaaaacgc ctgaaaaatc    2760
acgtaaagtc tgcgacctat atggccacca ttatcgactt tgaaacccca ggcagcttag    2820
gtgtatttat taatgaacct gtagtgagcg gtttagaaaa cctgaacaat caattgggtt    2880
atttcgatgg tcgtcagttg gcagttacct tcagttact gcgtgaaaat acgctgtact    2940
ggaattacta cgtcaatgga agtcaaatga cgcacttta tgcgacatga ccttaatgat    3000
catcgacaac tacttaaaag gtaaagaacc ttctgatttt gatatttat attggaacag    3060 cgatggtacg aatatccctg ccaaaattca taatttctta ttgcgcaatt tgtatttgaa    3120
caatgaattg atttcaccaa atgccgttaa ggttaacggt gtgggcttga atctatctcg    3180
tgtaaaaaca ccaagcttct ttattgcgac gcaggaagac catatcgcac tttgggatac    3240
ttgtttccgt ggcgcagatt acttgggtgg tgaatcaacc ttggttttag gtgaatctgg    3300
acacgtagca ggtattgtca atcctccaag ccgtaataaa tacggttgct acaccaatgc    3360
tgccaagttt gaaaatacca aacaatggct agatggcgca gaatatcacc ctgaatcttg    3420
```

```
gtggttgcgc tggcaggcat gggtcacacc gtacactggt gaacaagtcc ctgcccgcaa      3480
cttgggtaat gcgcagtatc caagcattga agcggcaccg ggtcgctatg ttttggtaaa      3540
tttattctaa gcggccgcca ccgcggtgga gctcaataaa aaaaatctag atgcttatga      3600
ttcagtagta ggaggcaaac catatgaaag atgttgtgat tgttgcagca aaacgtactg      3660
cgattggtag cttttttaggt agtcttgcat ctttatctgc accacagttg gggcaaacag      3720
caattcgtgc agttttagac agcgctaatg taaaacctga acaagttgat caggtgatta      3780
tgggcaacgt actcacgaca ggcgtgggac aaaaccctgc acgtcaggca gcaattgctg      3840
ctggtattcc agtacaagtg cctgcatcta cgctgaatgt cgtctgtggt tcaggtttgc      3900
gtgcggtaca tttggcagca caagccattc aatgcgatga agccgacatt gtggtcgcag      3960
gtggtcaaga atctatgtca caaagtgcgc actatatgca gctgcgtaat gggcaaaaaa      4020
tgggtaatgc acaattggtg gatagcatgg tggctgatgg tttaaccgat gcctataacc      4080
agtatcaaat gggtattacc gcagaaaata ttgtagaaaa actgggttta aaccgtgaag      4140
aacaagatca acttgcattg acttcacaac aacgtgctgc ggcagctcag gcagctggca      4200
agtttaaaga tgaaattgcc gtagtcagca ttccacaacg taaaggtgag cctgttgtat      4260
ttgctgaaga tgaatacatt aaagccaata ccagccttga aagcctcaca aaactacgcc      4320
cagcctttaa aaaagatggt agcgtaaccg caggtaatgc ttcaggcatt aatgatggtg      4380
cagcagcagt actgatgatg agtgcggaca agcagcaga attaggtctt aagccattgg      4440
cacgtattaa aggctatgcc atgtctggta ttgagcctga aattatgggg cttggtcctg      4500
tcgatgcagt aaagaaaacc ctcaacaaag caggctggag cttagatcag gttgatttga      4560
ttgaagccaa tgaagcattt gctgcacagg ctttgggtgt tgctaaagaa ttaggcttag      4620
acctggataa agtcaacgtc aatggcggtg caattgcatt gggtcaccca attggggctt      4680
caggttgccg tatttggtg actttattac atgaaatgca gcgccgtgat gccaagaaag      4740
gcattgcaac cctctgtgtt ggcggtggta tgggtgttgc acttgcagtt gaacgtgact      4800
aagcggccgc tcgagtttgg atccaatcga tacaagtgag ttgtagggag caaccatgg      4860 cagaagcggt gatcgccgaa gtatcgactc aactatcaga ggtagttggc gtcatcgagc      4920
gccatctcga accgacgttg ctggccgtac atttgtacgg ctccgcagtg gatggcggcc      4980
tgaagccaca cagtgatatt gatttgctgg ttacggtgac cgtaaggctt gatgaaacaa      5040
cgcggcgagc tttgatcaac gaccttttgg aaacttcggc ttcccctgga gagagcgaga      5100
ttctccgcgc tgtagaagtc accattgttg tgcacgacga catcattccg tggcgttatc      5160
cagctaagcg cgaactgcaa tttggagaat ggcagcgcaa tgacattctt gcaggtatct      5220
tcgagccagc cacgatcgac attgatctgg ctatcttgct gacaaaagca agagaacata      5280
gcgttgcctt ggtaggtcca gcggcggagg aactctttga tccggttcct gaacaggatc      5340
tatttgaggc gctaaatgaa accttaacgc tatggaactc gccgcccgac tgggctggcg      5400
atgagcgaaa tgtagtgctt acgttgtccc gcatttggta cagcgcagta accggcaaaa      5460
tcgcgccgaa ggatgtcgct gccgactggg caatggagcg cctgccggcc cagtatcagc      5520
ccgtcatact tgaagctaga caggcttatc ttggacaaga agaagatcgc ttggcctcgc      5580
gcgcagatca gttggaagaa tttgtccact acgtgaaagg cgagatcacc aaggtagtcg      5640
gcaaataaat ctaagccgaa ttgggcctag tctataggag gttttgaaaa gaaaggagca      5700
ataatcattt tcttgttcta tcaagagggt gctattgctc ctttcttttt ttcttttttat      5760 ttatttacta gtattttact tacatagact ttttttgttta cattatagaa aaagaaggag      5820
```

```
aggttatttt cttgcattta ttcatgattg agtattctat tttgattttg tatttgttta    5880
aaattgtaga aatagaactt gtttctcttc ttgctaatgt tactatatct ttttgatttt    5940 tttttttccaa aaaaaaaatc aaattttgac ttcttcttat ctcttatctt tgaatatctc   6000
ttatctttga aataataata tcattgaaat aagaaagaag agctatattc gaacttgaat    6060
cttttgtttt ctaatttaaa taatgtaaaa acggaatgta agtaggcgag ggggcggatg    6120
tagccaagtg gatcaaggca gtggattgtg aatccaccat cgcgggttc aattcccgtc     6180 gttcgcccat aattactcct atttttttt tttttgtaaa aacgaagaat ttaattcgat     6240
tttctctcct atttactacg gcgacgaaga atcaaattat cactatattt attccttttt    6300
ctacttcttc ttccaagtgc aggataaccc caaggggttg tgggttttt tctaccaatt     6360 ggggctctcc cttcaccacc cccatgggga tggtctacag ggttcataac tactcctctt    6420
actacaggac gcttacctag ccaacgctta gatccggctc tacccaaact tttctggttc    6480
accccaacat tccccacttg tccgactgtt gctgagcagt ttttggatat caaacggacc    6540
tccccagaag gtaatttta tgtggccgat ttcccctctt ttgcaatcag tttcgctaca     6600
gcacccgctg ctctagctaa ttgtccaccc tttccaagtg tgatttctat gttatgtatg    6660
gccgtgccta agggcatatc ggttgaagta gattcttctt ttgatcaatc aaaacccctt    6720
cccaaactgt acaagcttgg cgtaatcatg gtcatagctg tttcctgtgt gaaattgtta    6780
tccgctcaca attccacaca acatacgagc cggaagcata aagtgtaaag cctggggtgc    6840
ctaatgagtg agctaactca cattaattgc gttgcgctca ctgcccgctt tccagtcggg    6900
aaacctgtcg tgccagctgc attaatgaat cggccaacgc gcggggagag gcggtttgcg    6960
tattgggcgc tcttccgctt cctcgctcac tgactcgctg cgctcggtcg ttcggctgcg    7020
gcgagcggta tcagctcact caaaggcggt aatacggtta tccacagaat cagggataa    7080 cgcaggaaag aacatgtgag caaaaggcca gcaaaaggcc aggaaccgta aaaaggccgc    7140
gttgctggcg ttttccata ggctccgccc ccctgacgag catcacaaaa atcgacgctc      7200
aagtcagagg tggcgaaacc cgacaggact ataaagatac caggcgtttc ccctggaag     7260 ctccctcgtg cgctctcctg ttccgaccct gccgcttacc ggatacctgt ccgcctttct    7320
cccttcggga agcgtggcgc tttctcatag ctcacgctgt aggtatctca gttcggtgta    7380
ggtcgttcgc tccaagctgg gctgtgtgca cgaaccccc gttcagcccg accgctgcgc      7440
cttatccggt aactatcgtc ttgagtccaa cccggtaaga cacgacttat cgccactggc    7500
agcagccact ggtaacagga ttagcagagc gaggtatgta ggcggtgcta cagagttctt    7560
gaagtggtgg cctaactacg gctacactag aaggacagta tttggtatct gcgctctgct    7620
gaagccagtt accttcggaa aaagagttgg tagctcttga tccggcaaac aaaccaccgc    7680
tggtagcggt ggttttttg tttgcaagca gcagattacg cgcagaaaaa aaggatctca     7740
agaagatcct ttgatctttt ctacggggtc tgacgctcag tggaacgaaa actcacgtta    7800
agggattttg gtcatgagat tatcaaaaag gatcttcacc tagatccttt taaattaaaa    7860
atgaagtttt aaatcaatct aaagtatata tgagtaaact tggtctgaca gttaccaatg    7920
cttaatcagt gaggcaccta tctcagcgat ctgtctattt cgttcatcca tagttgcctg    7980
actccccgtc gtgtagataa ctacgatacg ggagggctta ccatctggcc ccagtgctgc    8040
aatgataccg cgagacccac gctcaccggc tccagattta tcagcaataa accagccagc    8100
cggaagggcc gagcgcagaa gtggtcctgc aactttatcc gcctccatcc agtctattaa    8160
```

-continued

```
ttgttgccgg gaagctagag taagtagttc gccagttaat agtttgcgca acgttgttgc    8220
cattgctaca ggcatcgtgg tgtcacgctc gtcgtttggt atggcttcat tcagctccgg    8280
ttcccaacga tcaaggcgag ttacatgatc ccccatgttg tgcaaaaaag cggttagctc    8340
cttcggtcct ccgatcgttg tcagaagtaa gttggccgca gtgttatcac tcatggttat    8400
ggcagcactg cataattctc ttactgtcat gccatccgta agatgctttt ctgtgactgg    8460
tgagtactca accaagtcat tctgagaata gtgtatgcgg cgaccgagtt gctcttgccc    8520
ggcgtcaata cgggataata ccgcgccaca tagcagaact ttaaaagtgc tcatcattgg    8580
aaaacgttct cgggggcgaa aactctcaag gatcttaccg ctgttgagat ccagttcgat    8640
gtaacccact cgtgcaccca actgatcttc agcatctttt actttcacca gcgtttctgg    8700
gtgagcaaaa acaggaaggc aaaatgccgc aaaaaaggga ataagggcga cacggaaatg    8760
ttgaatactc atactcttcc tttttcaata ttattg                              8796
```

<210> SEQ ID NO 11
<211> LENGTH: 8746
<212> TYPE: DNA
<213> ORGANISM: Artificial Sequence
<220> FEATURE:
<223> OTHER INFORMATION: Synthetic p(CA)2 primer (reverse strand)

<400> SEQUENCE: 11

```
ttcgtaaata gtcccaataa cagagtactc gcctatgtat aaacttacat aaatcttttt      60
atttgtttat ccccaaggcg cgtgtaaagg ggcttttcac ggtggactgc agattctttg     120
gtaataatag tactgtaatt ggatattttt atccgcatag tgctccggga aagcagagcg     180
cgcaaagcca ctactgccac ttttggagac tgtgtacgtc gagggcctct gccagtgtcg     240
aacagacatt cgcctacggc cctcgtctgt tcgggcagtc ccgcgcagtc gcccacaacc     300
gcccacagcc ccgaccgaat tgatacgccg tagtctcgtc taacatgact ctcacgtggt     360
atacgccaca ctttatggcg tgtctacgca ttcctctttt atggcgtagt ccgcggtaag     420
cggtaagtcc gacgcgttga caacccttcc cgctagccac gcccggagaa gcgataatgc     480
ggtcgaccgc tttcccccta cacgacgttc cgctaattca acccattgcg gtcccaaaag     540
ggtcagtgct gcaacatttt gctgccggtc acttaagtac tgacgttaaa atctctctgc     600
gctttcgctt tcggataccc cagcgaagac attgacctat tgatcgtgac ttttggcaga     660
aatgtaacct accaaaccac aaaactacta gggatggaat aactgccgtt gaagacataa     720
ataataacgg aagtaacgac gaggaggtca tctgtaacta ccataagcac ttggacaaag     780
tcccagagat gaaatgcctt tgttataata aaggccacgg taataaggat gaagacgtcg     840
atatccaaat gtaaaatgg gttagaccct tcgccgtagg caactactta ccaatatgtt      900
gccaccagga atacttgatt aacaagatgt gaagaatgaa ccgcatcgaa caatgtaccc     960
agcactcacc ctcgaatcaa aggcagaccc atacgctgga acctaacgac aacgtataag    1020
tcgaggacaa cgtcgacgat ggcgtcaaaa gaactagatg ggttaaccag ttccttcaaa    1080
aagactacca tacggagatc cttagagacc atgaaagtta agtactaac ataaggtccg     1140 actcgtgttg taggaatacg tgggtaaagt gtacaatccg catcgaccac ataagccgcc    1200
gagggataag tcacgatacg taccaaggaa ccattgaaga tcaaactagt cccttggtg    1260 tcttttactt agacgattac ttccaatgtc taagccagtt ctccttcttt gaatattgta    1320
gcatcggcga gtaccaataa aaccggctaa ctagaaggtt atacgatcaa agttgttgag    1380
agcaagcaat gtgaagaagg atcgacgaac cggacatcat ccatagacca aatggcgaaa    1440
```

```
tccatagtcg tgataccgaa agttggattt accaaagtta aagttggtta gacatcaact    1500
gtcagttccg gcacattaat tatgaacccg actatagtaa ttggcacgat tggaaccata    1560
ccttcaatac gtacttgcat tacgagtgtt gaagggagat ctggatcgac gatagcttcg    1620
aggtagatgt ttacctattc agctgccata gctattcgaa ggggccctct ggtgttgcca    1680
aagggagatc tttattaaaa caaattgaaa ttcttcctct atatgtatac ttgggcttga    1740
gtaaagttaa gtttcttttg tatgatgtta aaaaaagaca tgtactactg tagacctttt    1800
ttaatgttct taaaataata cccgtttcgg gttaattact ccgaaaccgc gtcgagttgt    1860
ttcttctata cagaaacaag aaacttcgtg atagattttt gggtcgagcg tactaccttt    1920
acgttacctc gaccaccgtt ccagtttatg tttagatggt tttacacaac tacgcgtcgc    1980
accggtttct acatcgtggt aaataagtcg gactttcacc actagcagca aaattgtcgg    2040
gtaataccgt tcttgtgggt ttaaaactga acaacagtgt cagaataaat gacaaatcgg    2100
tcaatcacgt tttgtaccat ctacaccagc ttccacaagg tctgtttcaa gcgatagcat    2160
aagtgaagaa atgggcggtt tactagttac gcaatagagg ttcattgaaa gacacctgat    2220
tgggtcttca ctaagtcgtt tgacatcgac ttgttccact tttgaatcag gcaccgtacg    2280
ttcaaaaggt actactacag tacttatcgc cgttcataaa tagataagcg taccacttat    2340
cgctgagaaa gtcgaacccg tttctaaatc gaatgtgggg accacgtcag cagaaacttt    2400
tactgtaaaa ggttaataac gttatacttc gttgatgact tttacacata gtttggggat    2460
aagatcagca tggtggcaaa tagttattta taatacacga cctaaatgcg cttgttttga    2520
gaaatcactt gaccaacgcg gtcgttccag tatgtcagaa aaattacagt accgcattgg    2580
gtttacggct tgtctttctt aactgaaaac ggctagagta atgtgttcca agtcaccttc    2640
gaaacgcaca ttaacttctt taatggccac ttttctccg gttgacgtaa ccgatgacat    2700
aaccaccatg caatgaacga cgctgagttc ggataatgca ccgttttgcg gacttttag    2760 tgcatttcag acgctggata taccggtggt aatagctgaa acttttgggt ccgtcgaatc    2820
cacataaata attacttgga catcactcgc caaatctttt ggacttgtta gttaacccaa    2880
taaagctacc agcagtcaac cgtcaatgga agtcaaatga cgcactttta tgcgacatga    2940
ccttaatgat gtagctgttg atgaattttc catttcttgg aagactaaaa ctataaaata    3000
taaccttgtc gctaccatgc ttataggac ggttttaagt attaaagaat aacgcgttaa    3060
acataaactt gttacttaac taaagtggtt tacggcaatt ccaattgcca cacccgaact    3120
tagatagagc acattttgt ggttcgaaga aataacgctg cgtccttctg gtatagcgtg    3180
aaaccctatg aacaaaggca ccgcgtctaa tgaacccacc acttagttgg aaccaaaatc    3240
cacttagacc tgtgcatcgt ccataacagt taggaggttc ggcattattt atgccaacga    3300
tgtggttacg acggttcaaa ctttttatggt ttgttaccga tctaccgcgt cttatagtgg    3360
gacttagaac caccaacgcg accgtccgta cccagtgtgg catgtgacca cttgttcagg    3420
gacgggcgtt gaacccatta cgcgtcatag gttcgtaact tcgccgtggc ccagcgatac    3480
aaaaccattt aaataagatt cgccggcggt ggcgccacct cgagttattt ttttagatc    3540 tacgaatact aagtcatcat cctccgtttg gtatactttc tacaacacta acaacgtcgt    3600
tttgcatgac gctaaccatc gaaaaatcca tcagaacgta gaaatagacg tggtgtcaac    3660 cccgttttgtc gttaagcacg tcaaaatctg tcgcgattac atttttggact tgttcaacta    3720 gtccactaat acccgttgca tgagtgctgt ccgcaccctg ttttgggacg tgcagtccgt    3780
```

```
cgttaacgac gaccataagg tcatgttcac ggacgtagat gcgacttaca gcagacacca   3840
agtccaaacg cacgccatgt aaaccgtcgt gttcggtaag ttacgctact tcggctgtaa   3900
caccagcgtc caccagttct tagatacagt gtttcacgcg tgatatacgt cgacgcatta   3960
cccgtttttt acccattacg tgttaaccac ctatcgtacc accgactacc aaattggcta   4020
cggatattgg tcatagttta cccataatgg cgtcttttat aacatctttt tgacccaaat   4080
ttggcacttc ttgttctagt tgaacgtaac tgaagtgttg ttgcacgacg ccgtcgagtc   4140
cgtcgaccgt tcaaatttct actttaacgg catcagtcgt aaggtgttgc atttccactc   4200
ggacaacata aacgacttct acttatgtaa tttcggttat ggtcggaact ttcggagtgt   4260
tttgatgcgg gtcggaaatt ttttctacca tcgcattggc gtccattacg aagtccgtaa   4320
ttactaccac gtcgtcgtca tgactactac tcacgcctgt ttcgtcgtct taatccagaa   4380 tcggtaacc gtgcataatt tccgatacgg tacagaccat aactcggact ttaatacccc    4440
gaaccaggac agctacgtca tttcttttgg gagttgtttc gtccgacctc gaatctagtc   4500 caactaaaact aacttcggtt acttcgtaaa cgacgtgtcc gaaacccaca acgatttctt   4560
aatccgaatc tggacctatt tcagttgcag ttaccgccac gttaacgtaa cccagtgggt   4620
taaccccgaa gtccaacggc ataaaaccac tgaaataatg tactttacgt cgcggcacta   4680
cggttctttc cgtaacgttg ggagacacaa ccgccaccat acccacaacg tgaacgtcaa   4740
cttgcactga ttcgccggcg agctcaaacc taggttagct atgttcactc aacatccctc   4800
cgttggtacc gtcttcgcca ctagcggctt catagctgag ttgatagtct ccatcaaccg   4860
cagtagctcg cggtagagct tggctgcaac gaccggcatg taaacatgcc gaggcgtcac   4920
ctaccgccgg acttcggtgt gtcactataa ctaaacgacc aatgccactg gcattccgaa   4980
ctactttgtt gcgccgctcg aaactagttg ctggaaaacc tttgaagccg aagggggacct   5040 ctctcgctct aagaggcgcg acatcttcag tggtaacaac acgtgctgct gtagtaaggc   5100
accgcaatag gtcgattcgc gcttgacgtt aaacctctta ccgtcgcgtt actgtaagaa   5160
cgtccataga agctcggtcg gtgctagctg taactagacc gatagaacga ctgttttcgt   5220
tctcttgtat cgcaacggaa ccatccaggt cgccgcctcc ttgagaaact aggccaagga   5280
cttgtcctag ataaactccg cgatttactt tggaattgcg ataccttgag cggcgggctg   5340
acccgaccgc tactcgcttt acatcacgaa tgcaacaggg cgtaaaccat gtcgcgtcat   5400
tggccgtttt agcgcggctt cctacagcga cggctgaccc gttacctcgc ggacggccgg   5460
gtcatagtcg ggcagtatga acttcgatct gtccgaatag aacctgttct tcttctagcg   5520
aaccggagcg cgcgtctagt caaccttctt aaacaggtga tgcactttcc gctctagtgg   5580
ttccatcagc cgtttattta gattcggctt aacccggatc agatatcctc caaaactttt   5640
ctttcctcgt tattagtaaa agaacaagat agttctccca cgataacgag gaaagaaaaa   5700
aagaaaaata aataaatgat cataaaatga atgtatctga aaaacaaat gtaatatctt    5760 tttcttcctc tccaataaaa gaacgtaaat aagtactaac tcataagata aaactaaaac   5820
ataaacaaat tttaacatct ttatcttgaa caaagagaag aacgattaca atgatatcga   5880
aaaactaaaa aaaaaaggtt ttttttttag tttaaaactg aagaagaata gagaatagaa   5940
acttatagag aatagaaact ttattattat agtaacttta ttctttcttc tcgatataag   6000
cttgaactta gaaaacaaaa gattaaattt attcatttt tgccttacat tcatccgctc    6060
ccccgcctac atcggttcac ctagttccgt cacctaacac ttaggtggta cgcgcccaag   6120
ttaagggcag caagcgggta ttaatgagga taaaaaaaa aaaacatttt ttgcttctta    6180
```

```
aattaagcta aaagagagga taaatgatgc cgctgcttct tagtttaata gtgatataaa   6240
taaggaaaaa gatgaagaag aaggttcacg tcctattggg gttccccaac acccaaaaaa   6300
agatggttaa ccccgagagg gaagtggtgg gggtacccct accagatgtc ccaagtattg   6360
atgaggagaa tgatgtcctg cgaatggatc ggttgcgaat ctaggccgag atgggtttga   6420
aaagaccaag tggggttgta aggggtgaac aggctgacaa cgactcgtca aaaacctata   6480
gtttgcctgg aggggtcttc cattaaaatt acaccggcta aagggagaa aacgttagtc    6540 aaagcgatgt cgtgggcgac gagatcgatt aacaggtggg aaaggttcac actaaagata   6600
caatacatac cggcacggat tcccgtatag ccaacttcat ctaagaagaa aactagttag   6660
ttttggggaa gggtttgaca tgttcgaacc gcattagtac cagtatcgac aaaggacaca   6720
ctttaacaat aggcgagtgt taaggtgtgt tgtatgctcg gccttcgtat ttcacatttc   6780
ggaccccacg gattactcac tcgattgagt gtaattaacg caacgcgagt gacgggcgaa   6840
aggtcagccc tttggacagc acggtcgacg taattactta gccggttgcg cgcccctctc   6900
cgccaaacgc ataacccgcg agaaggcgaa ggagcgagtg actgagcgac gcgagccagc   6960
aagccgacgc cgctcgccat agtcgagtga gtttccgcca ttatgccaat aggtgtctta   7020
gtcccctatt gcgtcctttc ttgtacactc gttttccggt cgttttccgg tccttggcat   7080
ttttccggcg caacgaccgc aaaaaggtat ccgaggcggg gggactgctc gtagtgtttt   7140
tagctgcgag ttcagtctcc accgctttgg gctgtcctga tatttctatg gtccgcaaag   7200
ggggaccttc gagggagcac gcgagaggac aaggctggga cggcgaatgg cctatggaca   7260
ggcggaaaga gggaagccct tcgcaccgcg aaagagtatc gagtgcgaca tccatagagt   7320
caagccacat ccagcaagcg aggttcgacc cgacacacgt gcttgggggg caagtcgggc   7380
tggcgacgcg gaataggcca ttgatagcag aactcaggtt gggccattct gtgctgaata   7440
gcggtgaccg tcgtcggtga ccattgtcct aatcgtctcg ctccatacat ccgccacgat   7500
gtctcaagaa cttcaccacc ggattgatgc cgatgtgatc ttcctgtcat aaaccataga   7560
cgcgagacga cttcggtcaa tggaagcctt tttctcaacc atcgagaact aggccgtttg   7620
tttggtggcg accatcgcca ccaaaaaaac aaacgttcgt cgtctaatgc gcgtcttttt   7680
ttcctagagt tcttctagga aactagaaaa gatgccccag actgcgagtc accttgcttt   7740
tgagtgcaat tccctaaaac cagtactcta atagttttc ctagaagtgg atctaggaaa    7800
atttaatttt tacttcaaaa tttagttaga tttcatatat actcatttga accagactgt   7860
caatggttac gaattagtca ctccgtggat agagtcgcta gacagataaa gcaagtaggt   7920
atcaacggac tgaggggcag cacatctatt gatgctatgc cctcccgaat ggtagaccgg   7980
ggtcacgacg ttactatggc gctctgggtg cgagtggccg aggtctaaat agtcgttatt   8040
tggtcggtcg gccttcccgg ctcgcgtctt caccaggacg ttgaaatagg cggaggtagg   8100
tcagataatt aacaacggcc cttcgatctc attcatcaag cggtcaatta tcaaacgcgt   8160
tgcaacaacg gtaacgatgt ccgtagcacc acagtgcgag cagcaaacca taccgaagta   8220
agtcgaggcc aagggttgct agttccgctc aatgtactag ggggtacaac acgttttttc   8280
gccaatcgag gaagccagga ggctagcaac agtcttcatt caaccggcgt cacaaatagtg  8340 agtaccaata ccgtcgtgac gtattaagag aatgacagta cggtaggcat tctacgaaaa   8400
gacactgacc actcatgagt tggttcagta agactcttat cacatacgcc gctggctcaa   8460
cgagaacggg ccgcagttat gccctattat ggcgcggtgt atcgtcttga aattttcacg   8520
```

```
agtagtaacc ttttgcaaga agccccgctt ttgagagttc ctagaatggc gacaactcta   8580
ggtcaagcta cattgggtga gcacgtgggt tgactagaag tcgtagaaaa tgaaagtggt   8640
cgcaaagacc cactcgtttt tgtccttccg ttttacggcg ttttttccct tattcccgct   8700
gtgcctttac aacttatgag tatgagaagg aaaaagttat aataac                 8746

<210> SEQ ID NO 12
<211> LENGTH: 9546
<212> TYPE: DNA
<213> ORGANISM: Artificial Sequence
<220> FEATURE:
<223> OTHER INFORMATION: Synthetic pCAB(2) plasmid (forward strand)

<400> SEQUENCE: 12
tgaagcattt atcagggtta ttgtctcatg agcggataca tatttgaatg tatttagaaa     60
aataaacaaa taggggttcc gcgcacattt ccccgaaaag tgccacctga cgtctaagaa    120
accattatta tcatgacatt aacctataaa aataggcgta tcacgaggcc ctttcgtctc    180
gcgcgtttcg gtgatgacgg tgaaaacctc tgacacatgc agctcccgga gacggtcaca    240
gcttgtctgt aagcggatgc cgggagcaga caagcccgtc agggcgcgtc agcgggtgtt    300
ggcgggtgtc ggggctggct taactatgcg gcatcagagc agattgtact gagagtgcac    360
catatgcggt gtgaaatacc gcacagatgc gtaaggagaa ataccgcat caggcgccat     420 tcgccattca ggctgcgcaa ctgttgggaa gggcgatcgg tgcgggcctc ttcgctatta    480
cgccagctgg cgaaagggg atgtgctgca aggcgattaa gttgggtaac gccagggttt     540
tcccagtcac gacgttgtaa aacgacggcc agtgaattca tgactgcaat tttagagaga    600
cgcgaaagcg aaagcctatg ggtcgcttc tgtaactgga taactagcac tgaaaaccgt     660
ctttacattg gatggtttgg tgttttgatg atccctacct tattgacggc aacttctgta    720
tttattattg ccttcattgc tgctcctcca gtagacattg atggtattcg tgaacctgtt    780
tcagggtctc tactttacgg aaacaatatt atttccggtg ccattattcc tacttctgca    840
gctataggtt tacatttta cccaatctgg gaagcggcat ccgttgatga atggttatac     900
aacggtggtc cttatgaact aattgttcta cacttcttac ttggcgtagc ttgttacatg    960
ggtcgtgagt gggagcttag tttccgtctg ggtatgcgac cttggattgc tgttgcatat   1020
tcagctcctg ttgcagctgc taccgcagtt ttcttgatct acccaattgg tcaaggaagt   1080
ttttctgatg gtatgcctct aggaatctct ggtactttca atttcatgat tgtattccag   1140
gctgagcaca catccttat gcacccattt cacatgttag gcgtagctgg tgtattcggc    1200
ggctccctat tcagtgctat gcatggttcc ttggtaactt ctagtttgat cagggaaacc   1260
acagaaaatg aatctgctaa tgaaggttac agattcggtc aagaggaaga aacttataac   1320
atcgtagccg ctcatggtta ttttggccga ttgatcttcc aatatgctag tttcaacaac   1380
tctcgttcgt tacacttctt cctagctgct tggcctgtag taggtatctg gtttaccgct   1440
ttaggtatca gcactatggc tttcaaccta aatggtttca atttcaacca atctgtagtt   1500
gacagtcaag gccgtgtaat taatacttgg gctgatatca ttaaccgtgc taaccttggt   1560
atggaagtta tgcatgaacg taatgctcac aacttccctc tagacctagc tgctatcgaa    1620
gctccatcta caaatggata agtcgacggt atcgataagc ttccccggga gaccacaacg   1680
gtttccctct agaaataatt ttgtttaact ttaagaagga gatatacata tgaacccgaa    1740
ctcatttcaa ttcaaagaaa acatactaca atttttttct gtacatgatg acatctggaa   1800
aaaattacaa gaatttttatt atgggcaaag cccaattaat gaggctttgg cgcagctcaa   1860
```

```
caaagaagat atgtctttgt tctttgaagc actatctaaa aacccagctc gcatgatgga    1920
aatgcaatgg agctggtggc aaggtcaaat acaaatctac caaaatgtgt tgatgcgcag    1980
cgtggccaaa gatgtagcac catttattca gcctgaaagt ggtgatcgtc gttttaacag    2040
cccattatgg caagaacacc caaattttga cttgttgtca cagtcttatt tactgtttag    2100
ccagttagtg caaacatgg tagatgtggt cgaaggtgtt ccagacaaag ttcgctatcg    2160
tattcacttc tttacccgcc aaatgatcaa tgcgttatct ccaagtaact ttctgtggac    2220
taacccagaa gtgattcagc aaactgtagc tgaacaaggt gaaaacttag tccgtggcat    2280
gcaagttttc catgatgatg tcatgaatag cggcaagtat ttatctattc gcatggtgaa    2340
tagcgactct ttcagcttgg gcaaagattt agcttacacc cctggtgcag tcgtctttga    2400
aaatgacatt ttccaattat tgcaatatga agcaactact gaaaatgtgt atcaaacccc    2460
tattctagtc gtaccaccgt ttatcaataa atattatgtg ctggatttac gcgaacaaaa    2520
ctctttagtg aactggttgc gccagcaagg tcatacagtc ttttttaatgt catggcgtaa    2580 cccaaatgcc gaacagaaag aattgacttt tgccgatctc attacacaag gttcagtgga    2640
agctttgcgt gtaattgaag aaattaccgg tgaaaagag gccaactgca ttggctactg    2700
tattggtggt acgttacttg ctgcgactca agcctattac gtggcaaaac gcctgaaaaa    2760
tcacgtaaag tctgcgacct atatggccac cattatcgac tttgaaaacc caggcagctt    2820
aggtgtattt attaatgaac ctgtagtgag cggtttagaa aacctgaaca atcaattggg    2880
ttatttcgat ggtcgtcagt tggcagttac cttcagttta ctgcgtgaaa atacgctgta    2940
ctggaattac tacatcgaca actacttaaa aggtaaagaa ccttctgatt ttgatatttt    3000
atattggaac agcgatggta cgaatatccc tgccaaaatt cataatttct tattgcgcaa    3060
tttgtatttg aacaatgaat tgatttcacc aaatgccgtt aaggttaacg gtgtgggctt    3120
gaatctatct cgtgtaaaaa caccaagctt ctttattgcg acgcaggaag accatatcgc    3180
actttgggat acttgtttcc gtggcgcaga ttacttgggt ggtgaatcaa ccttggtttt    3240
aggtgaatct ggacacgtag caggtattgt caatcctcca agccgtaata atacgcgttg    3300
ctacaccaat gctgccaagt ttgaaaatac caaacaatgg ctagatggcg cagaatatca    3360
ccctgaatct tggtggttgc gctggcaggc atgggtcaca ccgtacactg gtgaacaagt    3420
ccctgcccgc aacttgggta atgcgcagta tccaagcatt gaagcggcac cgggtcgcta    3480
tgttttggta aatttattct aagcggccgc caccgcggtg gagctcaata aaaaaaatct    3540
agatgcttat gattcagtag taggaggcaa accatatgaa agatgttgtg attgttgcag    3600
caaaacgtac tgcgattggt agctttttag gtagtcttgc atctttatct gcaccacagt    3660
tggggcaaac agcaattcgt gcagttttag acagcgctaa tgtaaaacct gaacaagttg    3720
atcaggtgat tatgggcaac gtactcacga caggcgtggg acaaaaccct gcacgtcagg    3780
cagcaattgc tgctggtatt ccagtacaag tgcctgcatc tacgctgaat gtcgtctgtg    3840
gttcaggttt gcgtgcggta catttggcag cacaagccat tcaatgcgat gaagccgaca    3900
ttgtggtcgc aggtggtcaa gaatctatgt cacaaagtgc gcactatatg cagctgcgta    3960
atgggcaaaa aatgggtaat gcacaattgg tggatacgat ggtggctgat ggtttaaccg    4020
atgcctataa ccagtatcaa atgggtatta ccgcagaaaa tattgtagaa aaactgggtt    4080
taaaccgtga agaacaagat caacttgcat tgacttcaca acaacgtgct gcggcagctc    4140
aggcagctgg caagtttaaa gatgaaattg ccgtagtcag cattccacaa cgtaaaggtg    4200
```

```
agcctgttgt atttgctgaa gatgaataca ttaaagccaa taccagcctt gaaagcctca      4260
caaaactacg cccagccttt aaaaaagatg gtagcgtaac cgcaggtaat gcttcaggca      4320
ttaatgatgg tgcagcagca gtactgatga tgagtgcgga caaagcagca gaattaggtc      4380
ttaagccatt ggcacgtatt aaaggctatg ccatgtctgg tattgagcct gaaattatgg      4440
ggcttggtcc tgtcgatgca gtaaagaaaa ccctcaacaa agcaggctgg agcttagatc      4500
aggttgattt gattgaagcc aatgaagcat ttgctgcaca ggctttgggt gttgctaaag      4560
aattaggctt agacctggat aaagtcaacg tcaatggcgg tgcaattgca ttgggtcacc      4620 caattgggc ttcaggttgc cgtatttttgg tgactttatt acatgaaatg cagcgccgtg      4680
atgccaagaa aggcattgca accctctgtg ttggcggtgg tatgggtgtt gcacttgcag      4740
ttgaacgtga ctaagcggcc gctcgagtgg cggctcaaga tcagcctcat caaaaccttta      4800 tattccctga ggaggttcta cccatatgac aacattacaa ggtaaagtag caatcgtaac      4860
aggcggatct aaaggtatcg gggcagcaat tacacgtgag cttgcttcta atggagtaaa      4920
agtagcagta aactataaca gcagtaaaga atctgcagaa gcaattgtaa aagaaattaa      4980
agacaacggc ggagaagcta ttgcggttca agctgacgtg tcttatgtag atcaagcaaa      5040
acacctaatc gaagaaacaa aagctgcgtt tggtcaatta gacattctag taaacaatgc      5100
tggaattacg cgcgaccgtt cattcaagaa gttaggtgaa gaagattgga aaaaagtaat      5160
tgatgtaaac ttacatagcg tatacaacac aacatcagct gcgctaacgc accttttaga      5220
atctgaaggt ggtcgtgtta tcaatatttc atcaattatt ggtcaagcgg gcggatttgg      5280
tcaaacaaac tactcagctg ctaaagcagg tatgctagga ttcactaaat cattagctct      5340
tgaactagct aagacaggcg taacggttaa tgcaatttgc ccaggattta ttgaaacgga      5400
aatggtgatg gcaattcctg aagatgttcg tgcaaaaatt gttgcgaaaa ttccaactcg      5460
tcgcttaggt cacgctgaag aaattgcacg tggagttgtt tacttagcaa agacggcgc      5520 gtacattaca ggacaacagt taaacattaa cggcggctta tacatgtaat ggatccaatc      5580
gatacaagtg agttgtaggg aggcaaccat ggcagaagcg gtgatcgccg aagtatcgac      5640
tcaactatca gaggtagttg gcgtcatcga gcgccatctc gaaccgacgt tgctggccgt      5700
acatttgtac ggctccgcag tggatggcgg cctgaagcca cacagtgata ttgatttgct      5760
ggttacggtg accgtaaggc ttgatgaaac aacgcggcga gctttgatca acgaccttt      5820 ggaaacttcg gcttcccctg gagagagcga gattctccgc gctgtagaag tcaccattgt      5880
tgtgcacgac gacatcattc cgtggcgtta tccagctaag cgcgaactgc aatttggaga      5940
atggcagcgc aatgacattc ttgcaggtat cttcgagcca gccacgatcg acattgatct      6000
ggctatcttg ctgacaaaag caagagaaca tagcgttgcc ttggtaggtc cagcggcgga      6060
ggaactcttt gatccggttc ctgaacagga tctatttgag gcgctaaatg aaaccttaac      6120
gctatggaac tcgccgcccg actgggctgg cgatgagcga aatgtagtgc ttacgttgtc      6180
ccgcatttgg tacagcgcag taaccggcaa aatcgcgccg aaggatgtcg ctgccgactg      6240
ggcaatggag cgcctgccgg cccagtatca gcccgtcata cttgaagcta gacaggctta      6300
tcttggacaa gaagaagatc gcttggcctc gcgcgcagat cagttggaag aatttgtcca      6360
ctacgtgaaa ggcgagatca ccaaggtagt cggcaaataa atctaagccg aattgggcct      6420
agtctatagg aggttttgaa aagaaaggag caataatcat tttcttgttc tatcaagagg      6480
gtgctattgc tccttctttt ttttctttttt atttatttac tagtatttta cttacataga      6540
cttttttgtt tacattatag aaaaagaagg agaggttatt ttcttgcatt tattcatgat      6600
```

```
tgagtattct attttgattt tgtatttgtt taaaattgta gaaatagaac ttgtttctct      6660
tcttgctaat gttactatat cttttgatt ttttttttcc aaaaaaaaaa tcaaattttg      6720
acttcttctt atctcttatc tttgaatatc tcttatcttt gaaataataa tatcattgaa      6780
ataagaaaga agagctatat tcgaacttga atcttttgtt ttctaattta aataatgtaa      6840
aaacggaatg taagtaggcg aggggcgga tgtagccaag tggatcaagg cagtggattg      6900
tgaatccacc atgcgcgggt tcaattcccg tcgttcgccc ataattactc ctatttttt      6960 tttttttgta aaaacgaaga atttaattcg attttctctc ctatttacta cggcgacgaa      7020
gaatcaaatt atcactatat ttattccttt ttctacttct tcttccaagt gcaggataac      7080
cccaaggggt tgtgggtttt tttctaccaa ttggggctct cccttcacca cccccatggg      7140
gatggtctac agggttcata actactcctc ttactacagg acgcttacct agccaacgct      7200
tagatccggc tctacccaaa cttttctggt tcaccccaac attccccact tgtccgactg      7260
ttgctgagca gttttggat atcaaacgga cctccccaga aggtaatttt aatgtggccg      7320 atttccctc ttttgcaatc agtttcgcta cagcacccgc tgctctagct aattgtccac      7380
cctttccaag tgtgattct atgttatgta tggccgtgcc taagggcata tcggttgaag      7440
tagattcttc ttttgatcaa tcaaaacccc ttcccaaact gtacaagctt ggcgtaatca      7500
tggtcatagc tgtttcctgt gtgaaattgt tatccgctca cattccaca caacatacga      7560 gccggaagca taaagtgtaa agcctggggt gcctaatgag tgagctaact cacattaatt      7620
gcgttgcgct cactgcccgc tttccagtcg ggaaacctgt cgtgccagct gcattaatga      7680
atcggccaac gcgcggggag aggcggttg cgtattgggc gctcttccgc ttcctcgctc      7740
actgactcgc tgcgctcggt cgttcggctg cggcgagcgg tatcagctca ctcaaaggcg      7800
gtaatacggt tatccacaga atcaggggat aacgcaggaa agaacatgtg agcaaaaggc      7860
cagcaaaagg ccaggaaccg taaaaaggcc gcgttgctgg cgttttccca taggctccgc      7920 cccctgacg agcatcacaa aaatcgacgc tcaagtcaga ggtggcgaaa cccgacagga      7980
ctataaagat accaggcgtt ccccctgga agctccctcg tgcgctctcc tgttccgacc      8040
ctgccgctta ccggatacct gtccgccttt ctcccttcgg gaagcgtggc gctttctcat      8100
agctcacgct gtaggtatct cagttcggtg taggtcgttc gctccaagct gggctgtgtg      8160
cacgaacccc ccgttcagcc cgaccgctgc gccttatccg gtaactatcg tcttgagtcc      8220
aacccggtaa gacacgactt atcgccactg gcagcagcca ctggtaacag gattagcaga      8280
gcgaggtatg taggcggtgc tacagagttc ttgaagtggt ggcctaacta cggctacact      8340
agaaggacag tatttggtat ctgcgctctg ctgaagccag ttaccttcgg aaaaagagtt      8400
ggtagctctt gatccggcaa acaaaccacc gctggtagcg gtggttttt tgtttgcaag      8460 cagcagatta cgcgcagaaa aaaggatctc aagaagatc ctttgatctt ttctacgggg      8520
tctgacgctc agtggaacga aaactcacgt taagggattt tggtcatgag attatcaaaa      8580
aggatcttca cctagatcct tttaaattaa aaatgaagtt ttaaatcaat ctaaagtata      8640
tatgagtaaa cttggtctga cagttaccaa tgcttaatca gtgaggcacc tatctcagcg      8700
atctgtctat ttcgttcatc catagttgcc tgactccccg tcgtgtagat aactacgata      8760
cgggagggct taccatctgg ccccagtgct gcaatgatac cgcgagaccc acgctcaccg      8820
gctccagatt tatcagcaat aaaccagcca gccggaaggg ccgagcgcag aagtggtcct      8880
gcaactttat ccgcctccat ccagtctatt aattgttgcc gggaagctag agtaagtagt      8940
```

```
tcgccagtta atagtttgcg caacgttgtt gccattgcta caggcatcgt ggtgtcacgc   9000
tcgtcgtttg gtatggcttc attcagctcc ggttcccaac gatcaaggcg agttacatga   9060
tcccccatgt tgtgcaaaaa agcggttagc tccttcggtc ctccgatcgt tgtcagaagt   9120
aagttggccg cagtgttatc actcatggtt atggcagcac tgcataattc tcttactgtc   9180
atgccatccg taagatgctt ttctgtgact ggtgagtact caaccaagtc attctgagaa   9240
tagtgtatgc ggcgaccgag ttgctcttgc ccggcgtcaa tacgggataa taccgcgcca   9300
catagcagaa ctttaaaagt gctcatcatt ggaaaacgtt cttcggggcg aaaactctca   9360
aggatcttac cgctgttgag atccagttcg atgtaaccca ctcgtgcacc caactgatct   9420
tcagcatctt ttactttcac cagcgtttct gggtgagcaa aaacaggaag gcaaaatgcc   9480
gcaaaaaagg gaataagggc gacacggaaa tgttgaatac tcatactctt ccttttttcaa  9540 tattat                                                              9546

<210> SEQ ID NO 13
<211> LENGTH: 9546
<212> TYPE: DNA
<213> ORGANISM: Artificial Sequence
<220> FEATURE:
<223> OTHER INFORMATION: Synthetic pCAB(2) plasmid (reverse strand)

<400> SEQUENCE: 13
acttcgtaaa tagtcccaat aacagagtac tcgcctatgt ataaacttac ataaatcttt     60
ttatttgttt atccccaagg cgcgtgtaaa ggggcttttc acggtggact gcagattctt    120
tggtaataat agtactgtaa ttggatattt ttatccgcat agtgctccgg gaaagcagag    180
cgcgcaaagc cactactgcc acttttggag actgtgtacg tcgagggcct ctgccagtgt    240
cgaacagaca ttcgcctacg gccctcgtct gttcgggcag tcccgcgcag tcgcccacaa    300
ccgcccacag ccccgaccga attgatacgc cgtagtctcg tctaacatga ctctcacgtg    360
gtatacgcca cactttatgg cgtgtctacg cattcctctt ttatggcgta gtccgcggta    420
agcggtaagt ccgacgcgtt gacaacccct cccgctagcc acgcccggag aagcgataat    480
gcggtcgacc gctttccccc tacacgacgt tccgctaatt caacccattg cggtcccaaa    540
agggtcagtg ctgcaacatt ttgctgccgg tcacttaagt actgacgtta aaatctctct    600
gcgctttcgc tttcggatac cccagcgaag acattgacct attgatcgtg acttttggca    660
gaaatgtaac ctaccaaacc acaaaactac tagggatgga ataactgccg ttgaagacat    720
aaataataac ggaagtaacg acgaggaggt catctgtaac taccataagc acttggacaa    780
agtcccagag atgaaatgcc tttgttataa taaaggccac ggtaataagg atgaagacgt    840
cgatatccaa atgtaaaaat gggttagacc cttcgccgta ggcaactact taccaatatg    900
ttgccaccag gaatacttga ttaacaagat gtgaagaatg aaccgcatcg aacaatgtac    960
ccagcactca ccctcgaatc aaaggcagac ccatacgctg gaacctaacg acaacgtata   1020
agtcgaggac aacgtcgacg atggcgtcaa agaactaga tgggttaacc agttccttca   1080
aaaagactac catacggaga tccttagaga ccatgaaagt taaagtacta acataaggtc   1140
cgactcgtgt tgtaggaata cgtgggtaaa gtgtacaatc cgcatcgacc acataagccg   1200
ccgagggata agtcacgata cgtaccaagg aaccattgaa gatcaaacta gtcccttgg    1260 tgtcttttac ttagacgatt acttccaatg tctaagccag ttctcctcct ttgaatattg   1320
tagcatcggc gagtaccaat aaaaccggct aactagaagg ttatacgatc aaagttgttg   1380
agagcaagca atgtgaagaa ggatcgacga accggacatc atccatagac caaatggcga   1440
```

```
aatccatagt cgtgataccg aaagttggat ttaccaaagt taaagttggt tagacatcaa   1500
ctgtcagttc cggcacatta attatgaacc cgactatagt aattggcacg attggaacca   1560
taccttcaat acgtacttgc attacgagtg ttgaagggag atctggatcg acgatagctt   1620
cgaggtagat gtttacctat tcagctgcca tagctattcg aaggggccct ctggtgttgc   1680
caaagggaga tctttattaa aacaaattga aattcttcct ctatatgtat acttgggctt   1740
gagtaaagtt aagtttcttt tgtatgatgt taaaaaaaga catgtactac tgtagacctt   1800
ttttaatgtt cttaaaataa tacccgtttc gggttaatta ctccgaaacc gcgtcgagtt   1860
gtttcttcta tacagaaaca agaaacttcg tgatagattt ttgggtcgag cgtactacct   1920
ttacgttacc tcgaccaccg ttccagttta tgtttagatg gttttacaca actacgcgtc   1980
gcaccggttt ctacatcgtg gtaaataagt cggactttca ccactagcag caaaattgtc   2040
gggtaatacc gttcttgtgg gtttaaaact gaacaacagt gtcagaataa atgacaaatc   2100
ggtcaatcac gttttgtacc atctacacca gcttccacaa ggtctgtttc aagcgatagc   2160
ataagtgaag aaatgggcgg tttactagtt acgcaataga ggttcattga agacacctg    2220 attgggtctt cactaagtcg tttgacatcg acttgttcca cttttgaatc aggcaccgta   2280
cgttcaaaag gtactactac agtacttatc gccgttcata aatagataag cgtaccactt   2340
atcgctgaga aagtcgaacc cgtttctaaa tcgaatgtgg ggaccacgtc agcagaaact   2400
tttactgtaa aaggttaata acgttatact tcgttgatga cttttacaca tagtttgggg   2460
ataagatcag catggtggca aatagttatt tataatacac gacctaaatg cgcttgtttt   2520
gagaaatcac ttgaccaacg cggtcgttcc agtatgtcag aaaaattaca gtaccgcatt   2580
gggtttacgg cttgtctttc ttaactgaaa acggctagag taatgtgttc caagtcacct   2640
tcgaaacgca cattaacttc tttaatggcc actttttctc cggttgacgt aaccgatgac   2700
ataaccacca tgcaatgaac gacgctgagt tcggataatg caccgttttg cggactttt    2760 agtgcatttc agacgctgga tataccggtg gtaatagctg aaacttttgg gtccgtcgaa   2820
tccacataaa taattacttg gacatcactc gccaaatctt ttggacttgt tagttaaccc   2880
aataaagcta ccagcagtca accgtcaatg gaagtcaaat gacgcacttt tatgcgacat   2940
gaccttaatg atgtagctgt tgatgaattt tccatttctt ggaagactaa aactataaaa   3000
tataaccttg tcgctaccat gcttataggg acggttttaa gtattaaaga ataacgcgtt   3060
aaacataaac ttgttactta actaaagtgg tttacggcaa ttccaattgc cacacccgaa   3120
cttagataga gcacattttt gtggttcgaa gaaataacgc tgcgtccttc tggtatagcg   3180
tgaaacccta tgaacaaagg caccgcgtct aatgaaccca ccacttagtt ggaaccaaaa   3240
tccacttaga cctgtgcatc gtccataaca gttaggaggt tcggcattat ttatgccaac   3300
gatgtggtta cgacggttca aacttttatg gtttgttacc gatctaccgc gtcttatagt   3360
gggacttaga accaccaacg cgaccgtccg tacccagtgt ggcatgtgac cacttgttca   3420
gggacgggcg ttgaacccat tacgcgtcat aggttcgtaa cttcgccgtg gcccagcgat   3480
acaaaaccat ttaaataaga ttcgccggcg gtggcgccac ctcgagttat tttttttaga   3540
tctacgaata ctaagtcatc atcctccgtt tggtatactt tctacaacac taacaacgtc   3600
gttttgcatg acgctaacca tcgaaaaatc catcagaacg tagaaataga cgtggtgtca   3660
accccgtttg tcgttaagca cgtcaaaatc tgtcgcgatt acattttgga cttgttcaac   3720
tagtccacta atacccgttg catgagtgct gtccgcaccc tgttttggga cgtgcagtcc   3780
```

```
gtcgttaacg acgaccataa ggtcatgttc acggacgtag atgcgactta cagcagacac    3840
caagtccaaa cgcacgccat gtaaaccgtc gtgttcggta agttacgcta cttcggctgt    3900
aacaccagcg tccaccagtt cttagataca gtgtttcacg cgtgatatac gtcgacgcat    3960
tacccgtttt ttacccatta cgtgttaacc acctatcgta ccaccgacta ccaaattggc    4020
tacggatatt ggtcatagtt tacccataat ggcgtctttt ataacatctt tttgacccaa    4080
atttggcact tcttgttcta gttgaacgta actgaagtgt tgttgcacga cgccgtcgag    4140
tccgtcgacc gttcaaattt ctactttaac ggcatcagtc gtaaggtgtt gcatttccac    4200
tcggacaaca taaacgactt ctacttatgt aatttcggtt atggtcggaa ctttcggagt    4260
gttttgatgc gggtcggaaa ttttttctac catcgcattg gcgtccatta cgaagtccgt    4320
aattactacc acgtcgtcgt catgactact actcacgcct gtttcgtcgt cttaatccag    4380
aattcggtaa ccgtgcataa tttccgatac ggtacagacc ataactcgga ctttaatacc    4440
ccgaaccagg acagctacgt catttctttt gggagttgtt tcgtccgacc tcgaatctag    4500
tccaactaaa ctaacttcgg ttacttcgta aacgacgtgc ccgaaaccca caacgatttc    4560
ttaatccgaa tctggaccta tttcagttgc agttaccgcc acgttaacgt aacccagtgg    4620
gttaaccccg aagtccaacg gcataaaacc actgaaataa tgtactttac gtcgcggcac    4680
tacggttctt tccgtaacgt tgggagacac aaccgccacc atacccacaa cgtgaacgtc    4740
aacttgcact gattcgccgg cgagctcacc gccgagttct agtcggagta gttttggaat    4800
ataagggact cctccaagat gggtatactg ttgtaatgtt ccatttcatc gttagcattg    4860
tccgcctaga tttccatagc cccgtcgtta atgtgcactc gaacgaagat tacctcattt    4920
tcatcgtcat ttgatattgt cgtcatttct tagacgtctt cgttaacatt ttctttaatt    4980
tctgttgccg cctcttcgat aacgccaagt tcgactgcac agaatacatc tagttcgttt    5040
tgtggattag cttctttgtt ttcgacgcaa accagttaat ctgtaagatc atttgttacg    5100
accttaatgc gcgctggcaa gtaagttctt caatccactt cttctaacct tttttcatta    5160
actacatttg aatgtatcgc atatgttgtg ttgtagtcga cgcgattgcg tggaaaatct    5220
tagacttcca ccagcacaat agttataaag tagttaataa ccagttcgcc cgcctaaacc    5280
agtttgtttg atgagtcgac gatttcgtcc atacgatcct aagtgattta gtaatcgaga    5340
acttgatcga ttctgtccgc attgccaatt acgttaaacg ggtcctaaat aactttgcct    5400
ttaccactac cgttaaggac ttctacaagc acgttttaa caacgctttt aaggttgagc    5460
agcgaatcca gtgcgacttc tttaacgtgc acctcaacaa atgaatcgtt ttctgccgcg    5520
catgtaatgt cctgttgtca atttgtaatt gccgccgaat atgtacatta cctaggttag    5580
ctatgttcac tcaacatccc tccgttggta ccgtcttcgc cactagcggc ttcatagctg    5640
agttgatagt ctccatcaac cgcagtagct cgcggtagag cttggctgca acgaccggca    5700
tgtaaacatg ccgaggcgtc acctaccgcc ggacttcggt gtgtcactat aactaaacga    5760
ccaatgccac tggcattccg aactactttg ttgcgccgct cgaaactagt tgctggaaaa    5820
cctttgaagc cgaaggggac ctctctcgct ctaagaggcg cgacatcttc agtggtaaca    5880
acacgtgctg ctgtagtaag gcaccgcaat aggtcgattc gcgcttgacg ttaaacctct    5940
taccgtcgcg ttactgtaag aacgtccata gaagctcggt cggtgctagc tgtaactaga    6000
ccgatagaac gactgttttc gttctcttgt atcgcaacgg aaccatccag gtcgccgcct    6060 cccttgagaaa ctaggccaag gacttgtcct agataaactc cgcgatttac tttgaaattg    6120
cgataccttg agcggcgggc tgacccgacc gctactcgct ttacatcacg aatgcaacag    6180
```

```
ggcgtaaacc atgtcgcgtc attggccgtt ttagcgcggc ttcctacagc gacggctgac  6240
ccgttacctc gcggacggcc gggtcatagt cgggcagtat gaacttcgat ctgtccgaat  6300
agaacctgtt cttcttctag cgaaccgag cgcgcgtcta gtcaaccttc ttaaacaggt   6360
gatgcacttt ccgctctagt ggttccatca gccgtttatt tagattcggc ttaacccgga  6420
tcagatatcc tccaaaactt ttctttcctc gttattagta aaagaacaag atagttctcc  6480
cacgataacg aggaaagaaa aaagaaaaa taaataaatg atcataaaat gaatgtatct   6540
gaaaaaacaa atgtaatatc ttttcttcc tctccaataa agaacgtaa ataagtacta    6600 actcataaga taaaactaaa acataaacaa attttaacat ctttatcttg aacaaagaga  6660
agaacgatta caatgatata gaaaaactaa aaaaaaaagg ttttttttt agtttaaaac   6720 tgaagaagaa tagagaatag aaacttatag agaatagaaa ctttattatt atagtaactt  6780
tattctttct tctcgatata agcttgaact tagaaaacaa aagattaaat ttattacatt  6840
tttgccttac attcatccgc tcccccgcct acatcggttc acctagttcc gtcacctaac  6900
acttaggtgg tacgcgccca agttaagggc agcaagcggg tattaatgag gataaaaaaa  6960
aaaaaaacat ttttgcttct taaattaagc taaaagagag gataaatgat gccgctgctt  7020
cttagtttaa tagtgatata aataaggaaa aagatgaaga agaaggttca cgtcctattg  7080
gggttcccca acacccaaaa aaagatggtt aacccccgaga gggaagtggt gggggtaccc  7140
ctaccagatg tcccaagtat tgatgaggag aatgatgtcc tgcgaatgga tcggttgcga  7200
atctaggccg agatgggttt gaaaagacca agtgggttg taaggggtga acaggctgac    7260
aacgactcgt caaaaaccta tagtttgcct ggagggggtct tccattaaaa ttacaccggc  7320
taaaggggag aaaacgttag tcaaagcgat gtcgtgggcg acgagatcga ttaacaggtg   7380
ggaaaggttc acactaaaga tacaatacat accggcacgg attcccgtat agccaacttc  7440
atctaagaag aaaactagtt agttttgggg aagggtttga catgttcgaa ccgcattagt   7500
accagtatcg acaaaggaca cactttaaca ataggcgagt gttaaggtgt gttgtatgct  7560
cggccttcgt atttcacatt tcggacccca cggattactc actcgattga gtgtaattaa   7620
cgcaacgcga gtgacgggcg aaaggtcagc cctttggaca gcacggtcga cgtaattact  7680
tagccggttg cgcgcccctc tccgccaaac gcataacccg cgagaaggcg aaggagcgag  7740
tgactgagcg acgcgagcca gcaagccgac gccgctcgcc atagtcgagt gagtttccgc  7800
cattatgcca ataggtgtct tagtccccta ttgcgtcctt tcttgtacac tcgttttccg   7860 gtcgtttttcc ggtccttggc attttttccgg cgcaacgacc gcaaaaaggt atccgaggcg  7920 ggggggactgc tcgtagtgtt tttagctgcg agttcagtct ccaccgcttt gggctgtcct  7980
gatatttcta tggtccgcaa agggggacct tcgagggagc acgcgagagg acaaggctgg  8040
gacggcgaat ggcctatgga caggcggaaa gagggaagcc cttcgcaccg cgaaagagta  8100
tcgagtgcga catccataga gtcaagccac atccagcaag cgaggttcga cccgacacac  8160
gtgcttgggg ggcaagtcgg gctggcgacg cggaataggc cattgatagc agaactcagg  8220
ttgggccatt ctgtgctgaa tagcggtgac cgtcgtcggt gaccattgtc ctaatcgtct  8280
cgctccatac atccgccacg atgtctcaag aacttcacca ccggattgat gccgatgtga  8340
tcttcctgtc ataaaccata gacgcgagac gacttcggtc aatggaagcc ttttctcaa    8400 ccatcgagaa ctaggccgtt tgtttggtgg cgaccatcgc caccaaaaaa acaaacgttc  8460
gtcgtctaat gcgcgtcttt ttttcctaga gttcttctag gaaactagaa aagatgcccc  8520
```

-continued

```
agactgcgag tcaccttgct tttgagtgca attccctaaa accagtactc taatagtttt   8580
tcctagaagt ggatctagga aaatttaatt tttacttcaa aatttagtta gatttcatat   8640
atactcattt gaaccagact gtcaatggtt acgaattagt cactccgtgg atagagtcgc   8700
tagacagata aagcaagtag gtatcaacgg actgaggggc agcacatcta ttgatgctat   8760
gccctcccga atggtagacc ggggtcacga cgttactatg gcgctctggg tgcgagtggc   8820
cgaggtctaa atagtcgtta tttggtcggt cggccttccc ggctcgcgtc ttcaccagga   8880
cgttgaaata ggcggaggta ggtcagataa ttaacaacgg cccttcgatc tcattcatca   8940
agcggtcaat tatcaaacgc gttgcaacaa cggtaacgat gtccgtagca ccacagtgcg   9000
agcagcaaac cataccgaag taagtcgagg ccaagggttg ctagttccgc tcaatgtact   9060
aggggggtaca acacgttttt tcgccaatcg aggaagccag gaggctagca acagtcttca   9120
ttcaaccggc gtcacaatag tgagtaccaa taccgtcgtg acgtattaag agaatgacag   9180
tacggtaggc attctacgaa aagacactga ccactcatga gttggttcag taagactctt   9240
atcacatacg ccgctggctc aacgagaacg ggccgcagtt atgccctatt atggcgcggt   9300
gtatcgtctt gaaattttca cgagtagtaa ccttttgcaa gaagccccgc ttttgagagt   9360
tcctagaatg gcgacaactc taggtcaagc tacattgggt gagcacgtgg gttgactaga   9420
agtcgtagaa aatgaaagtg gtcgcaaaga cccactcgtt tttgtccttc cgttttacgg   9480
cgttttttcc cttattcccg ctgtgccttt acaacttatg agtatgagaa ggaaaaagtt   9540
ataata                                                              9546
```